(12) United States Patent
Romzek et al.

(10) Patent No.: US 10,159,550 B2
(45) Date of Patent: *Dec. 25, 2018

(54) VAGINAL INSERT METHOD OF MANUFACTURE

(71) Applicant: Kimberly-Clark Worldwide, Inc., Neenah, WI (US)

(72) Inventors: Chadwick I. Romzek, Neenah, WI (US); Claudiu Andrei Bouruc, Appleton, WI (US); Todd W. Wilkes, Appleton, WI (US); David John Enz, Neenah, WI (US); Jesse J. Pasterski, Greenville, WI (US); Kurt G. Krupka, Hortonville, WI (US); Brian Wayne Tomac, De Pere, WI (US); Sarah Anne Olson, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 662 days.

This patent is subject to a terminal disclaimer.

(21) Appl. No.: 14/137,823

(22) Filed: Dec. 20, 2013

(65) Prior Publication Data
US 2015/0173875 A1 Jun. 25, 2015

(51) Int. Cl.
*A61F 2/00* (2006.01)
*B65H 69/04* (2006.01)

(52) U.S. Cl.
CPC ............ *A61F 2/0009* (2013.01); *A61F 2/005* (2013.01); *B65H 69/04* (2013.01); *B65H 2701/31* (2013.01); *Y10T 29/49826* (2015.01)

(58) Field of Classification Search
CPC ........ A61F 2/0009; A61F 2/005; B65H 69/04
See application file for complete search history.

(56) References Cited

U.S. PATENT DOCUMENTS

| | | |
|---|---|---|
| 2,134,930 A | 11/1938 | Reynolds |
| 2,235,465 A | 3/1941 | Stamm |
| 2,238,450 A | 4/1941 | Rabell |
| 2,330,257 A | 9/1943 | Bailey |
| 2,566,190 A | 8/1951 | Greiner et al. |
| 3,397,695 A | 8/1968 | Voss |
| 3,559,646 A | 2/1971 | Mullan |
| 3,683,915 A | 8/1972 | Voss |
| 3,712,305 A | 1/1973 | Wennerblom et al. |
| 3,856,143 A | 12/1974 | Simon et al. |
| 4,661,101 A | 4/1987 | Sustmann |

(Continued)

FOREIGN PATENT DOCUMENTS

| | | |
|---|---|---|
| EP | 0 685 213 B1 | 10/2001 |
| GB | 1 236 348 A | 6/1971 |

(Continued)

OTHER PUBLICATIONS

Co-pending U.S. Appl. No. 14/137,797, filed Dec. 20, 2013, by Romzek et al. for "Vaginal Insert Method of Manufacture."

*Primary Examiner* — Michelle Lopez
*Assistant Examiner* — Chinyere Rushing-Tucker
(74) *Attorney, Agent, or Firm* — Kimberly-Clark Worldwide, Inc.

(57) ABSTRACT

A method of manufacture for a vaginal insert. The vaginal insert may have a core, a cover, and a removal element. In various embodiments, the cover can be conformed to the vaginal insert.

3 Claims, 50 Drawing Sheets

(56) References Cited

U.S. PATENT DOCUMENTS

| | | | |
|---|---|---|---|
| 4,743,237 A | 5/1988 | Sweere | |
| 4,775,377 A | 10/1988 | Sweere | |
| 4,951,368 A | 8/1990 | Heinen | |
| 5,084,038 A | 1/1992 | Sheldon et al. | |
| 5,185,010 A | 2/1993 | Brown, Jr. | |
| 5,269,321 A | 12/1993 | MacDonald et al. | |
| 5,618,256 A | 4/1997 | Reimer | |
| 5,659,934 A | 8/1997 | Jessup et al. | |
| 5,671,755 A | 9/1997 | Simon et al. | |
| 5,755,906 A | 5/1998 | Achter et al. | |
| 5,785,640 A | 7/1998 | Kresch et al. | |
| 5,795,346 A | 8/1998 | Achter et al. | |
| 5,827,256 A | 10/1998 | Balzar | |
| 5,891,123 A | 4/1999 | Balzar | |
| D415,565 S | 10/1999 | Hayes et al. | |
| 5,964,689 A | 10/1999 | McFall et al. | |
| 6,039,716 A | 3/2000 | Jessup et al. | |
| 6,090,038 A | 7/2000 | Zunker et al. | |
| 6,090,098 A | 7/2000 | Zunker et al. | |
| 6,142,928 A | 11/2000 | Zunker et al. | |
| 6,358,235 B1 | 3/2002 | Osborn, III et al. | |
| 6,415,484 B1 | 7/2002 | Moser | |
| 6,418,930 B1 | 7/2002 | Fowler | |
| 6,460,542 B1 | 10/2002 | James | |
| 6,585,300 B1 | 7/2003 | Rajala et al. | |
| 6,595,974 B1 | 7/2003 | Pauley et al. | |
| 6,645,136 B1 * | 11/2003 | Zunker | A61F 2/005 128/885 |
| 6,679,831 B1 | 1/2004 | Zunker et al. | |
| 6,739,340 B1 | 5/2004 | Jensen et al. | |
| 6,758,839 B2 | 7/2004 | Lochte et al. | |
| 6,786,883 B2 | 9/2004 | Shippert | |
| 6,923,789 B2 | 8/2005 | Lemay et al. | |
| 6,969,380 B1 | 11/2005 | Zunker | |
| 7,011,033 B2 | 3/2006 | Sargent, Jr. et al. | |
| 7,044,928 B2 | 5/2006 | Lemay et al. | |
| 7,160,279 B2 | 1/2007 | Pauley et al. | |
| 7,214,219 B2 | 5/2007 | Intravartolo et al. | |
| 7,263,999 B2 | 9/2007 | Kaseki et al. | |
| D559,983 S | 1/2008 | Edgett et al. | |
| 7,401,450 B2 | 7/2008 | Lohrey et al. | |
| D579,113 S | 10/2008 | Edgett et al. | |
| 7,713,253 B2 | 5/2010 | Osborn, III et al. | |
| 7,717,892 B2 | 5/2010 | Bartning et al. | |
| 7,771,344 B2 | 8/2010 | Ziv | |
| 7,780,892 B2 | 8/2010 | Miller et al. | |
| 7,861,494 B2 | 1/2011 | Binner | |
| 7,892,163 B2 | 2/2011 | Bartning et al. | |
| 7,935,098 B2 | 5/2011 | Bartning et al. | |
| 7,959,193 B2 | 6/2011 | Ng | |
| 8,029,456 B2 | 10/2011 | Fung | |
| 8,047,980 B2 | 11/2011 | Bartning et al. | |
| 8,062,245 B2 | 11/2011 | Gann et al. | |
| 8,075,512 B2 | 12/2011 | Sargent, Jr. et al. | |
| 8,177,706 B2 | 5/2012 | Bartning et al. | |
| 8,221,374 B2 | 7/2012 | Hou et al. | |
| 8,221,375 B2 | 7/2012 | Lemay et al. | |
| 8,302,608 B2 | 11/2012 | Harmanli | |
| D675,733 S | 2/2013 | Karapasha et al. | |
| 8,435,168 B2 | 5/2013 | Ziv et al. | |
| 8,444,590 B2 | 5/2013 | Lemay et al. | |
| 8,449,446 B2 | 5/2013 | Ziv et al. | |
| 8,449,492 B2 | 5/2013 | Sargent, Jr. et al. | |
| 8,474,114 B2 | 7/2013 | Rolli | |
| 8,585,668 B2 | 11/2013 | Pauley et al. | |
| 8,608,639 B2 | 12/2013 | Bartning et al. | |
| 8,613,698 B2 | 12/2013 | Bartning et al. | |
| 8,617,047 B2 | 12/2013 | Sinai et al. | |
| 2002/0120246 A1 | 8/2002 | Buzot | |
| 2002/0143303 A1 | 10/2002 | Intravartolo et al. | |
| 2003/0093049 A1 | 5/2003 | Johnson et al. | |
| 2003/0114823 A1 | 6/2003 | Bosselaar et al. | |
| 2004/0087924 A1 | 5/2004 | Sroda et al. | |
| 2004/0122285 A1 | 6/2004 | Zunker | |
| 2004/0158122 A1 | 8/2004 | Guerquin | |
| 2004/0167491 A1 | 8/2004 | Mizutani | |
| 2004/0225272 A1 | 11/2004 | Karapasha et al. | |
| 2007/0244352 A1 | 10/2007 | Ziv | |
| 2008/0009814 A1 | 1/2008 | Bartning et al. | |
| 2008/0009931 A1 | 1/2008 | Bartning et al. | |
| 2008/0033230 A1 | 2/2008 | Bartning et al. | |
| 2008/0097366 A1 | 4/2008 | Mathews | |
| 2008/0149109 A1 | 6/2008 | Ziv | |
| 2008/0167598 A1 | 7/2008 | Gann et al. | |
| 2008/0167599 A1 | 7/2008 | Osborn et al. | |
| 2008/0214984 A1 | 9/2008 | Caracci et al. | |
| 2008/0281149 A1 * | 11/2008 | Sinai | A61F 2/005 600/32 |
| 2009/0247815 A1 | 10/2009 | Hou et al. | |
| 2009/0266367 A1 | 10/2009 | Ziv et al. | |
| 2010/0130954 A1 | 5/2010 | Handel et al. | |
| 2010/0197997 A1 | 8/2010 | Hou et al. | |
| 2010/0217068 A1 | 8/2010 | Ziv et al. | |
| 2010/0305395 A1 | 12/2010 | Spitz et al. | |
| 2011/0040234 A1 | 2/2011 | Chaffringeon | |
| 2011/0077578 A1 | 3/2011 | Bartning et al. | |
| 2011/0105830 A1 | 5/2011 | Hou et al. | |
| 2011/0152604 A1 | 6/2011 | Hull, Jr. et al. | |
| 2011/0160525 A1 | 6/2011 | Zunker et al. | |
| 2011/0160526 A1 * | 6/2011 | Zunker | A61F 2/005 600/29 |
| 2012/0101467 A1 | 4/2012 | Watanabe et al. | |
| 2012/0109095 A1 | 5/2012 | Middelbeek et al. | |
| 2012/0136199 A1 | 5/2012 | Hou et al. | |
| 2012/0259159 A1 | 10/2012 | Karapasha | |
| 2012/0259160 A1 | 10/2012 | Karapasha | |
| 2012/0259161 A1 | 10/2012 | Karapasha | |
| 2012/0259162 A1 | 10/2012 | Karapasha | |
| 2012/0259163 A1 | 10/2012 | Karapasha | |
| 2012/0259164 A1 | 10/2012 | Karapasha | |
| 2012/0259165 A1 | 10/2012 | Karapasha | |
| 2012/0259166 A1 | 10/2012 | Karapasha | |
| 2012/0259167 A1 | 10/2012 | Karapasha et al. | |
| 2012/0271098 A1 * | 10/2012 | Ziv | A61F 2/005 600/29 |
| 2012/0271099 A1 | 10/2012 | Ziv et al. | |
| 2013/0138071 A1 | 5/2013 | Fung et al. | |
| 2013/0158340 A1 | 6/2013 | Altan et al. | |
| 2013/0160272 A1 | 6/2013 | Bartning et al. | |
| 2013/0165742 A1 | 6/2013 | Bartning et al. | |
| 2013/0165743 A1 | 6/2013 | Ziv et al. | |
| 2013/0165843 A1 | 6/2013 | Hou et al. | |
| 2013/0211185 A1 | 8/2013 | Hull, Jr. et al. | |
| 2014/0000086 A1 * | 1/2014 | Avery, Jr. | A61F 2/005 29/428 |
| 2014/0000628 A1 | 1/2014 | Avery, Jr. et al. | |
| 2014/0000629 A1 | 1/2014 | Durling et al. | |
| 2014/0039245 A1 | 2/2014 | Ziv | |
| 2015/0173875 A1 | 6/2015 | Romzek et al. | |
| 2015/0173876 A1 * | 6/2015 | Romzek | A61F 2/0022 53/413 |
| 2015/0173879 A1 | 6/2015 | Adler et al. | |

FOREIGN PATENT DOCUMENTS

| | | |
|---|---|---|
| GB | 2 291 374 A | 1/1996 |
| WO | WO 2008/010214 A2 | 1/2008 |
| WO | WO 2009/081097 A1 | 7/2009 |
| WO | WO 2012/127877 A1 | 9/2012 |
| WO | WO 2012/167030 A1 | 12/2012 |
| WO | DM078518 | 1/2013 |

* cited by examiner

|  | SIZE 1 | SIZE 2 | SIZE 3 | SIZE 4 |
|---|---|---|---|---|
| HORIZONTAL ROTATION (Lt/Rt) | +/-17 | +/-20 | +/-22 | +/-25 |
| MEDIAL DEFLECTION | +0-24 | +0-29 | +0-34 | +0-38 |

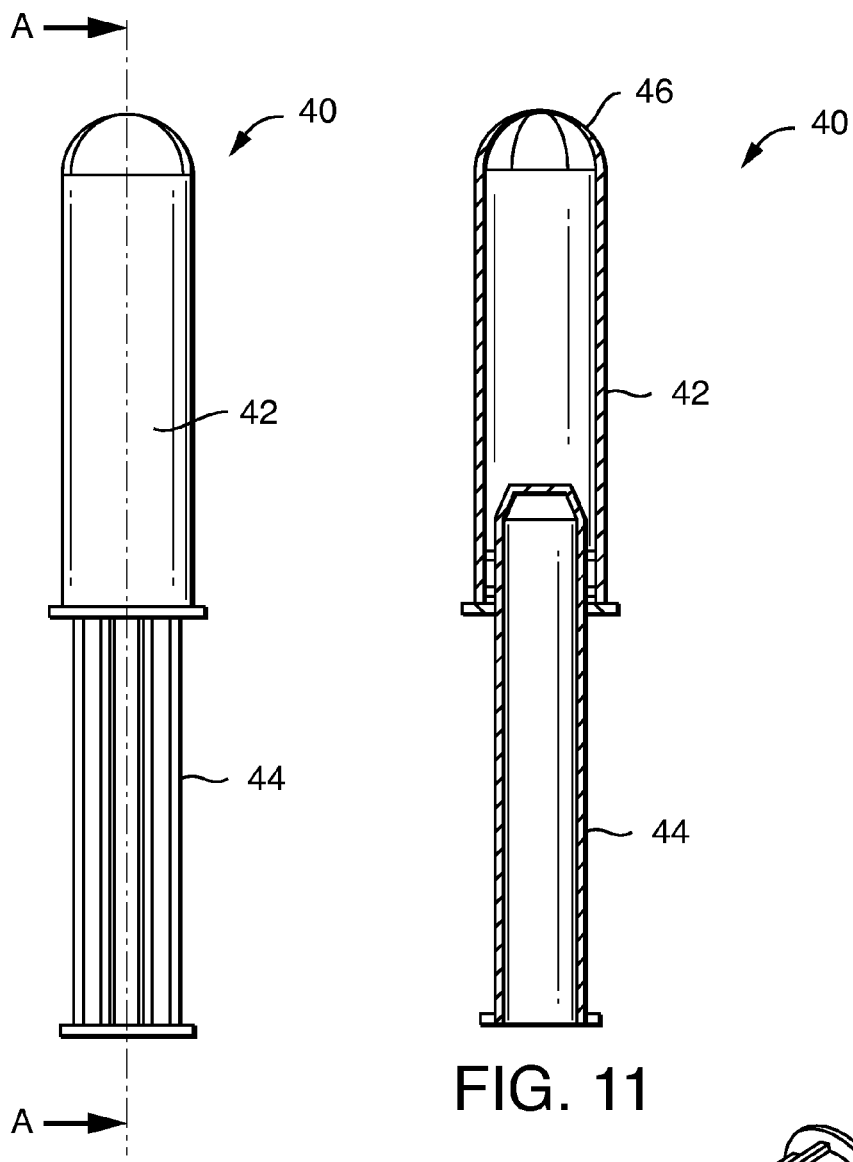
FIG. 10
FIG. 11
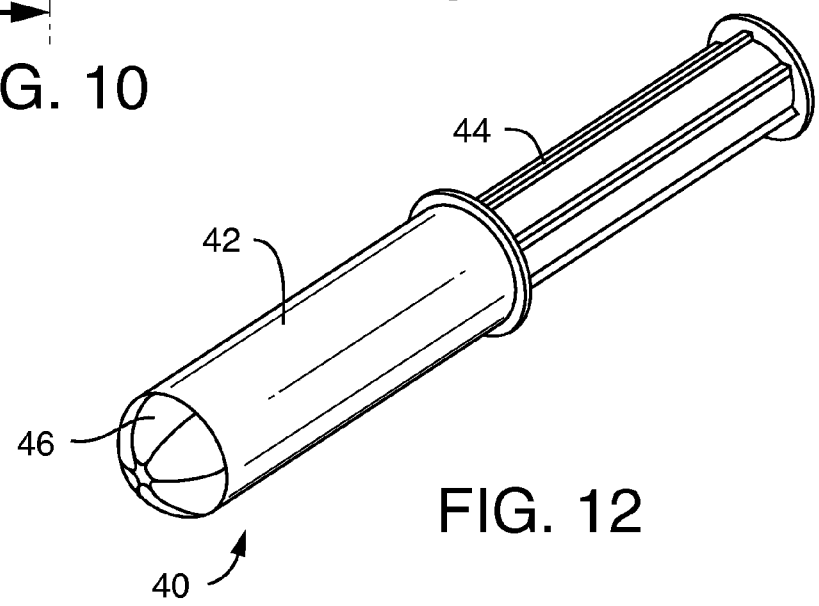
FIG. 12

| CORE DIMENSIONS | | | | | | | |
|---|---|---|---|---|---|---|---|
| | DIAMETER OF ANCHORING ELEMENT [mm] | | DIAMETER OF SUPPORTING ELEMENT [mm] | | CORE LENGTH [mm] | | WEIGHT [gr] |
| SIZE | | | | | | | |
| SIZE-1 | 30.8 | 32.8 | 35 | 37 | 42.3 | 44.3 | 5.9 | 6.3 |
| SIZE-2 | 30.8 | 32.8 | 40 | 42 | 40.7 | 42.7 | 5.9 | 6.3 |
| SIZE-3 | 30.8 | 32.8 | 45 | 47 | 38.5 | 40.5 | 5.9 | 6.3 |
| SIZE-4 | 30.8 | 32.8 | 49 | 51 | 36.7 | 39 | 5.9 | 6.3 |

FIG. 14A

| | PULLING STRING LENGTH [cm] | DIAMETER OF SUPPORTING ELEMENT | | |
|---|---|---|---|---|
| | | [mm] | ± TOLERANCE [mm] | [mm] |
| 1 | 12-16 | 34 | 35.75±1.75 | 37.5 |
| 2 | 12-16 | 38 | 39.5±1.5 | 41 |
| 3 | 12-16 | 43.5 | 45.0±1.5 | 46.5 |
| 4 | 12-16 | 47.5 | 49.0±1.5 | 50.5 |

FIG. 14B

| MATERIAL | S70 | | | S50 | | | S40 | | |
|---|---|---|---|---|---|---|---|---|---|
| SLOPE | MIN | MID | MAX | MIN | MID | MAX | MIN | MID | MAX |
| SIZE 1 | 6.90 | 7.70 | 8.50 | 2.80 | 3.15 | 3.50 | 2.20 | 2.50 | 2.80 |
| SIZE 2 | 6.30 | 7.10 | 7.90 | 2.80 | 3.15 | 3.50 | 2.20 | 2.50 | 2.80 |
| SIZE 3 | 5.60 | 6.15 | 6.70 | 2.50 | 2.75 | 3.00 | 1.60 | 1.90 | 2.20 |
| SIZE 4 | 5.00 | 5.85 | 6.70 | 2.50 | 2.75 | 3.00 | 1.60 | 1.90 | 2.20 |

FIG. 14C

| SIZE | MATERIAL | NOMINAL DIAMETER | SLOPE | MINIMAL DIAMETER | MAX FORCE |
|---|---|---|---|---|---|
| 1 | S40 | 36 | 2.5 | 12.0 | 60.0 |
| 2 |  | 41 | 2.5 | 12.0 | 72.5 |
| 3 |  | 46 | 1.9 | 12.0 | 64.6 |
| 4 |  | 50 | 1.9 | 12.0 | 72.2 |
| 1 | S50 | 36 | 3.15 | 12.0 | 75.6 |
| 2 |  | 41 | 3.15 | 12.0 | 91.4 |
| 3 |  | 46 | 2.75 | 12.0 | 93.5 |
| 4 |  | 50 | 2.75 | 12.0 | 104.5 |
| 1 | S70 | 36 | 7.7 | 12.0 | 184.8 |
| 2 |  | 41 | 7.1 | 12.0 | 205.9 |
| 3 |  | 46 | 6.15 | 12.0 | 209.1 |
| 4 |  | 50 | 5.85 | 12.0 | 222.3 |

FIG. 16

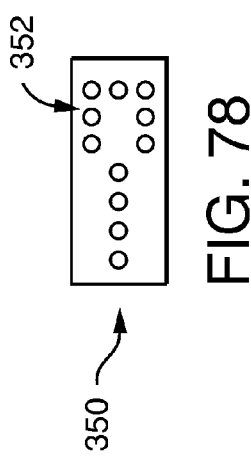
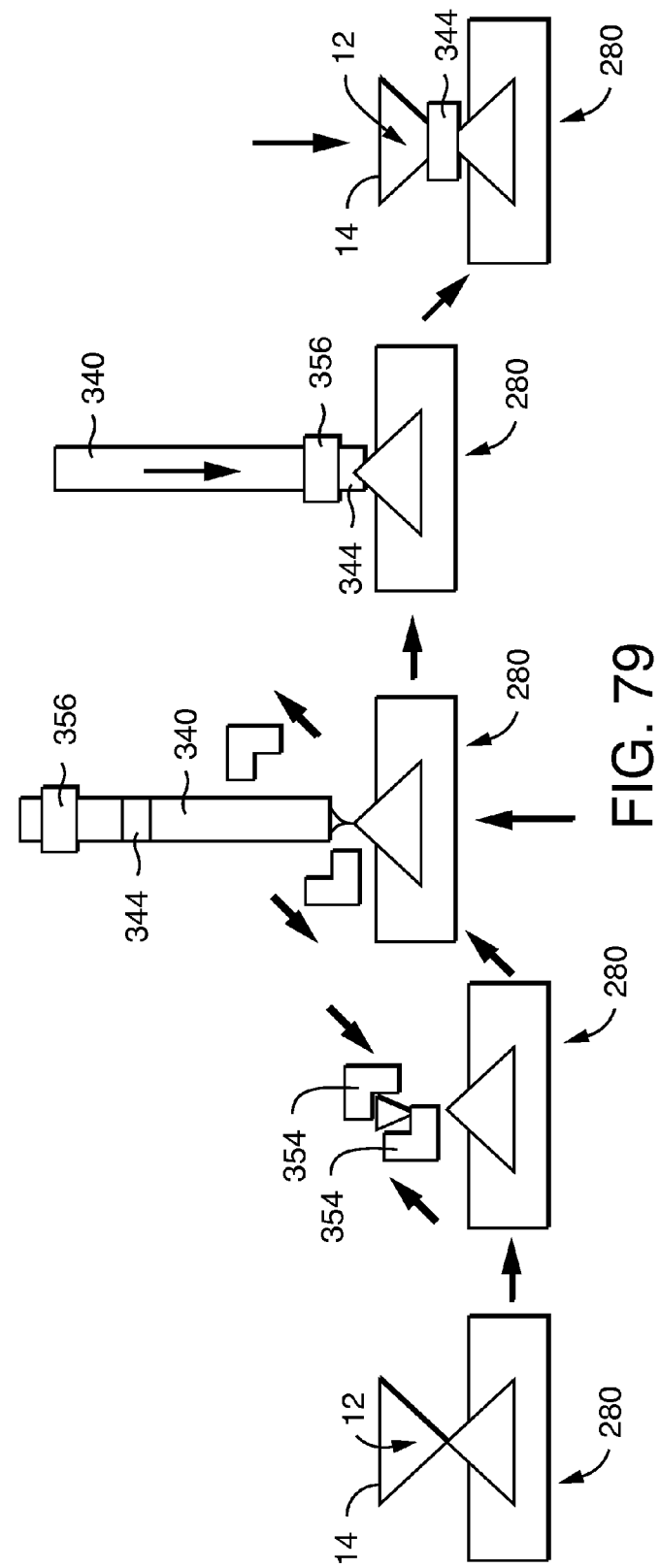

VAGINAL INSERT METHOD OF MANUFACTURE

BACKGROUND

Urinary incontinence is a problem among females. It is estimated that up to 50% of women occasionally leak urine involuntarily and that approximately 25% of women will seek medical advice in order to deal with the problem. Stress incontinence, the most common type of urinary incontinence, refers to the involuntary leakage of urine resulting from a rise in abdominal pressure. When involuntary urination occurs, it often happens because of a rise in pressure in the bladder for which there is no compensating counterpressure from the bladder neck or urethra. This is usually the result of the abnormal descent of the bladder neck and the urethra into a low position and away from the intra-abdominal pressure system. Known as "hypermobility", this can be the result of some injury to the support mechanism which normally keeps the urethra and the bladder neck in a raised position along the backside of the pubic bone.

The lowering of the bladder neck and the urethra that occur, for example, when a woman coughs, sneezes, or laughs, can cause involuntary leakage of urine. While many different factors may contribute to the development of stress incontinence, it is most prevalent among women ages 35-65 and those who have had multiple vaginal deliveries.

Stress incontinence is both aggravating and unpleasant for women and it can also be embarrassing. Many women wear sanitary pads in order to deal with stress incontinence although this is not a real solution to the problem and it can be very inconvenient and unreliable. Surgical treatment may involve, among other things, elevation of the anterior vaginal wall (Anterior Colporrhaphy), securing the paraurethal tissue to the periosteum of the pubic bone (Marshall-Marchetti-Krantz operation), or elevation of the paracervical vaginal anterior wall to the Coopers ligament (Burch Colpo suspension) in order to elevate the bladder neck above the level of the pelvic floor and thereby distribute pressure equally to the bladder, the bladder neck, and the mid-urethra. Recently, a procedure known as "TVT" (Tension Free Vaginal Tape) was developed in which a mesh tape is implanted underneath the urethra (usually mid-urethra) creating a hammock on which the urethra may kink during a rise in intra-abdominal pressure. However, surgery is only suitable for severe cases and the majority of women experiencing stress incontinence does not need, and certainly would rather avoid, surgical solutions.

One non-surgical treatment involves the use of vaginal inserts that are inserted into the vagina either by a medical practitioner or by the woman herself. Most vaginal inserts are designed to apply pressure against the bladder neck so as to inhibit or completely block the flow of urine through the urethra. One problem with such devices is that they completely block the urethra and thus they need to be removed or collapsed in order to allow the woman to urinate. To overcome this drawback vaginal inserts have been developed having specialized shapes that do not completely block the urethra but these vaginal inserts tend to be large, uncomfortable, and intrusive. They also tend to cause irritation or soreness to the vagina.

Another common shortcoming is that most vaginal inserts also tend to be difficult, painful or uncomfortable to insert and/or remove. In order to correctly inhibit urine flow, the vaginal insert needs to be properly positioned in the vaginal canal. As a result, a doctor may be required to properly position the vaginal insert. In most cases, the vaginal insert is adapted for remaining in the vagina for a prolonged period of time (due to the time and expense of requiring a trained medical professional to insert the vaginal insert). However, when positioned in the vagina for an extended period of time, the vaginal insert may cause vaginal infections, pressure ulcers, and/or bleeding.

A vaginal insert for treating urinary incontinence should have a size and shape configuration such that it can be comfortable during the insertion and removal process. A vaginal insert for treating urinary incontinence also needs to be capable of expanding following insertion into the vagina and during wear in order to provide efficacious incontinence protection. There is a need for a vaginal insert for treating urinary incontinence which can be comfortable to wear in an at-rest state and which can provide incontinence prevention during a high stress event. There is a need for a method of manufacture of such a vaginal insert for treating urinary incontinence. There is a need for a method of manufacture for providing a vaginal insert which can have a size and shape configuration such that the vaginal insert can be comfortable during insertion, the vaginal insert can expand following insertion to provide urinary incontinence prevention, and the vaginal insert can be collapsed to allow for a comfortable removal of the vaginal insert from the vagina.

SUMMARY

A method of manufacturing a vaginal insert comprising the steps of providing a core, the core comprising an anchoring element; a supporting element; and a node connecting the anchoring element and the supporting element; providing a cover blank; inserting the core into the cover blank by inverting the cover blank over the core resulting in a core and cover blank combination; attaching a removal element to the cover blank; and converting the cover blank into a cover. In various embodiments, the cover blank comprises a first layer of material and a second layer of material in a face-to-face relationship with the first layer of material and a first side seam and a second side seam bonding the first layer of material to the second layer of material. In various embodiments, the cover blank comprises a rectangular, trapezoidal or trapezoid-like shape when viewed in a flat, two-dimensional configuration. In various embodiments, the method further comprises the step of forming a supporting element seam in the cover blank. In various embodiments, the supporting element seam of the cover blank can be located proximate the supporting element of the core. In various embodiments, the step of attaching the removal element to the cover blank further comprises the step of rotating the core and cover blank combination. In various embodiments, the method further comprises the step of conforming the cover to the core. In various embodiments, the step of conforming the cover to the core further comprises the step of attaching a band of material to the cover.

A method of manufacturing a vaginal insert comprising the steps of providing a core, the core comprising an anchoring element; a supporting element; and a node connecting the anchoring element and the supporting element; providing a cover blank, the cover blank comprising a first layer of material and a second layer of material in a face-to-face relationship with the first layer of material; and a first side seam and a second side seam bonding the first layer of material to the second layer of material; forming a supporting element seam in the cover blank; inverting the cover blank over the core to form a core and cover blank combination; attaching a removal element to the cover blank; and forming an anchoring element seam in the cover blank to convert the cover blank to a cover. In various embodiments, the cover blank comprises a rectangular, trapezoidal or trapezoid-like shape in a flat, two-dimensional configuration. In various embodiments, the step of attaching the removal element to the cover blank further comprises the step of rotating the core and cover blank combination. In various embodiments, the step of attaching the removal element to the cover blank further comprises the step of attaching the removal element in an area of the cover blank which does not contain a side seam of the cover blank. In various embodiments, the method further comprises the step of conforming the cover to the core. In various embodiments, the step of conforming the cover to the core further comprises the step of attaching a band of material to the cover.

A method of manufacturing a vaginal insert comprising the steps of providing a core; providing a cover blank, the cover blank comprising a first layer of material and a second layer of material in a face-to-face relationship with the first layer of material; a first side seam and a second side seam bonding the first layer of material to the second layer of material; top edges of the first layer of material and second layer of material in an unbonded configuration; and bottom edges of the first layer of material and the second layer of material in an unbonded configuration; pleating the bottom edges of the cover blank; forming a supporting element seam in the pleated bottom edges of the cover blank; inverting the cover blank over the core to form a core and cover blank combination; pleating the top edges of the cover blank; and forming an anchoring element seam in the pleated top edges of the cover blank to convert the cover blank to a cover. In various embodiments, the cover blank comprises a rectangular, trapezoidal, or trapezoid-like shape in a flat, two-dimensional configuration. In various embodiments, the method further comprises the step of attaching a removal element. In various embodiments, the step of attaching the removal element to the cover blank includes the step of rotating the core and cover blank combination. In various embodiments, the step of attaching the removal element to the cover blank further comprises the step of attaching the removal element in an area of the cover blank which does not contain a side seam of the cover blank. In various embodiments, the method further comprises the step of conforming the cover to the core.

A method of conforming a cover to a vaginal insert comprising the steps of providing a core, the core comprising an anchoring element; a supporting element; and a node connecting the anchoring element and the supporting element; providing a cover blank, the cover blank comprising a first layer of material and a second layer of material in a face-to-face relationship with the first layer of material; and a first side seam and a second side seam bonding the first layer of material to the second layer of material; inserting the core into the cover blank to form a core and cover blank combination; converting the cover blank to a cover; and conforming the cover to the core in the area of the node of the core. In various embodiments, the cover blank comprises a rectangular, trapezoidal or trapezoid-like shape in a flat, two-dimensional configuration. In various embodiments, the step of conforming the cover to the core further comprises the step of reducing the dimension of the cover at the node of the core. In various embodiments, the step of reducing the dimension of the cover can further include one of the following: wrapping a band of material around the cover, twisting a portion of the material forming the cover, applying a thermal treatment to the cover, or altering an elastic and/or extensible property of the cover. In various embodiments, the step of reducing the dimension of the cover can further comprise a step of wrapping a band of material around the cover at the node of the core. In various embodiments, the method further comprises the step of compressing the anchoring element of the core and sliding the band of material over the compressed anchoring element of the core. In various embodiments, the method further comprises the step of maintaining the reduced dimension of the cover.

A method of conforming a cover to a vaginal insert comprising the steps of providing a core, the core comprising an anchoring element; a supporting element; and a node connecting the anchoring element and the supporting element; providing a cover blank, the cover blank comprising a first layer of material and a second layer of material in a face-to-face relationship with the first layer of material; and a first side seam and a second side seam bonding the first layer of material to the second layer of material; inserting the core into the cover blank to create a core and cover blank combination; converting the cover blank to a cover; providing a band of material; encircling the band of material around the cover at the location of the node of the core; and attaching the band of material to the cover at the location of the node of the core. In various embodiments, the cover blank comprises a rectangular, trapezoidal or trapezoid-like shape in a flat, two-dimensional configuration. In various embodiments, the step of inserting the core into the cover blank further comprises the step of inverting the cover blank over the core. In various embodiments, the method further comprises the step of compressing the anchoring element of the core and sliding the band of material over the compressed anchoring element of the core.

A method of conforming a cover to a vaginal insert comprising the steps of providing a core, the core comprising a longitudinal axis; and symmetry about the longitudinal axis; providing a cover blank, the cover blank comprising a longitudinal axis; and symmetry about the longitudinal axis when viewed in a flat, two-dimensional configuration; inserting the core into the cover blank; converting the cover blank into a cover; conforming the cover to the core. In various embodiments, the core further comprises an anchoring element, a supporting element and a node connecting the anchoring element and the supporting element. In various embodiments, the cover blank further comprises a rectangular, trapezoidal or trapezoid-like shape. In various embodiments, the step of conforming the cover to the core further comprises the step of reducing the dimension of the cover at the node of the core. In various embodiments, the step of reducing the dimension of the cover can further include one of the following: wrapping a band of material around the cover, twisting a portion of the material forming the cover, applying a thermal treatment to the cover, or altering an elastic and/or extensible property of the cover. In various embodiments, the step of reducing the dimension of the cover can further comprise a step of wrapping a band of material around the cover at the node of the core. In various embodiments, the method further comprises the step of compressing the anchoring element of the core and sliding the band of material over the compressed anchoring element of the core. In various embodiments, the method further comprises step of maintaining the reduced dimension of the cover.

A method of conforming a cover to a core comprising the steps of providing a core; proving a cover blank; inserting the core within the cover blank; converting the cover blank into a cover; reducing a dimension of the cover; and maintaining the reduced dimension of the cover. In various embodiments, the dimension of the cover is reduced at a narrowest portion of the core. In various embodiments, the core comprises an anchoring element, a supporting element, and a node connecting the anchoring element and the supporting element. In various embodiments, the dimension of the cover is reduced at the node of the core. In various embodiments, the step of reducing the dimension of the cover can further include one of the following: wrapping a band of material around the cover, twisting a portion of a material forming the cover, applying a thermal treatment to the cover, or altering an elastic and/or extensible property of the cover. In various embodiments, the step of reducing the dimension of the cover can further comprise a step of wrapping a band of material around the cover. In various embodiments, the step of maintaining the reduced dimension of the cover can further include a step of attaching the band to the cover.

A core insertion module comprising a bottom level comprising a core compression tray; and a push rod positioned beneath the core compression tray; a top level comprising a second pallet table; and a pre-tuck rod positioned above the second pallet table; and a middle level between the bottom level and the top level and comprising a barrel drum. In various embodiments, the core compression tray comprises at least one opening for receiving a core therein. In various embodiments, the core compression tray comprises a pair of jaws which shift at a 45° angle relative to the core insertion module to compress a core loaded within the core compression tray. In various embodiments, the barrel drum is capable of rotating 180°. In various embodiments, the second pallet table further comprises a transfer tube.

A core insertion module comprising a bottom level comprising a core compression tray capable of transitioning from an open configuration to a closed configuration; and a push rod positioned beneath the core compression tray; a top level comprising a second pallet table capable of moving in an up and down movement; and a pre-tuck rod positioned above the second pallet table; and a middle level between the bottom level and the top level and comprising a barrel drum; and a core set tool. In various embodiments, the core compression tray comprises at least one opening for receiving a core therein. In various embodiments, the core compression tray comprises a pair of jaws which shift at a 45° angle relative to the core insertion module to compress a core loaded within the core compression tray. In various embodiments, the barrel drum is capable of rotating 180°. In various embodiments, the second pallet table further comprises a transfer tube.

A compression tray comprising a front jaw, a rear jaw, guide blocks, at least one opening for receiving an item to be compressed, and a pair of spaced jaw connection mechanisms connecting the front and rear jaw. In various embodiments, the front jaw and the rear jaw shift at a 45° angle to compress a core loaded within the compression tray. In various embodiments, the front jaw and the rear jaw shift with respect to each other and maintain an aspect ratio of the opening of the compression tray. In various embodiments, the jaw connection mechanisms can be one of rack and pinion arrangements, slides, guide rails, or linear bearings.

A string and knot module comprising a stringing module comprising a string block; a string block clamp located internal to the string block; a needle; a string pulling clamp mechanism; and a string clamp associated with the string pulling clamp mechanism; a knotting module comprising an upper knotting block; a lower knotting block; and a first funnel and a second funnel, each of the first and second funnels associated with the lower knotting block. In various embodiments, the stringing module further comprises a source providing an air pressure differential. In various embodiments, the stringing module further comprises a scissor assembly. In various embodiments, the knotting module upper knotting block further comprises an upper portion, a lower portion and a center pin positioned within the upper portion of the upper knotting block. In various embodiments, the upper and lower portions of the upper knotting block can move independently of each other. In various embodiments, the knotting module lower knotting block further comprises an upper portion, a lower portion and a center pin positioned within the upper portion of the lower knotting block. In various embodiments, the upper and lower portions of the lower knotting block can move independently of each other. In various embodiments, the knotting module further comprises a string path associated with the lower and upper portions of the lower knotting block and the lower and upper portions of the upper knotting block. In various embodiments, a portion of the string path associated with the upper knotting block is at a 90° angle relative to a portion of the string path associated with the lower knotting block.

A string and knot module comprising a stringing module comprising a string block; a string block clamp located internal to the string block; a needle; a string pulling clamp mechanism; a string clamp associated with the string pulling clamp mechanism; and a pair of cover blank clamps; a knotting module comprising an upper knotting block; a lower knotting block; a first funnel and a second funnel, each of the first funnel and second funnels associated with the lower knotting block; and a string pincher. In various embodiments, the stringing module further comprises a source providing an air pressure differential. In various embodiments, the stringing module further comprises a scissor assembly. In various embodiments, the upper and lower portions of the upper knotting block can move independently of each other. In various embodiments, the upper and lower portions of the lower knotting block can move independently of each other. In various embodiments, the knotting module further comprises a string path associated with the lower and upper portions of the lower knotting block and the lower and upper portions of the upper knotting block. In various embodiments, a portion of the string path associated with the upper knotting block is at a 90° angle relative to a portion of the string path associated with the lower knotting block.

A knot module comprising an upper knotting block comprising an upper portion; a lower portion; a center pin positioned within the upper portion of the upper knotting block; a lower knotting block comprising an upper portion; a lower portion; a center pin positioned within the upper portion of the lower knotting block; a string path associated with the lower and upper portions of the lower knotting block and associated with the lower and upper portions of the upper knotting block. In various embodiments, the upper portion and the lower portion of the upper knotting block can move independently of each other. In various embodiments, the upper portion and the lower portion of the lower knotting block can move independently of each other. In various embodiments, a portion of the string path associated with the upper knotting block is at a 90° angle relative to the a portion of the string path associated with the lower knotting block.

A band forming module comprising a first web guide; a pair of feed rollers; a second web guide; a scissor mechanism; and a mandrel. In various embodiments, the mandrel is capable of rotation of 360°. In various embodiments, the mandrel comprises at least one end which is hollow. In various embodiments, the mandrel is connected to a vacuum. In various embodiments, the mandrel comprises a vacuum hole pattern thereon. In various embodiments, the band forming module further comprises a servo motor for driving at least one of the feed rollers. In various embodiments, the band forming module further comprises a bonding mechanism.

A band forming module comprising a first web guide; a pair of feed rollers; a second web guide; a compressed air supply source; a scissor mechanism; and a mandrel. In various embodiments, the mandrel is capable of rotation of 360°. In various embodiments, the mandrel comprises at least one end which is hollow. In various embodiments, the mandrel is connected to a vacuum. In various embodiments, the mandrel comprises a vacuum hole pattern thereon. In various embodiments, the band forming module further comprises a servo motor for driving at least one of the feed rollers. In various embodiments, the band forming module further comprises a bonding mechanism.

BRIEF DESCRIPTION OF THE DRAWINGS

FIG. 10 is a perspective view of an exemplary embodiment of an applicator for a vaginal insert.

FIG. 11 is a cross-sectional view of the applicator of FIG. 10.

FIG. 12 is a perspective view of the applicator of FIG. 10.

FIGS. 14A-14C are a series of charts illustrating exemplary core specifications.

FIG. 16 is a table showing performance characteristics for exemplary basic core configurations.

FIG. 78 is a schematic illustration of an exemplary pattern of vacuum holes on a mandrel.

FIG. 79 is a schematic illustration of an exemplary process of arranging a band on a cover.

DETAILED DESCRIPTION

Figure 1:
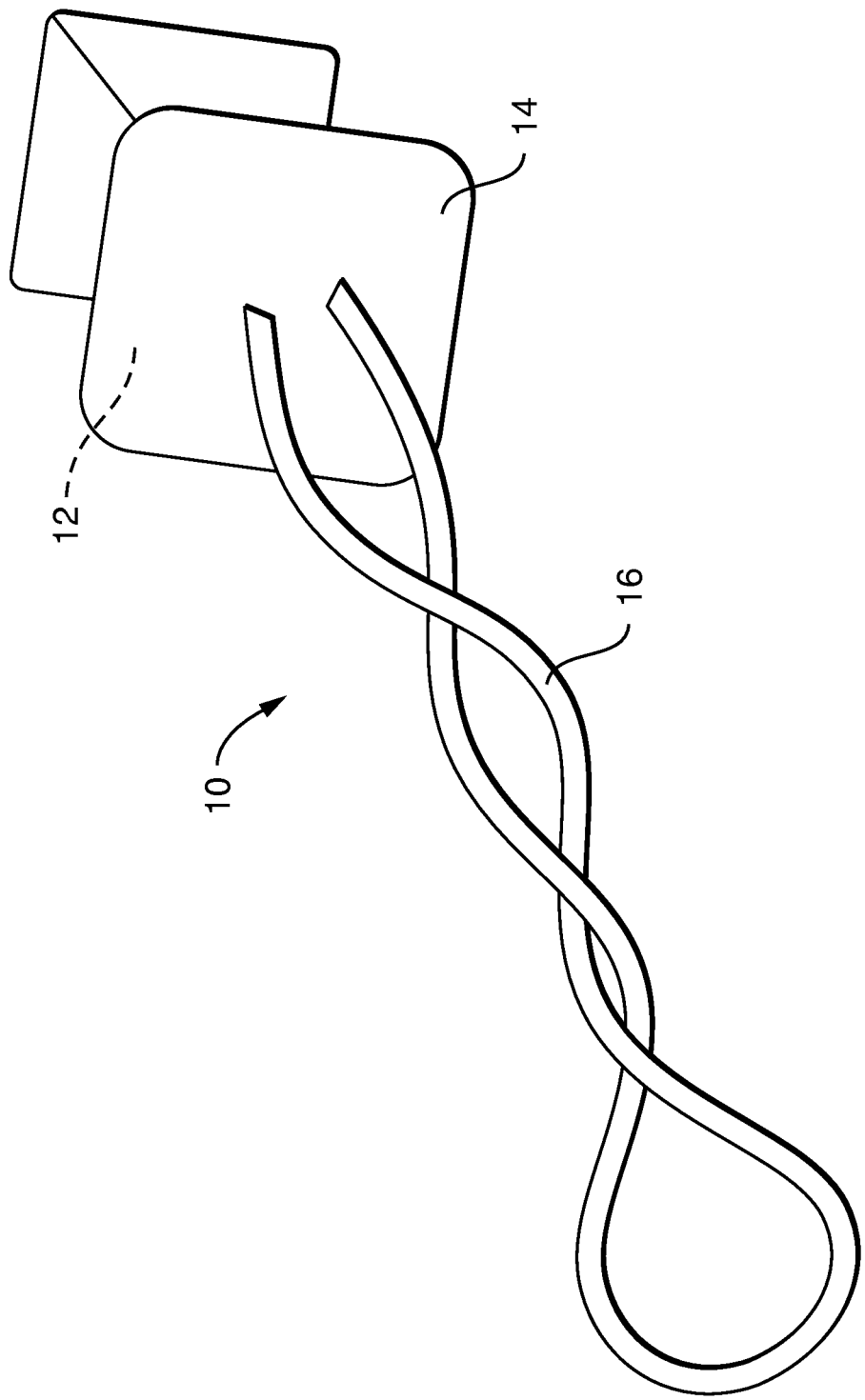
FIG. 1 is a perspective view of an exemplary embodiment of a vaginal insert.

The present disclosure is generally directed towards a method of manufacturing a vaginal insert for the treatment of urinary incontinence in females. The vaginal insert can provide tension-free incontinence treating support perpendicularly to the urethra (i.e., across the urethra). It should also be noted that for some women, the described vaginal inserts can also be used as a treatment or part of a treatment for prolapse.

Vaginal Insert:

In various embodiments, the vaginal insert can be adapted to be stable in the vagina without significant longitudinal and/or rotational movement within the vagina. For example, supporting and anchoring arms of the vaginal insert can be designed to resist longitudinal movement within the vagina. As another example, the tips of the supporting and/or anchoring arms can be designed to resist rotational motion by working with the natural behavior of the vaginal wall, for example, by being sized and/or shaped to induce the vaginal wall to at least partially envelope the tip, thereby preventing rotational movement. Stability can also be enhanced by using the supporting and/or anchoring arms to provide contact between the vaginal insert and multiple points located spatially around the vaginal insert on the vaginal wall. In an embodiment, proper support-rendering positioning of the vaginal insert can be considered to be where two supporting arms position themselves one on each side of the urethra while at least one other supporting arm provides opposing force to the vaginal insert when the two supporting arms are subjected to force from the urethra during high-stress events that cause the urethra to drop in the vagina.

In various embodiments, the vaginal insert can be adapted to be disposable, worn only for a relatively short period of time and then discarded and replaced with a new vaginal insert (if needed). Alternatively, the vaginal insert can be recycled for use by sterilizing it between uses. The vaginal insert can be simple and easy to use and can, optionally, be inserted in the same user-friendly manner that a tampon is inserted into the vagina during menstruation, for example by using an applicator. In an embodiment, the vaginal insert can be inserted in any orientation since the vaginal insert can naturally migrate into a correct treatment position as a result of the vaginal insert geometry. The vaginal insert can be small, exemplary sizes described below, comfortable, and once inserted, the woman need not think about it again until it is removed. As with insertion, removal can be accomplished in a similar manner as a tampon, such as by pulling on a removal element.

In various embodiments, the vaginal insert can include a core and a removal element. In various embodiments, the vaginal insert can include a core, a cover, and a removal element. Each of these components will be described in more detail below. An example of a vaginal insert 10 having a core 12, a cover 14, and a removal element 16 can be seen in FIG. 1.

Figure 2:
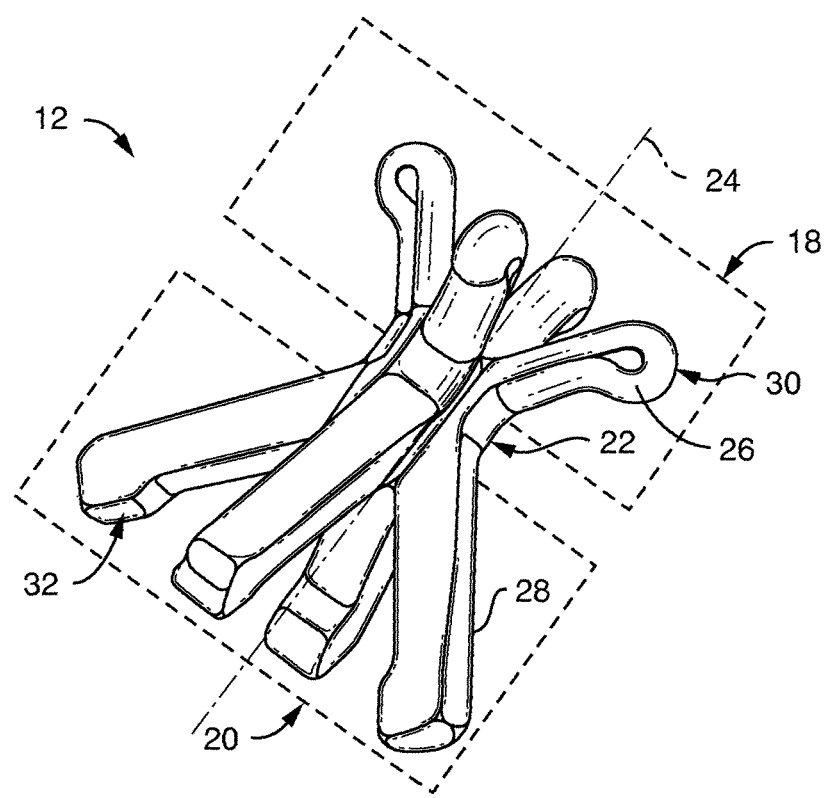
FIGS. 2-3 are perspective views of exemplary embodiments of a core.

Referring to FIG. 2, a perspective view of an exemplary embodiment of a core 12 for a vaginal insert 10 for treating urinary incontinence is illustrated. For ease of description, the core 12 can be arranged around a longitudinal axis 24 and divided into three basic elements. A top section 18, inside the dashed box, can be provided which can serve as the "anchoring" element for stabilizing the vaginal insert 10 within the vagina. There can be at least one of three types of anchoring: axial anchoring which can act in the direction along the central axis of the vagina, radial anchoring which can act side-to-side or substantially perpendicular to the central axis of the vagina and/or rotational anchoring which will be described in more detail below. In an embodiment, the anchoring element 18 does not apply significant pressure to the wearer's vagina and/or urethra, which can thereby result in enhanced comfort. A bottom section 20, inside the dashed box, can be provided which can serve as the "supporting" element for generating support. In various embodiments, support can be generated at a sub-urethral location, for example mid-urethra. Alternatively, additionally, and/or optionally, support can be generated at the bladder neck. In various embodiments, the supporting element 20 can provide at least one type of anchoring, described above, to help anchor the vaginal insert 10 in position within the vagina. In various embodiments, the roles of anchoring 18 and supporting 20 elements can be switched or shared. In an embodiment, the anchoring 18 and supporting 20 elements of the core 12 can function as an internal support structure for a cover 14.

In an embodiment, an intermediate section can be provided which can act as a "node" 22 and which can connect anchoring 18 and supporting 20 elements. The node 22 of core 12 can have a length which can be a small portion of the overall length of the core 12. In various embodiments, the length of the node 22 can be less than about 15, 20 or 30% of the entire length of the core 12. In various embodiments, a node 22 having a short length relative to the entire length of the core 12 can allow for more flexibility in varying the stiffness, the comfort, and the size of the core 12 when compared with a same length core 12 with a longer node 22.

Various design aspects of the core 12 can encourage stability of the vaginal insert 10 in the vagina, including: the longitudinal design of the core 12 which can incorporate anchoring arms 26 adapted to prevent movement of the vaginal insert 10 deeper into the vagina and/or supporting arms 28 adapted to prevent movement of the vaginal insert 10 towards the entrance to the vagina; specially adapted arm tips, such as tips 30 and 32, which can resist rotational movement of the vaginal insert 10 as they can be at least partially enveloped by the vaginal wall; an overall design which can take advantage of the vaginal tenting phenomenon; and, a multi-dimensional aspect which can allow various arms, 26 and/or 28, of the core 12 to contact multiple and/or opposing vaginal surfaces concurrently.

In an exemplary embodiment, the anchoring element 18 and the supporting element 20 can each have four arms, 26 and 28, respectively. In such an exemplary embodiment, two arms, 26 and 28, of each of the anchoring 18 and supporting 20 elements, respectively, can generally exert pressure towards the anterior vaginal wall and two arms, 26 and 28, of each of the anchoring 18 and supporting 20 elements, respectively, can generally exert pressure towards the posterior vaginal wall adjacent the bowels. The distal part of the urethra extends into the vagina forming a recess between the urethral bulge and the vaginal wall. The arms, 26 and/or 28, which exert pressure anteriorly can fit within these natural recesses on either side of the urethra. In various embodiments, the anchoring element 18 and the supporting element 20 can each have more or less arms, 26 and 28, respectively. For example, the anchoring element 18 could have more anchoring arms 26 if there is concern about unwanted movement of the vaginal insert 10.

Supporting arms 28 can cause elevation of the tissues around the urethra, optionally mid-urethra and/or bladder neck thereby acting as a hammock. This hammock can support the urethra in a tension free manner. In a woman who leaks urine during a stress event (e.g., when abdominal pressure rises during coughing, sneezing, etc.), the urethra sags down but meets the hammock in its mid-part. The meeting of the urethra and the hammock can cause an elevation of the intra-urethral pressure with resultant urinary continence.

In an embodiment, anchoring arms 26 can force the vaginal insert 10 to remain in situ within the vagina, unable to substantially move inwards or outwards of the vagina, or to rotate within the vagina. One reason that this can occur can be as a result of the tendency of vaginal walls to collapse and form an occluded lumen. The arms, 26 and/or 28, of the core 12 can cause "tenting" of the vaginal walls on top of the arms with resultant sagging of the vaginal walls around the core 12, which can thereby stabilize the core 12. Additionally, in various embodiments, anchoring arms 26 can be flexible and/or elastic and/or resilient. This flexibility can enhance the anchoring arms 26 ability to prevent motion of the vaginal insert 10 further into the vagina. As force strives to exert itself on the vaginal insert 10 and move the vaginal insert 10 further into the vagina, the flexible anchoring arms 26 can tend to spread apart. This spreading action of the anchoring arms 26 can increase the friction between the vaginal insert 10 and the vaginal wall, thereby preventing movement further into the vagina. While the anchoring arms 26 can be flexible, it should be noted that they can be rigid enough and/or can be configured to spread to prevent unwanted motion of the vaginal insert 10 towards the entrance of the vagina. In an embodiment, the anchoring arms 26 can be rigid but the node 22 can be flexible allowing the node 22 to provide flexible anchoring support. Movement towards the vaginal opening can also be resisted by the supporting arms 28 which tend to widen radially when pulled outwardly. These features work with the tenting behavior of the vaginal walls which also helps to maintain the vaginal device 10 in place.

Figure 3:
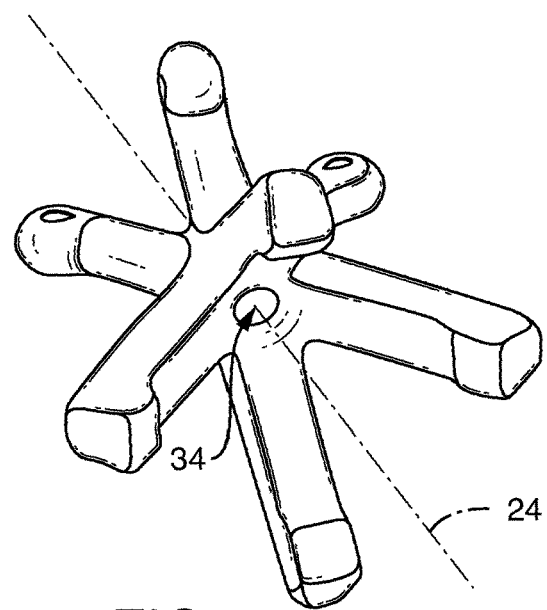
Figure 4:
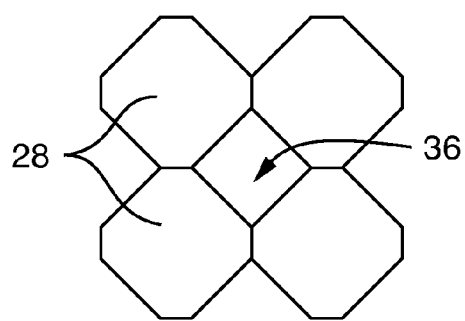
FIGS. 4-6 are cross-sectional views of exemplary embodiments of the supporting arms of a core.
Figure 5:
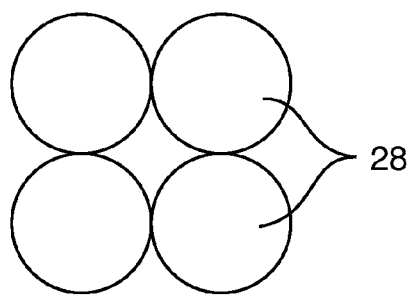
Figure 6:
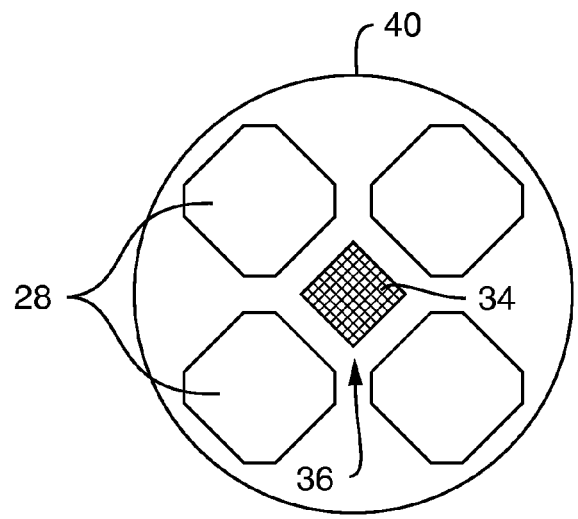

Referring to FIG. 2, the anchoring arms 26 can have tips 30 and the supporting arms 28 can have tips 32. In various embodiments, the tips 30 of the anchoring arms 26 can be rounded or spherical in nature, to provide smooth surfaces (i.e., no corners or points) for the tenting of the vaginal wall. In various embodiments, the tips 32 of the supporting arms 28 and/or corners of core 12 can be blunted by a beveled edge both along the anchoring arms 26 and supporting arms 28 and at the tips 32, such as shown in FIGS. 2 and 3. In various embodiments, the tips 32 can be slightly rounded and/or have a beveled edge. In an embodiment, the beveled edge of the supporting arms 28 can reduce the overall circumference of the core 12, relative to a completely spherical cross section, when it is in a compressed mode for packaging within an applicator. The difference between a core 12 with a beveled cross-section and a core 12 with a spherical cross-section can be seen in FIGS. 4 and 5. FIG. 6 illustrates a vaginal insert with a beveled cross-section in an applicator 40.

Also illustrated in FIG. 3 is a channel 34 which can transect the core 12, whereby core 12 can be "held" during manufacturing and/or assembly of the core 12 by placing a rod through channel 34. In an embodiment, channel 34 can be circular in shape. In an embodiment, channel 34 can be quadrilateral shaped. As illustrated in FIG. 6, the channel 34 can be accessible through the quadrilateral shaped tunnel 36 created by the beveled edges of supporting arms 28 when compressed for packaging in an applicator 40. In an embodiment, channel 34 can be no bigger in circumference and/or dimension than tunnel 36.

Figure 7:
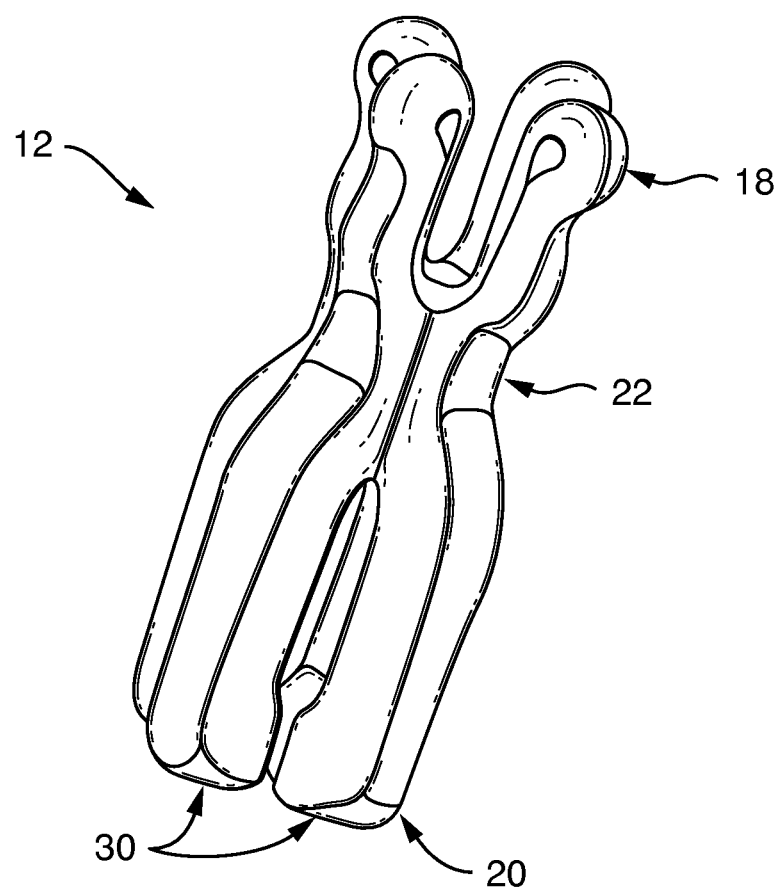
FIG. 7 is a perspective view of an exemplary embodiment of a core.

In various embodiments, cores 12 of all sizes can have arms, both anchoring 26 and supporting 28 arms, which can be the same length. In various embodiments, cores 12 of all sizes can have the same total length when completely compressed inwardly. An example of an inwardly compressed core 12 can be seen in FIG. 7. In an embodiment, anchoring arms 26 can be shorter than the supporting arms 28. In such an embodiment, the longitudinal length of the anchoring element 18 can be shorter than the longitudinal length of the supporting element 20 when the core 12 has been completely inwardly compressed. In such an embodiment, the node 22 is not necessarily located at the midpoint of the longitudinal axis 24. In such an embodiment, the core 12 may be symmetrical about the longitudinal axis 24, however, the core 12 is not necessarily symmetrical about a lateral axis which can be located at the midpoint of the longitudinal axis 24. In an embodiment, anchoring arms 26 can be a consistent size in a line-up of different sizes of cores 12 even though the supporting arms 28 may vary in size and/or performance. Anchoring arms 26 can be the same size, in various embodiments, to ease manufacturing considerations. In various embodiments, the anchoring arms 26 of the core 12 can operate independently, relative to the longitudinal axis of the vagina, from the supporting arms 28.

In various embodiments, the difference between sizes of cores 12 can be the resting angle at which supporting arms 28 protrude outwardly relative to the longitudinal axis 24 of the core 12. In various embodiments, "larger" size cores 12 can have a larger radial spread angle of supporting arms 28, hence they can be "shorter" when put next to a smaller size core 12 (i.e., a core 12 which does not radially spread its supporting arms 28 as much). One potential advantage for such a design can be that all cores 12, no matter the radial spread angle, can be inserted into one size of an applicator 40.

In an embodiment, the flexibility of various components of the core 12 of a vaginal insert 10 can be designed both for function and for comfort to the user. In various embodiments, the core 12 of a vaginal insert 10 can be designed with at least one of four aspects of flexibility which can assist in accomplishing these goals of function and comfort. For example, node 22 of core 12 can enable flexibility between the anchoring element 18 and the supporting element 20, which can enable the vaginal insert 10 to adjust to the arch structure of the vagina, as well as to adjust to any position taken by the wearer (e.g., standing, sitting, flexion, etc.) during daily activity. By being able to flex at the node 22, pressure exerted on the vaginal wall can be reduced in relation to a vaginal insert 10 that does not flex at the node 22.

Figures 8, 9:
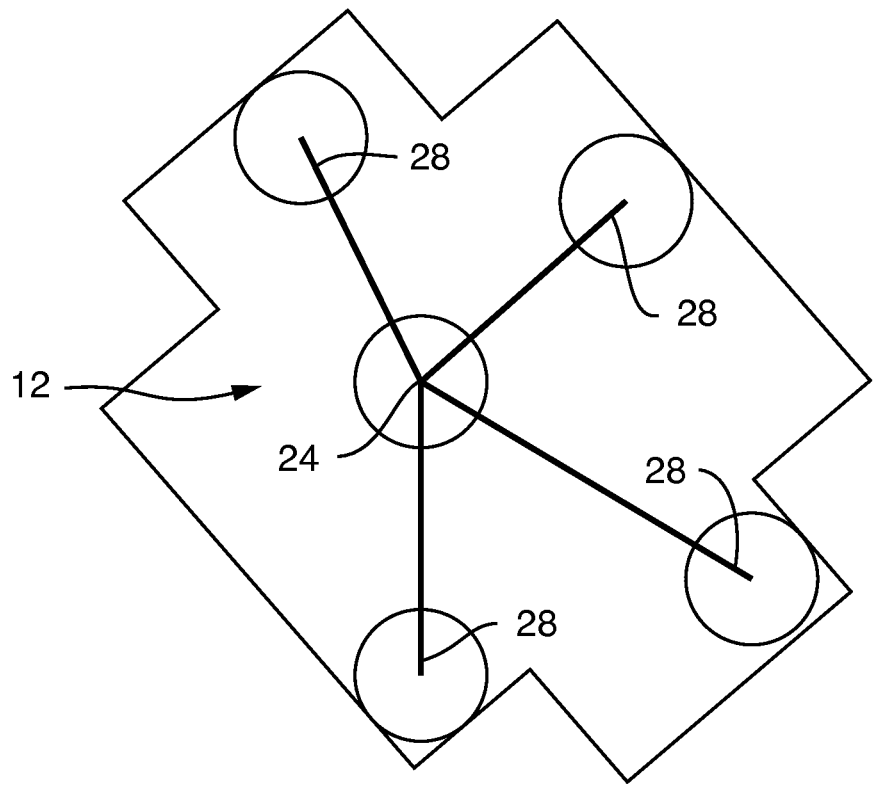
FIG. 8 is a plan view of an exemplary embodiment of a possible relationship of the supporting arms to the longitudinal axis of a core.
FIG. 9 is a table showing exemplary performance ranges for medial deflection and horizontal rotation (left/right from central axis), in accordance with an exemplary embodiment of a core.

Another flexibility aspect of the core 12 can relate to providing efficacy and comfort across varying vaginal planes, for example where the arms, 26 and/or 28, are adapted to contact the vaginal wall at varying locations and/or angles of incidence, relative to each other, away from the longitudinal axis 24, such as shown in FIG. 8, which can allow the core 12 of the vaginal insert 10 to be adaptable to varying vaginal topography/geometries by rotating either left or right from the central axis of each arm.

Another related aspect of flexibility can involve the ability of each of the arms, 26 and/or 28, to perform medial flexion, wherein each arm, 26 and/or 28, can be flexible towards the longitudinal axis 24 when compressed by the vaginal wall, enabling the adjustment of the vaginal insert 10 to various vaginal diameters.

A fourth flexibility aspect can be the feature that each arm, 26 and/or 28, can operate individually, for example, each arm, 26 and/or 28, being able to twist clockwise and/or counterclockwise around its own axis allowing the core 12 of the vaginal insert 10 to overcome vaginal structural variability from one point of contact to the next.

It should be noted that in various embodiments, at least one of these four featured aspects of flexibility can allow the core 12 of the vaginal insert 10 to render effective support regardless of vaginal dimension, vaginal shape, vaginal depth and/or through multiple planes.

FIG. 9 is a table showing exemplary performance ranges for medial deflection (distance the tip of an arm or arms travel toward the longitudinal axis 24 of the core 12) and horizontal rotation (left/right movement perpendicular to longitudinal axis 24), in accordance with an exemplary embodiment of a core 12. Numbers shown are in millimeters. It should be understood that horizontal rotation means rotation in axes perpendicular to the longitudinal axis of the vagina, particularly "right" and "left" when viewing the vagina in the longitudinal axis extending from the vaginal opening to the cervix. The ranges shown in FIG. 9 are amounts in mm that each arm could deviate from its natural position relative to the longitudinal axis 24 of the core 12. Regarding medial deflection, it should be noted that when an arm is deflected medially, there is most often a corresponding arm on the other side of the core 12 which is also deflected medially (but maybe not the same amount), therefore in an embodiment, medial deflection numbers (in mm) are divided by two in order to approximate medial deflection for a single arm. It should also be noted that the numbers for medial deflection in the table in FIG. 9 represent the full amount of deflection for a single arm assuming the corresponding arm does not move at all. In addition, in some embodiments, the maximum amount of medial deflection is dictated by two opposing arms contacting each other, preventing further medial deflection. In various embodiments, the minimum core 12 diameter that can be achieved is 12 mm, with each arm representing a 6 mm portion of that total.

In various embodiments, the core 12 can be made in a plurality of sizes and/or to exhibit specific performance characteristics, such as radial expansion of the supporting arms 28. In various embodiments, the diameter of a radially expanded anchoring element 18 can range from about 30 to about 33 mm. In various embodiments, the diameter of a radially expanded supporting element 20 can range from about 34 mm to about 52 mm. In various embodiments, the core 12 can also be made of different materials and/or materials exhibiting different performance characteristics, such as, for example, hardness. In various embodiments, the core 12 can be constructed of a material or materials which can exhibit a Shore A hardness of 30-80. In various embodiments, core 12 can be manufactured in multiple Shore A hardnesses, including, but not limited to, 40, 50 and 70.

In various embodiments, the core 12 can be constructed from a single piece (Monoblock). In various embodiments, the core 12 can have an anchoring element 18 and a supporting element 20 which can be provided as separate pieces (bi-polar) which can be attached to form the core 12. In various embodiments, each element, supporting 20 or anchoring 18, can be constructed of two or more pieces.

Referring to FIG. 1, a perspective view of a core 12 enclosed within a cover 14 provided with a removal element 16 is illustrated, in accordance with an exemplary embodiment of the vaginal insert 10. Cover 14 can be optionally any of the covers described in PCT/IL2004/000433; PCT/IL2005/000304; PCT/IL2005/000303; PCT/IL2006/000346; PCT/IL2007/000893; PCT/IL2008/001292; U.S. Provisional Patent Application No. 60/719,422; U.S. Provisional Patent Application No. 60/762,059; and, U.S. Provisional Patent Application No. 60/960,492.

In various embodiments, the cover 14 can be smooth. In various embodiments, the cover 14 can be formed from woven or non-woven material. Woven material can include, but is not limited to, textile fabrics which can be made from rayon, cotton, polyolefins, or other synthetic yarns. The synthetics can be either staple or continuous filaments. Non-woven materials can include, but are not limited to, spunbond, bonded carded webs, and hydroentangled webs. In various embodiments, the cover 14 can be constructed from a spunbond non-woven material. In various embodiments, the cover 14 can be treated with an aqueous solution to reduce frictional drag and to enhance the ease of insertion into and withdrawal from a woman's vagina. In various embodiments, the cover 14 can be constructed of a non-woven material such as a 33 gsm non-woven Fiberweb®, Catalog No. 097YLJO09P. In various embodiments, the cover 14 can be constructed of a non-woven material, such as, for example, constructed of about 50% polypropylene and about 50% polyethylene. In various embodiments, the cover 14 can be constructed of nylon. In various embodiments, the cover 14 and the removal element 16 can be constructed of the same unitary piece of material and/or at the same time and/or in the same process. In various embodiments, the cover 14 and the removal element 16 can be constructed of separate pieces of material. In various embodiments, the cover 14 can be constructed of a non-absorbent material. In various embodiments, the cover 14 can be flexible and/or stretchable. In various embodiments, the cover 14 can be formed from a heat-shrinkable material. In various embodiments, the cover 14 can be formed from a material which can be extensible and/or elastic. In various embodiments, elements of the cover 14 can be bonded, stitched, sutured, and/or welded together. In various embodiments, the bonds, stitches, sutures, and/or welds can be located inside the cover 14 opposite the vaginal wall. In various embodiments, the cover 14 and/or the core 12 can be adapted to allow the free flow of vaginal discharge.

In various embodiments, the removal element 16 can be constructed of a cotton material but can be constructed of other materials. In various embodiments, the removal element 16 can be constructed of materials which can allow for absorbing fluids or can be constructed of materials which do not allow for absorbing fluids. In various embodiments, the removal element 16 can be a thread or ribbon made from 100% cotton fibers. In various embodiments, the removal element 16 can be constructed of non-absorbent polyurethane, optionally with a coating of silicone film which can provide a smooth surface to the removal element 16. In various embodiments, the removal element 16 can be a silicone coated, braided polyester, an example of which is manufactured by Ashaway.

In various embodiments, the removal element 16 of the vaginal insert 10 can be from about 14 cm to about 16 cm in length, although the length can be varied in different vaginal insert 10 configurations. In an embodiment, the removal element 16 can be secured to the cover 14 in a position whereby a pulling force towards the vaginal introitus can be substantially evenly distributed over the cover 14 as it collapses the supporting arms 28 of the core 12 within the vagina. In an embodiment, this position can be in the center of the cover 14 in the supporting element 20 region, such as illustrated in FIG. 1.

In various embodiments, the cover 14 can reduce friction between the vaginal insert 10 and the vaginal wall. Pulling the removal element 16 can cause tensioning of the cover 14. Tensioning of the cover 14 can result in the straightening of the vaginal walls which can thereby reduce the tent-like effect described above and relieve tension applied to the vaginal insert 10, allowing for an easy and smooth removal of the vaginal insert 10 from the vagina. Furthermore, pulling on the removal element 16 can cause the collapse of supporting arms 28 at least slightly towards the longitudinal axis 24 as a result of the force applied to them by cover 14, thereby reducing the radial diameter of the core 12 and allowing for an easy and smooth removal of the vaginal insert 10 from the vagina.

Besides being used as an aide in removal of the vaginal insert 10, an additional use of the cover 14 can be to act as a sling stretched between supporting arms 28, which can supply sub-urethral tension-free support to the urethra.

Referring to FIGS. 10-12, perspective views of an applicator 40 which can be utilized to deploy a vaginal insert 10 for treating urinary incontinence are illustrated. In an embodiment, the applicator 40 can comprise a housing 42 and a plunger 44. The housing 42 can be adapted for receipt and/or storage of the vaginal insert 10. In various exemplary embodiments, plunger 44 can be used to expel the vaginal insert 10 from the housing 42 during vaginal insert 10 deployment into a vagina. FIG. 11 is a cross-section of FIG. 10 which can show the configuration of applicator 40 more clearly, including the interface between housing 42 and plunger 44. In various embodiments, housing 42 can be provided with an outlet 46. In various embodiments, outlet 46 can be provided with a plurality of flexible flaps ("petals") which can be pushed open when vaginal insert 10 is expelled from applicator 40. The outlet 46 is more clearly shown in FIG. 12.

In the applicator 40, the vaginal insert 10 can be positioned such that the anchoring element 18 of the core 12 comes out of the applicator 40 into the vagina first, followed by supporting element 20 of the core 12, which comes out at the end of the deployment process. In an embodiment, the vaginal insert 10 can be deployed to render support to the urethra. In an embodiment, the vaginal insert 10 can be deployed to render support to the bladder neck.

Figure 13:
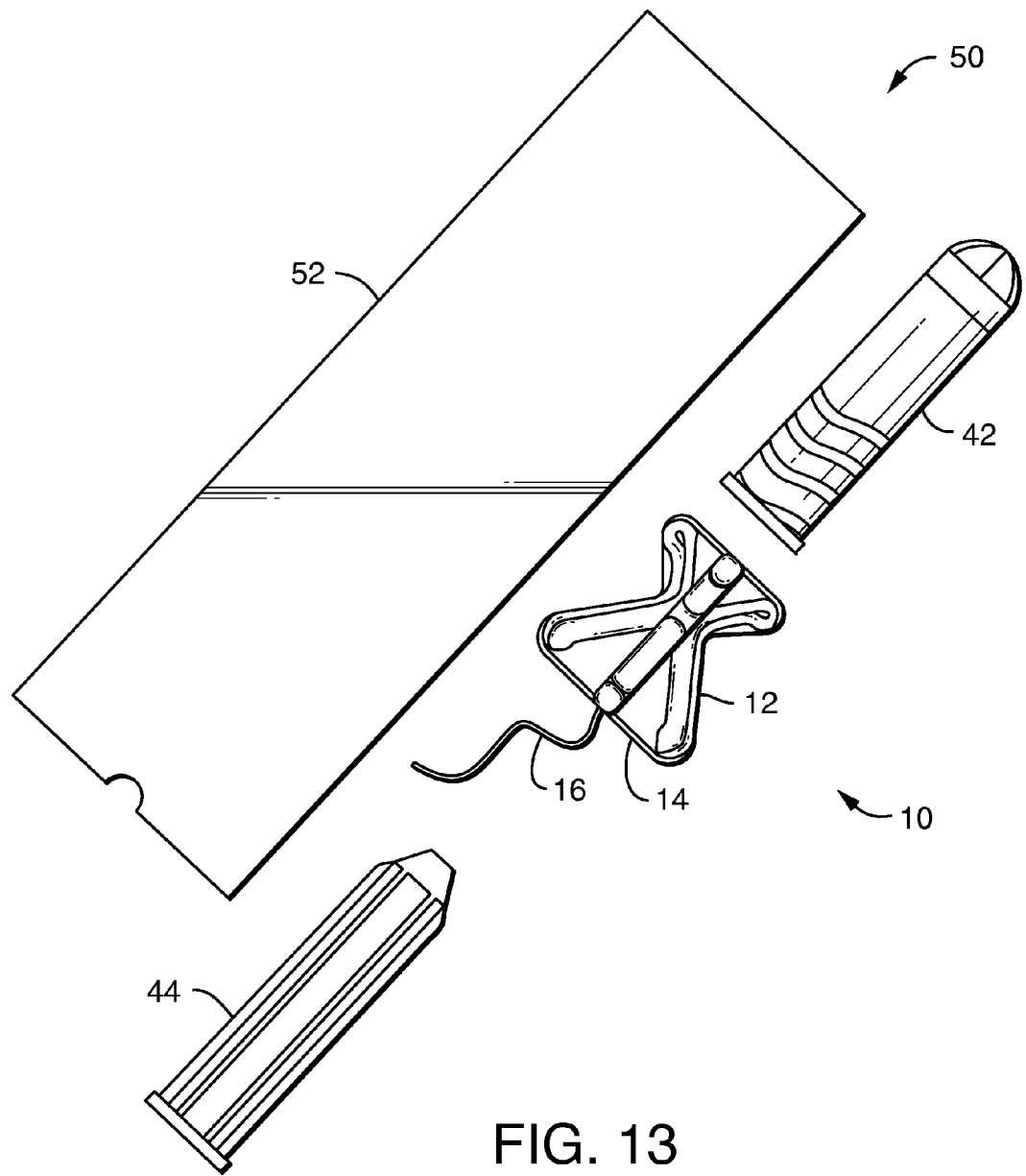
FIG. 13 is a side view of an exemplary embodiment of the component parts of a product package for a vaginal insert.

In an embodiment, a user can receive the vaginal insert 10 in an individual package 50 such as shown in FIG. 13. In an embodiment, different sizes and/or packages 50 with vaginal inserts 10 having different features can be color coded for ease of identification by a user of the vaginal insert 10. FIG. 13 is a side view of the component parts of a product package 50 for a vaginal insert 10 for treating urinary incontinence. Product package 50 can comprise an applicator housing 42, core 12, cover 14, removal element 16, applicator plunger 44, and product wrapper 52. In an embodiment, product wrapper 52 can be wrapped around the applicator 40, which when packaged can include the vaginal insert 10 within the housing 42. Thus, product package 50 in its assembled form can be more or less cylindrical or shaped like a wrapped tampon.

In an embodiment, insertion of the vaginal insert 10 into the vagina can be similar to insertion of a tampon. The user can use one hand to spread the labia, direct the anterior part of the applicator 40 into the vagina, and compress the plunger 44 with the other hand, thereby deploying the vaginal insert 10 from the applicator 40 into the vagina. In an embodiment, there is no need for a specific orientation of the vaginal insert 10 because of the generally symmetrical design of the core 12 about the longitudinal axis 24 of the core 12. The insertion of the vaginal insert 10 can be performed at any orientation and/or anywhere in the 360° around the longitudinal axis 24 of the core 12 in the applicator 40.

In various embodiments, even though the core 12 can be designed symmetrically, because each of the arms, 26 and 28, can flex independently of the other arms, 26 and 28, when in situ and each vagina varies in shape slightly, the vaginal insert 10 may not actually be in symmetrical form when in use (see FIG. 8). Referring to FIG. 8, a plan view showing a possible relationship of the supporting arms 28 to the longitudinal axis 24 of the core 12 when the vaginal insert 10 is in situ is illustrated. It is noted that not every vagina has the same contours and internal structure, even though some generalizations can be made about vaginal anatomical features. To that end, the core 12 can be designed to be adaptable to the varying vaginal features it may come across, depending on the user of the vaginal insert 10. For example, each of the supporting arms 28 of the core 12 can be capable of functioning independently. This can enable maximal flexibility, maximal adjustment to any vaginal shape (cross section) and/or vaginal dimensions. Thus, it may happen that in a given cross section, the supporting arms 28 of the core 12 will not be symmetrically spread around the longitudinal axis 24 of the core 12, such as shown in FIG. 8.

The core 12 can be manufactured and/or commercially available in a plurality of sizes, with each size exhibiting different performance characteristics, operational dimensions, weight and the like. In various embodiments, differently sized cores 12 can be made of the same material. In various embodiments, differently sized cores 12 can use different materials and/or different material ratios. FIGS. 14A-14C are a series of charts illustrating exemplary core 12 sizes. As can be seen in the charts of FIGS. 14A-14C, core 12 can be produced in at least four sizes for optimal adjustment to various vaginal dimensions and/or in accordance with the severity of urinary incontinence. The various sizes can differ in the diameter of the supporting arm's 28 spread and as a result, can differ in the overall length when deployed (i.e., the supporting arms 28 are spread). In various embodiments, the anchoring arms 26 can have identical deployed dimensions and/or performance characteristics in all of the sizes.

In various embodiments, core 12 can be constructed of liquid silicone (LSR) by injection molding. It is possible to use other materials, for example TPE, non-liquid silicone, and others for a core 12 of the same size. In an embodiment, materials exhibiting various degrees of Shore A hardness can be used to produce softer or more rigid cores 12.

It should be understood that the various size combinations can be made by varying the size and/or Shore A hardness. For example, sizes 1 and 2, could be made with a Shore A hardness of 70 while sizes 3 and 4 can have a Shore A hardness of 40. In various embodiments, all of the core 12 sizes can exhibit the same Shore A hardness. In various embodiments, each individual size can be made in multiple versions, each exhibiting a different Shore A hardness. In sum, various combinations and permutations of features, sizes, performance characteristics and/or construction materials can be employed to apply desired sub-urethral supporting force at certain working angles.

In various embodiments, the radiating supporting arms 28 of core 12 can create an overall core 12 diameter from about 34 mm to about 52 mm at the widest supporting element 20 cross section within the vaginal cavity. In various embodiments, the diameter can be larger or smaller depending on the individual needs of the user.

Figure 15:
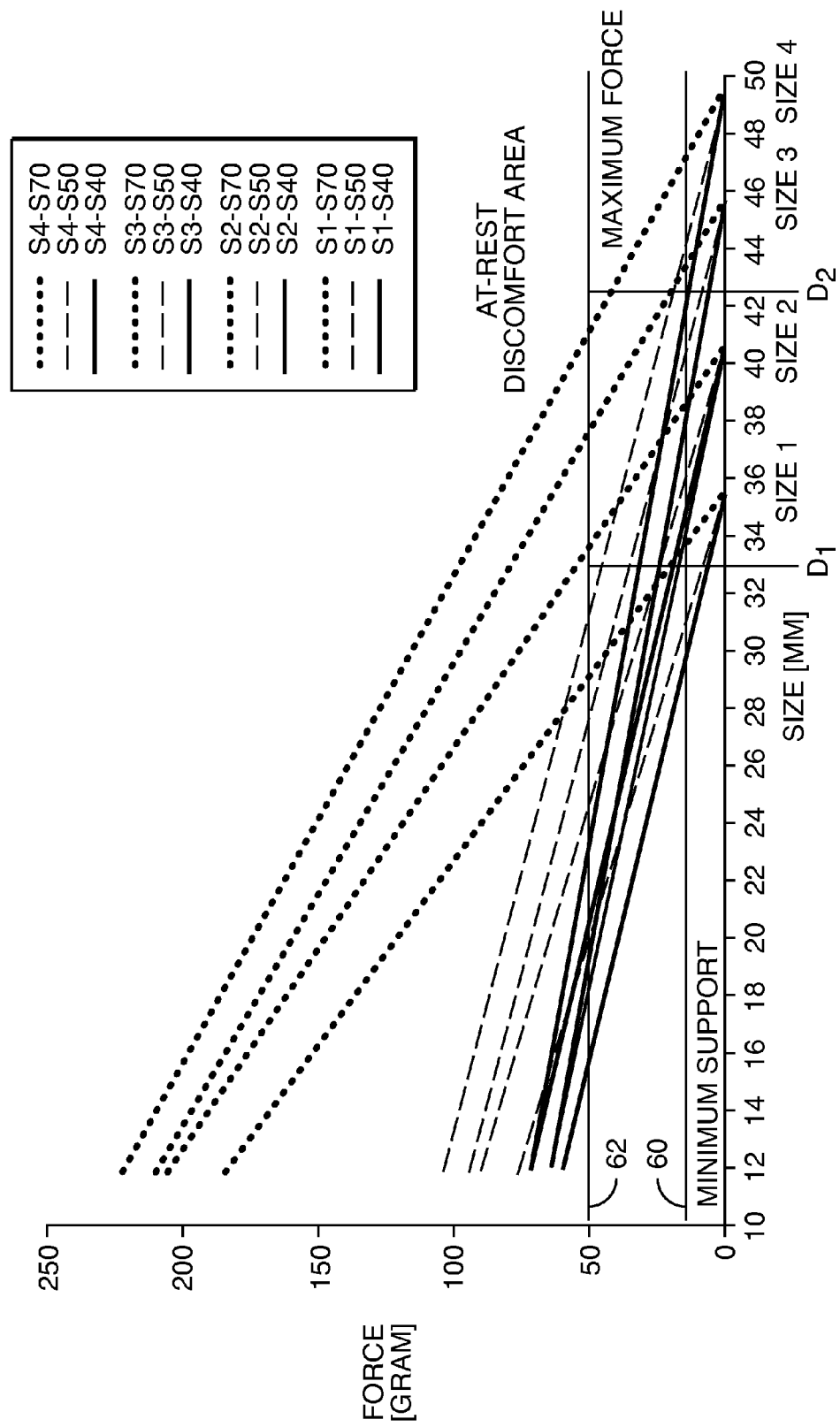
FIG. 15 is a vaginal insert performance graph correlating force exerted to core size, diameter and hardness.

FIG. 15 is a core 12 performance graph correlating expansive force exerted by supporting arms 28 (y-axis) to amount of medial deflection (x-axis) and hardness (line hatchings) for each of the four basic sizes shown in FIGS. 14A-14C whereby medial deflection is the distance in mm towards the longitudinal axis 24 of the core 12 from the natural expanded state of the supporting arm 28.

The expansive force exerted by the supporting arms 28 is generally determined by the hardness grade and/or the medial flexion degree (medial deflection) of each of the supporting arms 28 relative to the longitudinal axis 24. If a specific material is used in construction of the core 12, such as, for example, liquid silicone, these forces can be measured for any given diameter of the supporting arms 28 of the core 12, knowing the performance characteristics of the specific material being used. Using this data in a graph where the x-axis represents the core 12 diameter and the y-axis represents the force, the forces exerted by the supporting arms 28 for a given core 12 size and its material hardness grade can be demonstrated. The slope represents the ratio between the force (grams) and the amount of medial deflection (mm).

In designing and/or selecting a core 12 for use, certain performance considerations can be taken into account. It should be noted that core 12 support is "activated" by the supporting arms 28 being compressed (i.e., deflected towards the longitudinal axis 24 of the core 12, or "medial deflection") at least slightly by the vaginal wall. In general, the stronger the compressive forces on the supporting arms 28, the stronger the support force that is exerted back onto the vaginal wall/sub-urethra by the supporting arms 28. For example, supporting arms 28 must be compressed a certain minimal amount in order to provide counterforce sufficient for the supporting arms 28 to render support. That is, if a vaginal insert 10 is inserted into a vagina and the core 12 is too small or the angle of radial expansion is too small, then not enough force will be applied to the supporting arms 28 from the vaginal wall to cause the supporting arms 28 to counter with the force required to render appropriate and effective support. Failure to achieve this minimal value of compression in an at-rest state, shown as a horizontal minimal applied force line 60 in FIG. 15 at approximately 10 g of force, on the supporting arms 28 during a stressful event will reduce vaginal insert 10 efficacy. It should be noted that in some embodiments, the minimal applied force line 60 at 10 g is approximate and can vary ±3 grams.

Similarly, there exists a maximum force exerted by the core 12 on the vaginal walls beyond which the user would experience discomfort while the vaginal insert 10 is in the vagina at-rest and/or while removing the vaginal insert 10. In an embodiment, therefore, the core 12 can be designed and/or selected for use not to exceed this maximal force. This maximal force is represented in FIG. 15 as the bold horizontal line 62 at approximately 50 g of force. In an embodiment, 50 grams is approximate and can vary ±5 grams. For example, if the radial expansion of the supporting arms 28 is too great, it will generate excessive force on the vaginal wall and the user may experience discomfort, which is to be avoided.

The graph of FIG. 15 can be used, in various embodiments, to determine the use potential for a specific core 12 configuration for a specific vaginal size. For example, D1 on the graph represents a vagina with a diameter of 33 mm. Referring to FIG. 15, it can be seen that size 1 cores 12 with Shore A hardnesses of S40 and S50 are not indicated for use with this user because they will not provide sufficiently effective support in an at-rest state. However, a number of other core 12 sizes and Shore A hardnesses are considered acceptable:

Size 1 with Shore A hardness of 70 device (supplying force of about 21 grams)
Size 2 with Shore A hardness of 50 device (supplying force of about 25 grams)
Size 2 with Shore A hardness of 40 device (supplying force of about 20 grams)
Size 3 with Shore A hardness of 50 device (supplying force of about 38 grams)
Size 3 with Shore A hardness of 40 device (supplying force of about 28 grams)
Size 4 with Shore A hardness of 50 device (supplying force of about 48 grams)
Size 4 with Shore A hardness of 40 device (supplying force of about 35 grams)

As another example, D2 on the graph represents a vagina with a diameter of 42.5 mm. Because of the size of this user's vagina, fewer choices may be available for receiving ideally efficacious vaginal support. In this example, likely choices would include:

Size 3 with Shore A hardness of 70 device (supplying force of about 22 grams)
Size 4 with Shore A hardness of 70 device (supplying force of about 45 grams)
Size 4 with Shore A hardness of 50 device (supplying force of about 22 grams)
Size 4 with Shore A hardness of 40 device (supplying force of about 18 grams)

It is noted that a size 4 core 12 made of a low Shore A hardness material, for example 40, can be used for a wide variety of vaginal diameters (approximately 30 mm to 45 mm), in an exemplary embodiment.

Above the maximum force line 62, the graph of FIG. 15 shows force exertion levels of the various core 12 sizes at different levels of medial deflection all the way down to about 12 mm in total core 12 diameter. In an embodiment, each arm is approximately 6 mm in width, therefore the minimum diameter distance possible is when two opposing arms have come into contact or 12 mm (6 mm+6 mm). Specific numbers for selected core 12 sizes are shown in and described in more detail below with respect to FIG. 16.

FIG. 16 is a table showing specific performance levels for exemplary basic core 12 sizes and Shore A hardnesses depicted in FIG. 15. The minimal diameter column lists the diameter (in mm) at which two opposing arms 28 come into contact thereby substantially prohibiting any further medial deflection by the arms 28. In an embodiment, maximal force is exerted when the cores 12 are compressed the most, or at the minimal diameter. The max force column lists the maximum amount of force exerted by each listed core 12 size and Shore A hardness at the 12 mm diameter level.

It is noted that some of the information shown in FIG. 16 is also included in the tables of FIGS. 14A-14C. Where the information is not entirely in conformance, it should be understood that the broadest range of values is to be attributed to the embodiments described herein. For example, a range of values may be taken where the low end of the range is from one table and the high end of the range is from another table. It should also be noted that values given are by way of example only, and that core 12 performance characteristics can vary depending on materials used for construction and/or core 12 size and/or Shore A hardness.

In various embodiments, many of the possible sizes of cores 12 can be suitable for a particular user and sufficient support can be provided without surpassing the discomfort threshold. This can be particularly true with cores 12 of low Shore A hardness and moderate slope. For example, a core 12 of size 3 (support diameter—45 mm) made of soft silicone with a Shore A hardness of 40 may be suitable for a broad range of vaginal diameters: exerting a force of 12 grams over a diameter of 40 mm, 21 grams over a diameter of 35 mm, and 31 grams over a diameter of 30 mm. In other words, in some embodiments, a single core 12 size can provide support to numerous vaginal dimensions. In an embodiment, a core 12 can be adapted to be usable by a variety of users, for example by designing a core 12 with a low or moderate slope.

It is possible that only one size of core 12 will be suitable for a woman with a certain vaginal diameter, especially if her vaginal dimensions are larger than the average. In some embodiments, only sizes 3 or 4 would be suitable, while the smaller sizes would not exert the minimal support force required. It should be noted that characteristics such as the force applied, the size of the vaginal insert 10 and/or overall comfort of the vaginal insert 10 chosen is highly dependent on each individual user and may also depend on the pathological response caused by the vaginal insert 10 for each individual user.

In an exemplary embodiment, reducing the distance between the supporting tip 32 of a supporting arm 28 and the longitudinal axis 24 of the core 12 would increase the force exerted by the core 12 at the supporting tip 32. The operative significance of this can be that a relatively large vaginal insert 10 inserted into the vagina would exert a higher force on the vaginal walls as compared to a smaller vaginal insert 10 inserted into the same vagina. Using this same rationale, if external forces exerted on the vaginal insert 10 reduce the internal distance between its supporting arms 28 and the longitudinal axis 24 (e.g. during coughing, jumping, sneezing, etc.), a greater counteracting force would be exerted by the supporting arms 28 on the vaginal walls, thus enhancing the urethral support and the efficiency of urinary leak prevention. Therefore, in an exemplary embodiment, a vaginal insert 10 can be designed with this activity-generated counter tension in mind.

Vaginal Insert Method of Manufacture:

As described above, in an embodiment, a vaginal insert 10 can have a core 12, a cover 14, and a removal element 16. The manufacturing process to produce a vaginal insert 10 can include steps such as providing a cover blank 68, enclosing a core 12 within the cover blank 68, and providing a removal element 16. In various embodiments, the manufacturing process can also include a step of conforming the cover 14 to the core 12.

For the vaginal insert 10 to be efficacious in reducing episodes of leakage due to urinary incontinence, the vaginal insert 10 needs to be small enough for insertion into and removal from the vagina, but also needs to be able to radially expand following insertion and during wear. The core 12 of the vaginal insert 10, therefore, should be capable of transitioning between a compressed configuration and a radially expanded configuration. To avoid restricting this transition between configurations, the cover 14 should be sized large enough to allow the core 12 to expand to its largest required dimension during wear. While the cover 14 should be large enough to allow expansion of the core 12, the cover 14 should also be sized correctly to assist in the removal of the vaginal insert 10. As described herein, pulling on the removal element 16 can result in a pulling force being substantially evenly distributed over the cover 14 which can work to collapse the supporting arms 28 of the core 12 towards the longitudinal axis 24 of the core 12, thereby reducing the radial diameter of the core 12 and allowing for a smooth and easy removal of the vaginal insert 10 from the vagina. The cover 14, therefore, should not be sized so large that the cover 14 has little effect on the supporting arms 28 of the core 12 when pulling on the removal element 16 during removal of the vaginal insert 10.

In an embodiment, the cover 14 can conform to the shape and/or size of the core 12. As mentioned above, in various embodiments, the cover 14 can act as a sling stretched between arms, such as the supporting arms 28, of the core 12. In such embodiments, the cover 14 can supply suburethral tension free support to the urethra. Also as described herein, the core 12 can transition from a compressed configuration to a radially expanded configuration to provide support to the urethra. The cover 14 can be conformed to the size and/or shape of the core 12 in order to provide the cover 14 with the tension needed to allow the cover 14 to adequately act as a sling and support the urethra. Without being bound by theory, it is believed that a cover 14 that is not conformed to the size and/or shape of the core 12, or has not been adequately conformed to the size and/or shape of the core 12, will be too loose as an enclosure to the core 12 and will not provide adequate support to the urethra. As mentioned above, the cover 14, however, should not be overly conformed to the size and/or shape of the core 12 as that could prevent the core 12 from radially expanding to the extent necessary to provide adequate support to the urethra. In various embodiments, the cover 14 can be conformed to the core 12 via a process which can reduce the dimensions of the cover 14 and maintain the reduced dimensions of the cover 14. In various embodiments, the cover 14 can be conformed to the core 12 via a process which can reduce the dimensions of the cover 14 at the narrowest portion of the core 12, such as, for example, the node 22. In various embodiments, the dimensions of the cover 14 can be reduced via processes such as, but not limited to, wrapping a band of material around the cover 14 to "tighten" the cover 14, twisting the material forming the cover 14, applying a thermal treatment to the cover 14 such as a cover 14 formed of a heat-shrinkable material, and/or altering the elastic and/or extensible properties of the cover 14. In an embodiment, the cover 14 shape and/or dimensions can be substantially similar to the expanded shape and/or dimensions of the core 12. In an embodiment, the internal volume of the cover 14 can be substantially similar to the volume of the expanded core 12.

A cover 14 can be formed from a cover blank 68. A cover blank 68 can be created via at least one of two methods. A first method of creating a cover blank 68 can include folding a single material in half, bringing the two halves together in a face-to-face relationship, and bonding at least a portion of the two halves together to create at least one bond area. A second method to create a cover blank 68 can include providing two separate materials together in a face-to-face relationship and bonding at least a portion of the two separate materials together to create at least one bond area. The at least one bond area, resulting from either method just described, can ultimately provide at least one seam for a cover 14. In various embodiments, a cover blank 68 can have at least one bond area. In various embodiments, a cover blank 68 can have at least two bond areas. In various embodiments, a cover blank 68 can have at least three bond areas. Once the cover blank 68 fully encloses a core 12 and the material forming the cover blank 68 has been fully seamed together to prevent the core 12 from escaping the confines of the cover blank 68, the cover blank 68 can be said to have been converted to a cover 14. In various embodiments, the cover 14 can have at least one seam. In various embodiments, the cover 14 can have at least two seams. In various embodiments, the cover 12 can have at least three seams. In various embodiments, the cover 12 can have at least four seams.

The terms "bonded" and "bonding" refer herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding can occur via adhesive, pressure bonding, thermal bonding, ultrasonic bonding, stitching, suturing, and/or welding.

Figure 17:
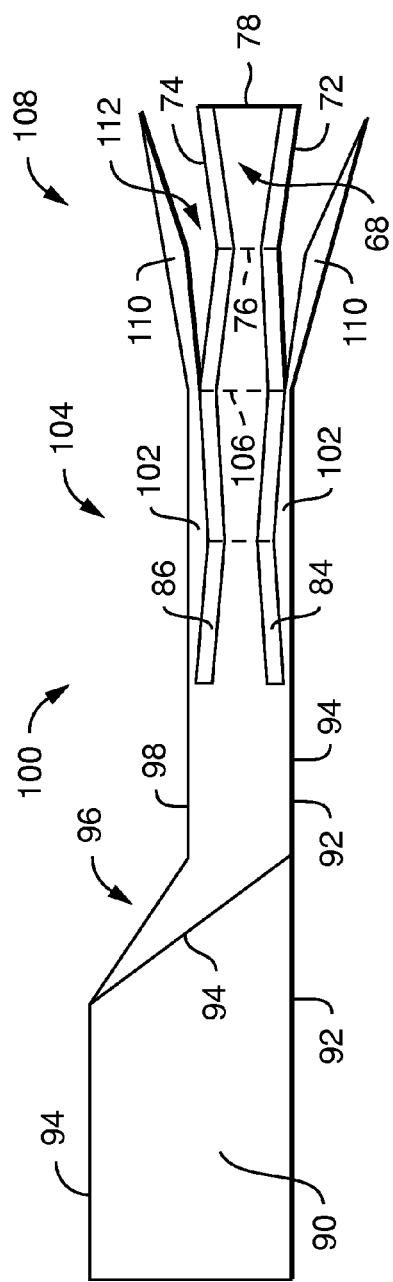
FIG. 17 is an exemplary illustration of a portion of a process to manufacture an embodiment of a cover blank.

FIG. 17 provides an exemplary illustration of a method to manufacture a cover blank 68. As illustrated in FIG. 17, a single material 90 can be utilized. The material 90, in an unfolded configuration, can have two opposing and spaced apart machine-directions edges, such as edges 92 and 94. The material 90 can enter a folding zone 96 wherein the material 90 can be folded such that two halves of the material 90 can be created with one half brought into a face-to-face relationship with the other half of material 90. The folding of material 90 can be accomplished through the use of, for example, a folding board. The folding of material 90 can bring edge 94 into a position substantially adjacent to edge 92. The resulting fold 98 in the material 90 can remain parallel to and spaced apart from the edges, 92 and 94, and the fold 98 and the edges, 92 and 94, can continue to move in the machine direction. The folded material 90 can continue to a bonding zone 100 wherein at least a portion of one of the halves of the folded material 90 can be bonded to at least a portion of the other half of the folded material 90. The bonding can be accomplished by methods such as, but not limited to, adhesive, pressure bonding, thermal bonding, ultrasonic bonding, stitching, suturing, and/or welding.

The bonding of at least a portion of the two halves of folded material 90, or, in various embodiments, the bonding together of at least a portion of two separate materials, can form at least one bond area. The at least one bond area can ultimately provide at least one seam of a cover 14. A bond area can have a width as deemed suitable to maintain the integrity of the bond area, and resultant seam of the cover 14. In various embodiments, a bond area can have a width from about 0.1, 0.2, 0.3, 0.4, or 0.5 mm to about 0.6, 0.7, 0.8, 0.9 or 1.0 mm.

Referring to FIG. 17, in the exemplary embodiment of the method illustrated, two bond areas, 84 and 86, can be created. As the bond areas, such as bond areas 84 and 86, can ultimately provide a seam for the cover 14, the bond areas, 84 and 86, can provide a portion of the shape of the cover blank 68. In various embodiments, the cover blank 68 can have a rectangular, trapezoidal, or trapezoid-like shape when viewed in a flat, two-dimensional configuration. A trapezoid-like shape can have at least two parallel sides and the other two sides can be non-parallel, can have an arc, or can have any other shape as desired. As can be seen in the exemplary illustration of FIG. 17, the bond areas, 84 and 86, which have been formed can provide for a cover blank 68 which can have a trapezoidal shape when viewed in a flat, two-dimensional configuration.

In various embodiments, the desired maximum width of the cover blank 68, in a flat, two-dimensional configuration, at its widest dimension, can be narrower than the width of the material(s) 90 provided and bonded together to form the cover blank 68. In such various embodiments, an area of trim material can be located between the bond areas, such as bond areas 84 and 86, and the edges and/or fold of the material 90 utilized to make the cover blank 68. In the exemplary embodiment illustrated in FIG. 17, the bond areas, 84 and 86, can be located interior to the edges, 92 and 94, and the fold 98 of the material 90. Areas of trim 102, therefore, can be located between the bond areas, 84 and 86, and the edges, 92 and 94, and the fold 98 of the material 90. As the material 90 can be further processed into a cover blank 68, the areas of trim 102 can be separated from the bond areas, 84 and 86, as trim waste 110. The removal of the trim waste 110 will be discussed herein below.

The material 90 can enter a perforation zone 104 wherein perforations 106 can be imposed upon the material 90. The perforations 106 can be created through the use of any perforation cutter deemed suitable. The perforations 106 can be a perforations 106 extending across the material 90 in the cross-machine direction. The perforations 106 can provide a separation between ultimately two cover blanks 68. In various embodiments, the perforations 106 may not extend into the areas of trim 102 located between the bond areas, 84 and 86, and the edges, 92 and 94, and the fold 98 of the material 90. In various embodiments, without being bound by theory, it is believed that not extending the perforations 106 into the areas of trim 102 can enable efficient removal of the areas of trim 102 during the manufacturing process.

To remove the areas of trim 102, the material 90 can enter a trim removal zone 108 wherein a slitter can be used to separate the areas of trim 102, as trim waste 110, from the material 90. The trim waste 110 can be pulled away from the material 90 via any method deemed suitable, such as a vacuum. After the areas of trim 102 have been removed, as trim waste 110, the bond areas 84 and 86, can become seams, such as side seams 72 and 74, of a cover blank 68.

Figure 18:
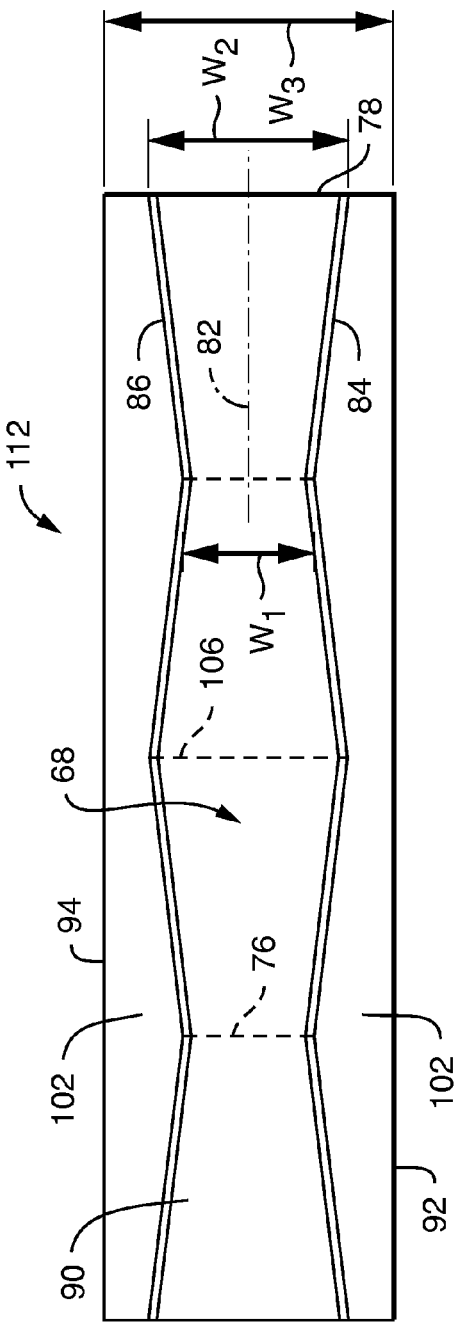
FIG. 18 is an exemplary illustration of a portion of a process of sequential manufacture of multiple cover blanks in a flat, two-dimensional configuration.

It should be noted that, in various embodiments, the machine-direction length of material(s) 90 provided to manufacture a cover blank 68 can be sufficient to manufacture a single cover blank 68 or, in various embodiments, the machine-direction length of the material(s) 90 provided can be sufficient to manufacture multiple cover blanks 68 such as, for example, a ribbon 112 of cover blanks 68 manufactured in a sequential manner. FIGS. 17 and 18 provide exemplary illustrations of a ribbon 112 of cover blanks 68. FIG. 17 can provide an illustration of a ribbon 112 of cover blanks pre- and post-separation of the areas of trim 102. FIG. 18 can provide an illustration of a ribbon 112 of cover blanks 68 pre-separation of the areas of trim 102.

Referring to FIG. 18, an exemplary embodiment of a portion of a ribbon 112 of cover blanks 68 can be illustrated. In FIG. 18, two separate materials 90 can be brought in a face-to-face relationship. Each of the materials 90 can have parallel and spaced apart edges, such as edges 92 and 94, extending in the machine-direction. At least a portion of the two separate materials 90 can be bonded together and bond areas, 84 and 86, can be created. Areas of trim 102 can be located between the bond areas, 84 and 86, and the edges, 92 and 94, of the materials 90. As can be seen in the exemplary embodiment of FIG. 18, the width W3 of the materials 90 forming the cover blank 68 can be larger than the widest width of the cover blank 68, such as width W2 of the cover blank 68.

As illustrated in the exemplary embodiments of FIG. 17 and FIG. 18, the ribbon 112 of cover blanks 68 illustrates that the largest width W2 of a first cover blank 68 is sequentially adjacent to the largest width W2 of the next cover blank 68 and the narrowest width W1 of a first cover blank 68 is sequentially adjacent to the narrowest width W1 of the next cover blank 68. Without being bound by theory, it is believed that maintaining the narrowest widths W1 of two cover blanks 68 in an adjacent relationship as well as maintaining the widest widths W2 of two cover blanks 68 in an adjacent relationship can provide for a more efficient incorporation of the perforation 106 between cover blanks 68 as well as for a more efficient removal of the areas of trim 102 as trim waste 110.

In a manufacturing process for sequential manufacture of cover blanks 68, a connected ribbon 112 of cover blanks 68 can be present prior to the separation of the areas of trim 102 as trim waste 110 such as illustrated in FIG. 18. In a manufacturing process for sequential manufacture of cover blanks 68, a connected ribbon 112 of cover blanks 68 can be present post separation of the areas of trim 102 as trim waste 110, such as illustrated in FIG. 17. A single cover blank 68 can be separated from the connected ribbon 112 of cover blanks 68 by breaking the perforations 106 between two adjacent cover blanks 68.

Figure 19:
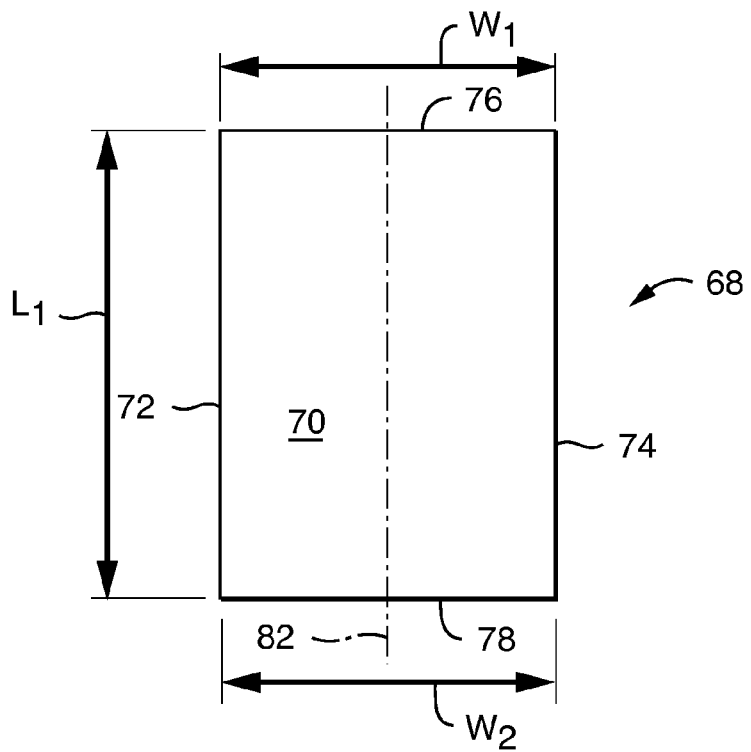
FIGS. 19-20 are top down views of exemplary embodiments of cover blanks in a flat, two-dimensional configuration.
Figure 20:
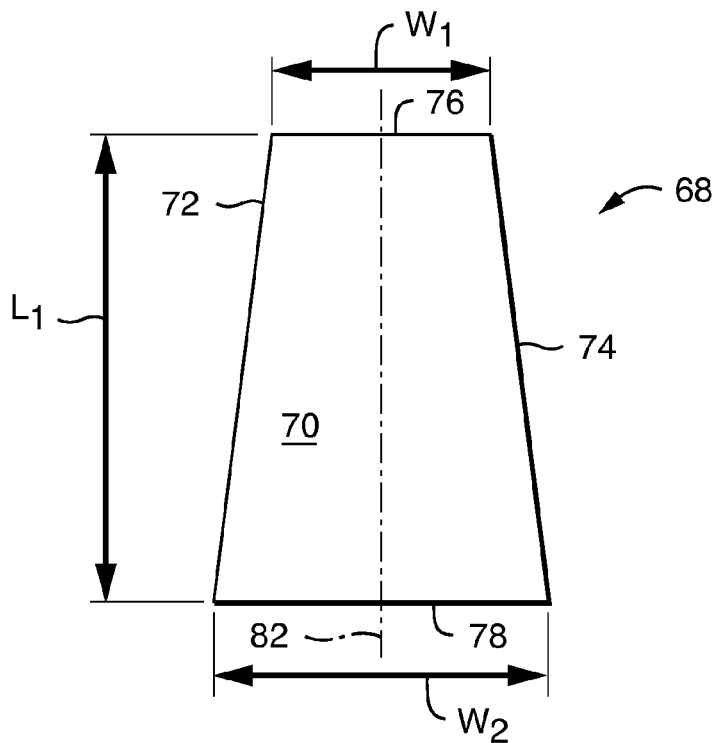

FIGS. 19 and 20 provide exemplary illustrations of cover blanks 68 in flat, two-dimensional configurations, which can be separated from a ribbon 112 of cover blanks 68. As the cover blank 68 can be manufactured from a single material 90 folded over onto itself or from two materials 90 brought together in a face-to-face relationship, the cover blank 68, 70 and 80, of material 90 with one layer, such as layer 70, overlaying the other layer, such as layer 80. In the exemplary embodiments illustrated in FIGS. 19 and 20, layer 70 is facing the viewer. The cover blank 68 can have bonded side seams, such as side seams 72 and 74. The cover blank 68 can have top edges 76 of each layer, 70 and 80, which are not bonded to each other. The cover blank 68 can have bottom edges 78 of each layer, 70 and 80, which are not bonded to each other. In various embodiments, when viewed in a flat, two-dimensional configuration, the cover blank 68 can have the rectangular configuration as illustrated in the exemplary embodiment of FIG. 19. In various embodiments, when viewed in a flat, two-dimensional configuration, the cover blank 68 can have the trapezoidal configuration as illustrated in the exemplary embodiment of FIG. 20. In various embodiments, when viewed in a flat, two-dimensional configuration, a cover blank 68 can have a trapezoid-like configuration. In various embodiments, when viewed in a flat, two-dimensional configuration, the cover blank 68 can have any other configuration as deemed suitable to provide a cover 14 for enclosing a core 12.

During the manufacturing process, the top edges 76 of each layer, 70 and 80, and the bottom edges 78, of each layer, 70 and 80, can be bonded together to ultimately form the cover 14 for a core 12 of a vaginal insert 10. The bottom edges 78 of each layer, 70 and 80, when bonded together can form a bonded area 168 which can be located near the supporting element 20 of the core 12. The top edges 76 of each layer, 70 and 80, when bonded together can form a bonded area 318 which can be located near the anchoring element 18 of the core 12.

In various embodiments, when viewed in a flat, two-dimensional configuration, a cover blank 68 can have a rectangular configuration such as illustrated in FIG. 19. The cover blank 68 can have an initial longitudinal length L1, measured as the distance from the top edge 76 to the bottom edge 78 of the layers, 70 and 80. Each of the edges, top edge 76 and bottom edge 78, of the respective layers, 70 and 80, can have an initial top edge width W1 and an initial bottom edge width W2, respectively. In an embodiment, such as illustrated in FIG. 19, in which the cover blank 68 can have a rectangular configuration, the initial top edge width W1 and the initial bottom edge width W2 can be the same.

In an embodiment, the core 12 can be symmetrical about the longitudinal axis 24 of the core 12 as well as symmetrical about the lateral axis of the core 12 wherein the lateral axis of the core 12 can be located at the midpoint of the longitudinal axis 24 of the core 12. These symmetries can be present when the core 12 can be in a compressed configuration and when the core 12 can be in a radially expanded configuration. In such an embodiment, a cover blank 68 can be provided which can be symmetrical and/or can assume symmetry about the longitudinal axis 82 of the cover blank 68 as well as can be symmetrical and/or can assume symmetry about the lateral axis of the cover blank 68 wherein the lateral axis of the cover blank 68 can be located at the midpoint of the longitudinal axis 82 of the cover blank 68. These symmetries of the cover blank 68 can be visible when the cover blank 68 can be viewed in a flat, two-dimensional configuration, such as prior to the enclosure of a core 12 within the cover blank 68. FIG. 19 provides an illustration of a cover blank 68 in a flat, two-dimensional configuration and the cover blank 68 can have a symmetrical configuration around both the longitudinal axis 82 of the cover blank 68 and about the lateral axis located at the midpoint of the longitudinal axis 82 of the cover blank 68.

In various embodiments, when viewed in a flat, two-dimensional configuration, a cover blank 68 can have a trapezoidal configuration such as illustrated in FIG. 20. The cover blank 68 can have an initial longitudinal length L1, measured as the distance from the top edge 76 to the bottom edge 78 of the layers, 70 and 80. Each of the edges, top edge 76 and bottom edge 78, of the respective layers, 70 and 80, can have an initial top edge width W1 and an initial bottom edge width W2, respectively. In an embodiment, such as illustrated in FIG. 20 in which the cover blank 68 can have a trapezoidal configuration, the initial top edge width W1 may not be the same as the initial bottom edge width W2. In such an embodiment, the top edge width W1 can be smaller than the bottom edge width W2.

In an embodiment, the core 12 can be symmetrical about the longitudinal axis 24 of the core 12, however, the core 12 may not be symmetrical about the lateral axis of the core 12 wherein the lateral axis of the core 12 can be located at the midpoint of the longitudinal axis 24 of the core 12. The symmetry of the core 12 about the longitudinal axis 24 of the core 12 can be present when the core 12 can be in a compressed configuration and when the core 12 can be in a radially expanded configuration. In such an embodiment, a cover blank 68 can be provided which can be symmetrical and/or can assume symmetry about the longitudinal axis 82 of the cover blank 68. The symmetry of the cover blank 68 about the longitudinal axis 82 of the cover blank 68 can be visible when the cover blank 68 can be viewed in a flat, two-dimensional configuration, such as prior to the enclosure of a core 12 within the cover blank 68. FIG. 20 provides an illustration of a cover blank 68 in a flat, two-dimensional configuration and the cover blank 68 can be symmetrical about the longitudinal axis 82 of the cover blank 68 but may not be symmetrical about the lateral axis located at the midpoint of the longitudinal axis 82 of the cover blank 68.

As described herein, FIG. 14 provides exemplary core 12 configurations when the core 12 can be in a deployed/radially expanded configuration. The cover blank 68 can be appropriately sized to enclose a core 12 such as described herein. It should be noted that as the core 12 can be provided in various sizes, the cover blank 68 can also be provided in various initial sizes to conform to the size of the core 12. In various embodiments, the cover blank 68, in a flat, two-dimensional configuration, and prior to the enclosure of a core 12, can have an initial longitudinal length L1 from about 90, 92, 94, 96, 98, 99 or 100 mm to about 101, 102, 104, 106, 108, or 110 mm. In an embodiment, the cover blank 68, in a flat, two-dimensional configuration, and prior to the enclosure of a core 12, can have an initial longitudinal length L1 of about 100 mm±1 mm. In various embodiments, the cover blank 68, in a flat, two-dimensional configuration, and prior to the enclosure of a core 12, can have an initial top edge width W1 and a bottom edge width W2 from about 40, 42, 44, 46, 48, 50, 52, 54, 56, 58 or 60 mm to about 70, 72, 74, 76, 78, 80, 82, 84, 86, 88 or 90 mm. In an embodiment, the cover blank 68, in a flat, two-dimensional configuration can be rectangular in shape and the top edge width W1 can be the same as the bottom edge width W2. In an embodiment, the cover blank 68, in a flat, two-dimensional configuration can have a shape such as a trapezoidal shape, and the top edge width W1 can be different than, such as, for example, smaller than, the bottom edge width W2.

As an illustrative example of a core 12 and cover blank 68 combination, a core 12 can have an anchoring element 18, a supporting element 20, and a node 22 located between the anchoring element 18 and the supporting element 20. In the deployed/radially expanded configuration, the anchoring element 18 of the core 12 can have a radial diameter of about 32 mm±1 mm, the supporting element 20 can have a radial diameter of about 41 mm±1 mm, and the length of the core 12 can be about 42 mm±1 mm. The cover blank 68 for such a core 12, can have a trapezoidal configuration and can have the following initial dimensions when viewed in a flat, two-dimensional configuration, and prior to the enclosure of the core 12: a longitudinal length L1 of about 100 mm±1 mm, a top edge width W1 of about 50 mm±1 mm, and a bottom edge width W2 of about 61 mm±1 mm.

As another illustrative example of a core 12 and cover blank 68 combination, a core 12 can have an anchoring element 18, a supporting element 20, and a node 22 located between the anchoring element 18 and the supporting element 20. In the deployed/radially expanded configuration, the anchoring element 18 of the core 12 can have a radial diameter of about 32 mm±1 mm, the supporting element 20 can have a radial diameter of about 50 mm±1 mm, and the length of the core 12 can be about 37 mm±1 mm. The cover blank 68 for such a core 12, can have a trapezoidal configuration and can have the following initial dimensions when viewed in a flat, two-dimensional configuration, and prior to the enclosure of the core 12: a longitudinal length L1 of about 100 mm±1 mm, a top edge width W1 of about 50 mm±1 mm, and a bottom edge width W2 of about 80 mm±1 mm.

It is to be understood that as the cover blank 68 undergoes the processing steps described herein, the size dimensions of the cover blank 68 can change, such as, for example, become smaller than the initial dimensions of the cover blank 68. For example, the cover blank 68 may have initial size dimensions, such as an initial longitudinal length L1. As the cover blank 68 is further processed, such as, for example, at least one edge, such as top edge 76, of layers 70 and 80 being bonded together and/or the removal of trim waste, the resultant longitudinal length of the cover blank 68 at the time of insertion of the core 12 within the cover blank 68, enclosure of the core 12 within the cover blank 68, and/or final seaming of the cover blank 68 may be smaller than the initial longitudinal length L1.

During the manufacturing process the cover 14 can be manipulated to assume the desired configuration dependent upon the desired configuration of the core 12. The cover 14, therefore, can be conformed to the core 12. As described herein, the core 12 can have a node 22 located between the anchoring element 18 and the supporting element 20. In an embodiment in which the core 12 is symmetrical about both the longitudinal axis 24 of the core 12 and the lateral axis located at the midpoint of the longitudinal axis 24 of the core 12, the node 22 can be located at the midpoint of the longitudinal axis 24 of the core 12. In an embodiment in which the core 12 is symmetrical about the longitudinal axis 24 of the core but not symmetrical about the lateral axis located at the midpoint of the longitudinal axis 24 of the core 12, the node 22 may not be located at the midpoint of the longitudinal axis 24 of the core 12. In such an embodiment, the supporting arms 28 can be longer than the anchoring arms 26 and the node 22 can be closer to the anchoring tips 30 of the core 12 and further from the supporting tips 32 of the core 12. In either embodiment, the cover 14 can be conformed to the desired configuration of the core 12 by cinching the cover 14 in the area where the node 22 of the core 12 is located.

To enclose a core 12 within the cover blank 68, the cover blank 68 can be converted from a flat, two-dimensional configuration to a three-dimensional configuration to provide a space between the two layers, 70 and 80, of material 90 of the cover blank 68 within which to insert the core 12. The process of converting the cover blank 68 from a two-dimensional configuration to a three-dimensional configuration can include loading the cover blank 68 onto a first pallet which can have prongs, 124 and 126, to open the cover blank 68. An exemplary embodiment of a first pallet 120 which can have prongs, 124 and 126, can be illustrated in FIGS. 21-23.

Figure 21:
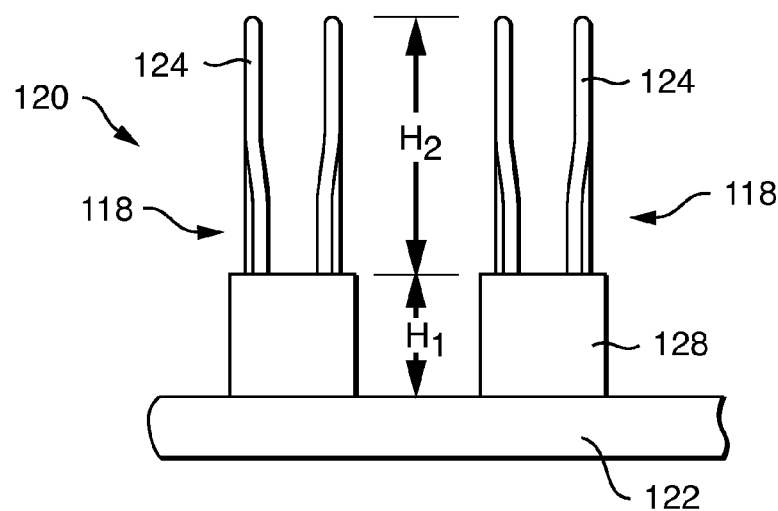
FIG. 21 is a front view of a portion of an exemplary embodiment of a first pallet onto which a cover blank can be loaded.
Figure 22:
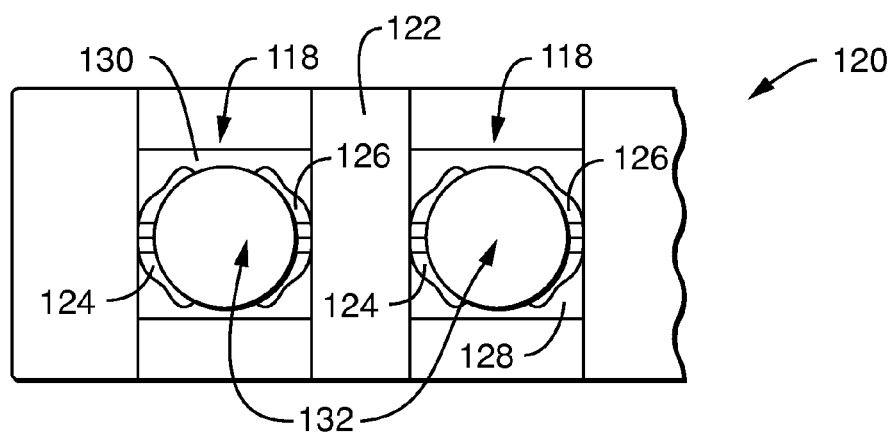
FIG. 22 is a top view of a portion of the first pallet of FIG. 21.
Figure 23:
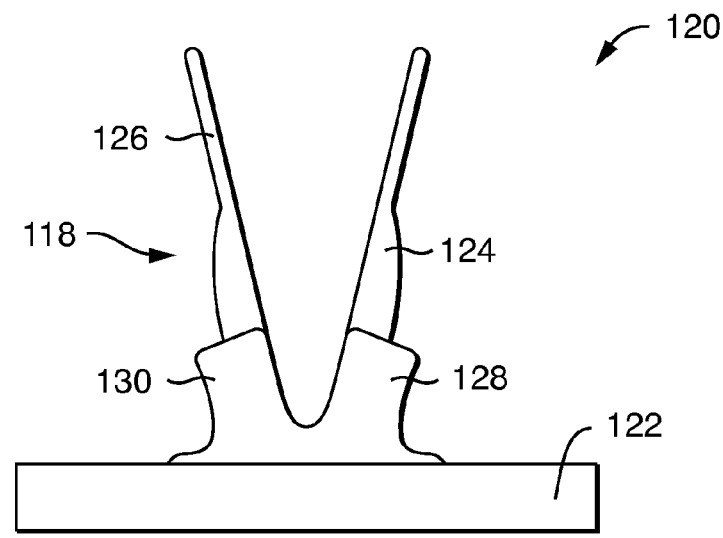
FIG. 23 is a side view of a portion of the first pallet of FIG. 21.

FIG. 21 provides an illustrative example of a front view of a portion of a first pallet 120 with a base 122 and a location 118 whereupon a cover blank 68 can be loaded. FIG. 22 provides a top view of a first pallet 120 with at least a location 118 whereupon a cover blank 68 can be loaded. FIG. 23 provides a side view of a first pallet 120 with a location 118 whereupon a cover blank 68 can be loaded. It is to be noted that the first pallet 120 can have as many locations 118 as are desired for loading cover blanks 68 for conversion from a two-dimensional configuration to a three-dimensional configuration. In various embodiments, the first pallet 120 can have at least 1, 2, 3, 4, 5, 6, 7, 8, 9, or 10 locations 118 for receiving a two-dimensional cover blank 68 for conversion to a three-dimensional cover blank 68. In various embodiments, a first pallet 120 can have from about 1, 2, 3, 4 or 5 locations 118 to about 6, 7, 8, 9 or 10 locations 118.

Referring to FIGS. 21-23, each location 118 on a first pallet 120 can have a pair of mounting brackets, such as mounting brackets 128 and 130. Each of the mounting brackets, 128 and 130, can be manufactured from any material deemed suitable such as, but not limited to, steel, aluminum, plastic, etc. The mounting brackets, 128 and 130, can have the ability to transition from a closed configuration (illustrated in FIG. 22) to an open configuration (illustrated in FIG. 23). The mounting brackets, 128 and 130, can be hingedly connected with each other such that the movement of one mounting bracket, such as mounting bracket 128, can cause movement of the other mounting bracket, such as mounting bracket 130. For example, causing mounting bracket 128 to transition from a closed configuration to an open configuration, such as, for example, by pressing on the base of mounting bracket 128, can result in mounting bracket 130 completing the same transition. Each mounting bracket, 128 and 130, can be operatively connected with the first pallet 120 in any manner deemed suitable to enable the transition from a closed configuration to an open configuration such as, for example, through the use of a hinge. Each mounting bracket, 128 and 130, can have, on its respective inward-facing side, a hemispherical shape, such that when the two mounting brackets, 128 and 130, can be brought together in a closed configuration, such as illustrated in FIG. 22, the two hemispheres can form a complete circle around an open area 132. Each of the mounting brackets, 128 and 130, can have a height H1 which can be any height deemed suitable for the manufacturing process described herein.

Referring to FIGS. 21-23, each mounting bracket, 128 and 130, can be associated with a pair of prongs, 124 and 126. For example, mounting bracket 128 can be associated with a pair of prongs 124 and mounting bracket 130 can be associated with a pair of prongs 126. The pairs of prongs, 124 and 126, can each have a base portion which can be associated with the inward-facing side of each mounting bracket, 128 and 130, respectively. The base portion of each pair of prongs, 124 and 126, can be associated with its respective mounting bracket, 128 and 130, through any manner deemed suitable, such as, for example, welding or the use of screws. Each pair of prongs, 124 and 126, can each have a portion which can extend beyond the height H1 of the mounting brackets, 128 and 130, such that the cover blank 68 can be mounted onto the portions of the pairs of prongs, 124 and 126, which extend beyond the mounting brackets, 128 and 130.

In various embodiments, each pair of prongs, such as prongs 124, can be two separate components associated with the same respective mounting bracket, such as mounting bracket 128. In such embodiments, each location 118 on first pallet 120 can have two mounting brackets, 128 and 130, and four individual prongs each having its own base associated with its respective mounting bracket, 128 and 130 (e.g., two individual prongs 124, each prong 124 associated with mounting bracket 128 and two individual prongs 126, each prong 126 associated with mounting bracket 130). In various embodiments, each pair of prongs, such as prongs 124, can be manufactured from a single material and shaped into a configuration such that the two prongs, such as prongs 124, extend from the same base of material. In such embodiments, each location 118 on first pallet 120 can have two mounting brackets, 128 and 130, and four individual prongs wherein two prongs 124 extend from a single common base associated with mounting bracket 128 and two prongs 126 extend from a single common base associated with mounting bracket 130.

As described above, the mounting brackets, 128 and 130, can each have a hemispherical shape on their inward-facing sides such that when the mounting brackets, 128 and 130, are in a closed configuration the hemispherical shapes can form a complete circle surrounding an open area 132. The base material of the prongs, 124 and 126, can be configured such that they follow the same curvature of the mounting brackets, 128 and 130. It is to be noted that the inward-facing side of the mounting brackets, 128 and 130, need not be a hemispherical shape to form a complete circle and an open area 132. The open area 132 can allow for the passage of various rods, such as push rods, and/or pre-tuck bars, through the pallets (first, second, and third pallets described herein). The open area within each of the pallets can be any shape deemed suitable to allow the passage of the various rods. In various embodiments, the open area can be circular, square, overall, and rectangle, etc. The shape of the open area can be defined by the pallet, such as, for example, the shape of open area 132 can be defined by the inward-facing side of the mounting brackets, 128 and 130.

The prongs, 124 and 126, can be manufactured from any material deemed suitable, such as, but not limited to, steel, plastic, aluminum, etc. The prongs, 124 and 126, can have any shape and configuration as deemed suitable which can allow the prongs, 124 and 126, to open and close and to hold the cover blank 68 during the conversion from a flat, two-dimensional cover blank 68 to a three-dimensional cover blank 68 and during the provision of an additional seam to the cover blank 68. During this process, the prongs, 124 and 126, should not impede any other activity or process step in the manufacturing process. In various embodiments, the prongs, 124 and 126, can be mirror images of each other. The prongs, 124 and 126, can each have a height H2 extending beyond the mounting brackets, 128 and 130. The height H2 of the prongs, 124 and 126, can be less than the overall initial longitudinal length L1 of the cover blank 68 such that the prongs, 124 and 126, may not interfere with further processing of the cover blank 68, such as, for example, the bonding of the bottom edges 78 of layers 70 and 80 of the cover blank 68.

As noted above, the mounting brackets, 128 and 130, can transition from a closed configuration, such as in FIG. 22, to an open configuration, such as in FIG. 23. As the prongs, 124 and 126, can each have a base associated with the mounting brackets, 128 and 130, the prongs, 124 and 126, can undergo the same transition in configuration (i.e., from a closed configuration to an open configuration). Referring to FIG. 22, the mounting brackets, 128 and 130, can be in a closed configuration. The bases of the prongs, 124 and 126, can be associated with the mounting brackets, 128 and 130, in such a way as to enable the portion of the prongs, 124 and 126, extending beyond the mounting brackets, 128 and 130, to be in close proximity with each other when the mounting brackets, 128 and 130, are in a closed configuration. In various embodiments, the prongs 124 and 126 can contact each other (e.g, a prong 124 contacting a prong 126) when the mounting brackets, 128 and 130, are in a closed configuration. Referring to FIG. 23, when the mounting brackets, 128 and 130, have transitioned to an open configuration, the portion of the prongs, 124 and 126, extending beyond the mounting brackets, 128 and 130, can also transition to an open configuration and the prongs, 124 and 126, can move directionally away from each other. This movement of the prongs, 124 and 126, away from each other can cause the cover blank 68 to convert from a flat, two-dimensional configuration to an open, three-dimensional configuration as the movement of the prongs, 124 and 126, away from each other can force the layers, 70 and 80, of the cover blank 68 away from each other.

As described above, in various embodiments, a ribbon 112 of cover blanks 68 can be manufactured. In various embodiments, such as the embodiment illustrated in FIG. 18, the cover blanks 68 in a ribbon 112 of cover blanks 68 can have a trapezoidal configuration and the top edges 76 of layers 70 and 80 of two cover blanks 68 can be adjacent each other and the bottom edges 78 of layers 70 and 80 of two cover blanks 68 can be adjacent each other. As described above, it is believed this arrangement can provide for better efficiency in the removal of areas of trim 102 as trim waste 110. In order to convert each individual cover blank 68 from a two-dimensional configuration to a three-dimensional configuration, an individual cover blank 68 can be separated from the ribbon 112 of cover blanks 68 and loaded onto a first pallet 120 at a location 118 having prongs, 124 and 126.

In various embodiments, it may be desirable to bond the bottom edges 78 of layers 70 and 80 of the cover blank 68 following the loading of the cover blank 68 onto the first pallet 120. Bonding of the bottom edges 78 of layers 70 and 80 of the cover blank 68 can form a bond area 168 which can ultimately form a seam, such as supporting element seam 174, which can be located near the supporting element 20 of a core 12. In such embodiments, the cover blank 68 can be loaded onto the first pallet 120 such that the top edges 76 of layers 70 and 80 of the cover blank 68 are closest to the mounting brackets, 128 and 130, and the bottom edges 78 of layer 70 and 80 of the cover blank 68 are closest to the uppermost portion of the prongs, 124 and 126. The cover blank 68 can have an initial longitudinal length L1 greater than the height H2 of the portion of the prongs, 124 and 126, extending beyond the mounting brackets, 128 and 130. A portion of the cover blank 68 extending beyond the height H2 of the prongs, 124 and 126, can be bonded together to form bond area 168 which can ultimately form a seam such as the supporting element seam 174 of cover 14.

Figure 24:
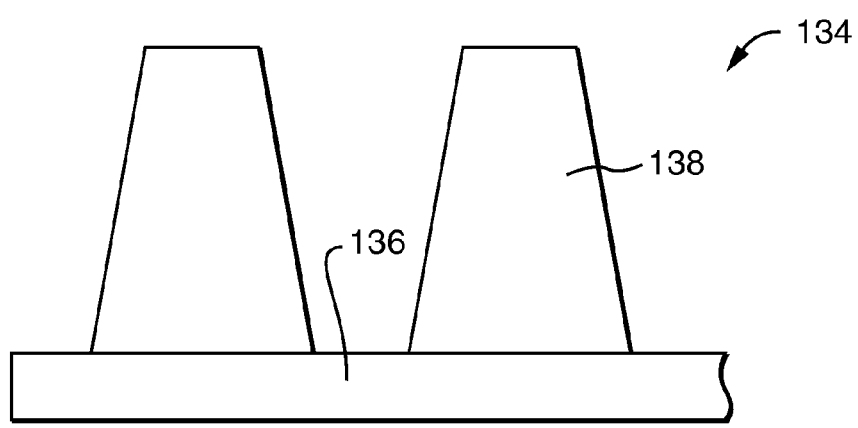
FIG. 24 is a front view of a portion of an exemplary embodiment of a loading fixture onto which a cover blank can be loaded.
Figure 25:
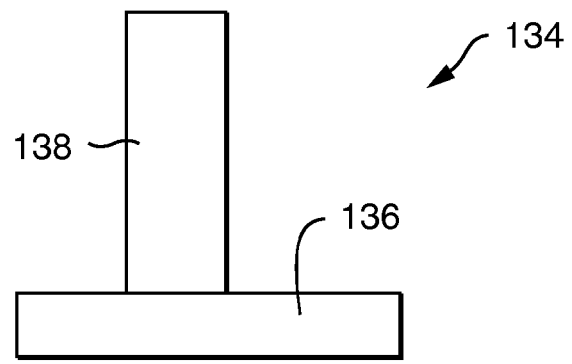
FIG. 25 is a side view of a portion of the loading fixture of FIG. 24.

As noted above, the cover blanks 68 can be manufactured in a ribbon 112 of cover blanks 68 wherein the top edges 76 of two sequential cover blanks 68 can be adjacent to each other and the bottom edges 78 of two sequential cover blanks 68 can be adjacent to each other. As such, the cover blanks 68 can be said to be manufactured in an alternating sequence of cover blanks 68. As the cover blanks 68 can be in an alternating sequence in the ribbon 112 of cover blanks 68, every other cover blank 68 in the ribbon 112 may be in a ready configuration to be loaded on the first pallet 120 by placing the top edges 76 of the layers 70 and 80 of the cover blank 68 closest to the mounting brackets, 128 and 130, on the first pallet 120. To provide for efficiency in the manufacturing operation, the alternating cover blank 68 which may not be in a ready configuration to load on the first pallet 120 can be placed onto a cover blank 68 loading fixture 134 such as illustrated in FIGS. 24 and 25. FIG. 24 provides a front view of a cover blank 68 loading fixture 134 and FIG. 25 provides a side view of a cover blank 68 loading fixture 134. The cover blank 68 loading fixture 134 can have a fixture base 136 and a cover blank 68 support 138. As described above, in various embodiments, the cover blank 68 can have a trapezoidal configuration. As the cover blank 68 can have a trapezoidal configuration, the cover blank 68 support 138 can also have a trapezoidal configuration. The cover blank 68 loading fixture 134 can provide an alternative location for the loading of cover blanks 68 which may not be in ready configuration when separated from the ribbon 112 of cover blanks 68 to be loaded onto the first pallet 120.

Figure 26:
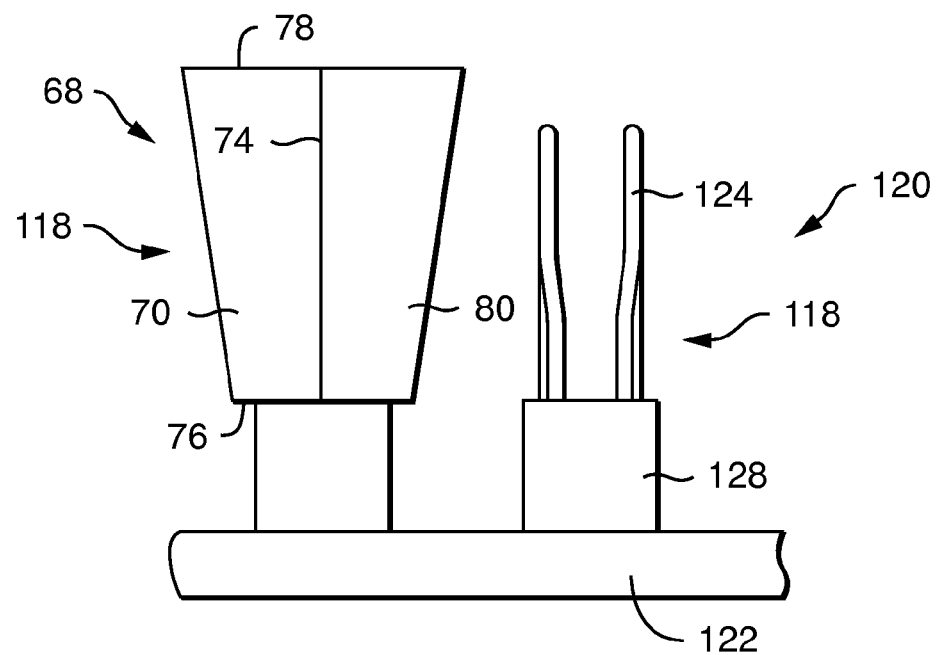
FIG. 26 is a front view of an exemplary embodiment of a cover blank loaded onto a portion of a first pallet.
Figure 27:
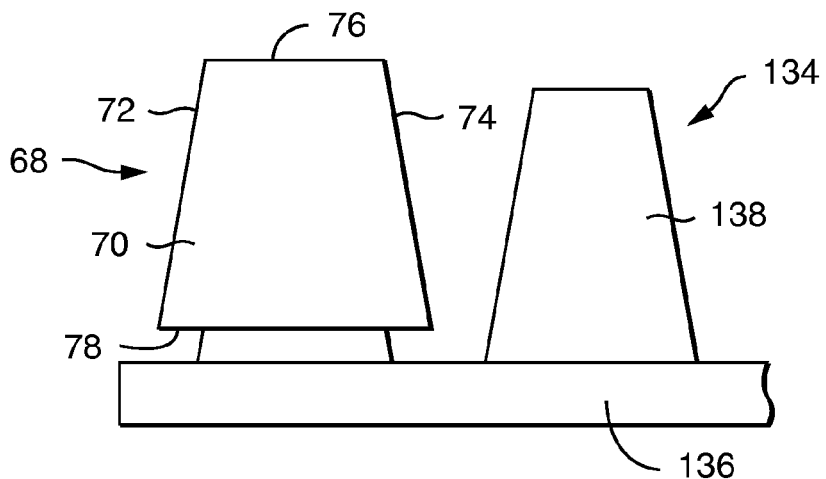
FIG. 27 is a front view of an exemplary embodiment of a cover blank loaded onto a portion of a loading fixture.
Figure 28:
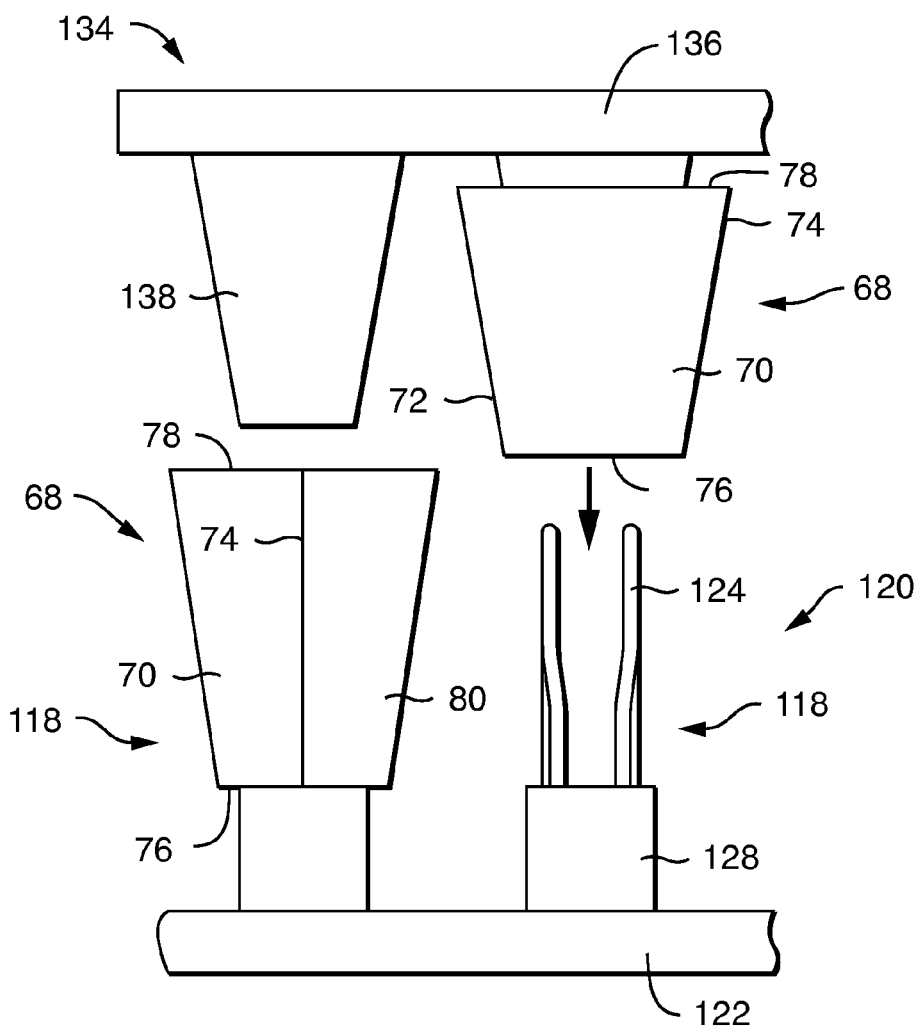
FIG. 28 is a front view of an exemplary embodiment of a process of loading a first pallet with a cover blank which was previously loaded on a loading fixture.

Referring to FIGS. 26-28, the loading of a cover blank 68 onto a first pallet 120 and a cover blank 68 onto a cover blank 68 loading fixture 134 can be illustrated. In an embodiment, a cover blank 68 can be considered to be in ready configuration for loading on the first pallet 120 when, at the time the cover blank 68 can be separated from the ribbon 112 of cover blanks 68, the cover blank 68 can be connected to the ribbon 112 of cover blanks 68 via the bottom edge 78 of layers 70 and 80, of the cover blank 68 and the top edges 76 of layers 70 and 80 are the leading edge of the ribbon 112 of cover blanks 68. In such an embodiment, the cover blank 68 can be separated from the ribbon 112 by breaking the perforations 106 between the connected bottom edges 78 of the cover blank 68 in the ribbon 112 and the next adjacent cover blank 68 in the ribbon 112. The separated cover blank 68 can be directly loaded onto the first pallet 120 at the first available location 118.

Referring to FIG. 26, this separated cover blank 68 can be loaded onto the first pallet 120 with the top edges 76 of layers 70 and 80 of the cover blank 68 closest to the mounting brackets, 128 and 130, and the bottom edges 78 of layers 70 and 80 of cover blank 68 extending beyond the prongs, 124 and 126. The cover blank 68 can be positioned such that the side seams, such as seam 74, are perpendicular to the plane of the first pallet 120. Positioning the cover blank 68 such that the side seam 74 can be perpendicular to the place of the first pallet 120 can include rotating, in a clockwise or counter-clockwise direction, the cover blank 68 about the prongs, 124 and 126, until the side seam 74 can be perpendicular to the plane of the first pallet 120. Positioning the side seams, such as seam 74, perpendicular to the plane of the first pallet 120 can prevent the removal element 16 from being associated with the vaginal insert 10 within the side seams, 72 and 74. If the removal element 16 is associated with the vaginal insert 10 within the side seams, 72 and 74, pulling on the removal element 16 during removal of the vaginal insert 10 from the vagina can weaken the side seams, 72 and 74, of the vaginal insert 10, which can compromise the integrity of the vaginal insert 10.

In an embodiment in which the cover blanks 68 are manufactured in a ribbon 112 with an alternating sequence of cover blanks 68 (such as illustrated in FIGS. 17 and 18), after a first cover blank 68 has been separated from the ribbon 112 and loaded onto the first pallet 120, the next adjacent cover blank 68 can be separated from the ribbon 112 and loaded onto the cover blank 68 loading fixture 134 such as illustrated in FIG. 27. As illustrated in FIG. 27, the cover blank 68 can be loaded onto a cover blank 68 support 138 with the bottom edges 78 of layers 70 and 80 closest to the base 136 of the cover blank 68 loading fixture 134. With reference to FIG. 28, to transfer the cover blank 68 from the cover blank 68 loading fixture 134 to the first pallet 120, the cover blank 68 loading fixture 134 can be rotated 180° thereby positioning the cover blanks 68 located on the cover blank 68 loading fixture 134 into the correct orientation for loading onto the first pallet 120. Cover blanks 68 which initially had the bottom edges 78 of layers 70 and 80 of the cover blank 68 as their leading edge when being separated from a ribbon 112 of cover blanks 68 now have the top edges 76 of layers 70 and 80 of the cover blank 68 as their leading edge and in the correct orientation to position the top edges 76 of layers 70 and 80 of the cover blank 68 closest to the mounting brackets, 128 and 130, of the first pallet 120.

With reference to FIGS. 17-28, in an exemplary embodiment, a first pallet 120 can have six locations 118 upon which two-dimensional cover blanks 68 can be loaded and a cover blank 68 loading fixture 134 can have six cover blank 68 supports 138 upon which two-dimensional cover blanks 68 can be loaded. In such an exemplary embodiment, the process of loading multiple cover blanks 68 from a ribbon 112 of alternating sequence cover blanks 68 (such as illustrated in FIGS. 17 and 18) onto the first pallet 120 can include the steps of alternating the loading of a cover blank 68 from the ribbon 112 onto the first pallet 120 with the top edges 76 of layers 70 and 80 closest to the mounting brackets, 128 and 130, followed by the loading of the next cover blank 68 in the ribbon 112 onto the cover blank 68 loading fixture 134 with the bottom edges 78 of layers 70 and 80 closest to the base 136 of the cover blank 68 loading fixture 134. These process steps can continue until all six positions 118 of the first pallet 120 and all six cover blank 68 supports 138 of the cover blank 68 loading fixture 134 have a loaded cover blank 68. In such an embodiment, therefore, twelve cover blanks 68 can be separated from the ribbon 112 of cover blanks 68. Once all six positions 118 of the first pallet 120 are loaded with a cover blank 68, the cover blanks 68 can be positioned such that the side seams, 72 and 74, can be perpendicular to the plane of the first pallet 120. The mounting brackets, 128 and 130, can be operated such that the mounting brackets, 128 and 130, and the prongs, 124 and 126, transition from the closed configuration to an open configuration. The transition of the mounting brackets, 128 and 130, from the closed configuration to an open configuration can be accomplished by pressing down on the base of a mounting bracket, such as mounting bracket 128, and causing it to hinge open. This movement can result in the hingedly attached mounting bracket 130 to also transition to an open configuration. The prongs, 124 and 126, in the open configuration, can push the layers, 70 and 80, of the cover blank 68 apart from each other, thereby rendering the cover blank 68 into an open configuration. The first pallet 120 having the six cover blanks 68 loaded thereupon can be moved to the next station of the manufacturing process and an "empty" first pallet 120 can be obtained (thus, another first pallet 120). The cover blank 68 loading fixture 134 can be inverted 180° over the "empty" first pallet 120 and the cover blanks 68, which had been loaded onto the cover blank 68 supports 138 of the cover blank 68 loading fixture 134, can be transferred to the "empty" first pallet 120 by sliding them off of the cover blank 68 supports 138 and down onto the prongs, 124 and 126, of the "empty" first pallet 120. Following the transfer of the six cover blanks 68 from the cover blank 68 loading fixture 134 to the "empty" first pallet 120, the cover blank 68 loading fixture 134 will be empty of cover blanks 68, the first pallet 120 which had been "empty" is now fully loaded with cover blanks 68 and can be moved to the next station of the manufacturing process, and the sequence of loading cover blanks 68 can begin again with another empty first pallet 120 and an empty cover blank 68 loading fixture 134.

The next station in the manufacturing process can include the pleating and sealing of the bottom edges 78 of layers 70 and 80 of the cover blank 68. The pleating and sealing of the bottom edges 78 of layers 70 and 80 of the cover blank 68 can result in the formation of a bond area 168 which can ultimately form a seam, such as supporting element seam 174 of the cover 14.

As described above, a cover blank 68 can be positioned on the first pallet 120 such that the top edges 76 of the layers, 70 and 80, of the cover blank 68 can be positioned closest to the mounting brackets, 128 and 130, of the first pallet 120. The bottom edges 78 of the layers, 70 and 80, of the cover blank 68 can, therefore, extend beyond the prongs, 124 and 126. The bottom edges 78 of the layers 70 and 80 can be bonded together to form a bond area 168. The bond area 168 can ultimately become supporting element seam 174 and can ultimately be located near the supporting element 20 of the core 12.

FIGS. 29-34 provide exemplary illustrations of exemplary process steps wherein the bottom edges 78 of the layers 70 and 80 of the cover blank 68 can be pleated and bonded together thereby forming bond area 168. A first pallet 120 having at least one open, three-dimensional cover blank 68 thereupon, can enter a pleater module. The cover blank 68 can be in an open configuration as the prongs, 124 and 126, of the first pallet 120 can be in an open configuration. The pleater module can pleat layers 70 and 80 together thereby forming bond area 168. The bond area 168 can ultimately become a supporting element seam 174 of a cover 14 and can be located in proximity to the supporting element 20 of a core 12 of a vaginal insert 10.

As described above with regards to FIGS. 26 and 28, a two-dimensional cover blank 68 can be loaded onto a first pallet 120 and positioned such that the side seams, 72 and 74, can be perpendicular to the plane of the first pallet 120. The first pallet 120 can be conveyed to the pleater module with the side seams, 72 and 74, of the cover blank 68 perpendicular to the plane of the first pallet 120.

Figure 29:
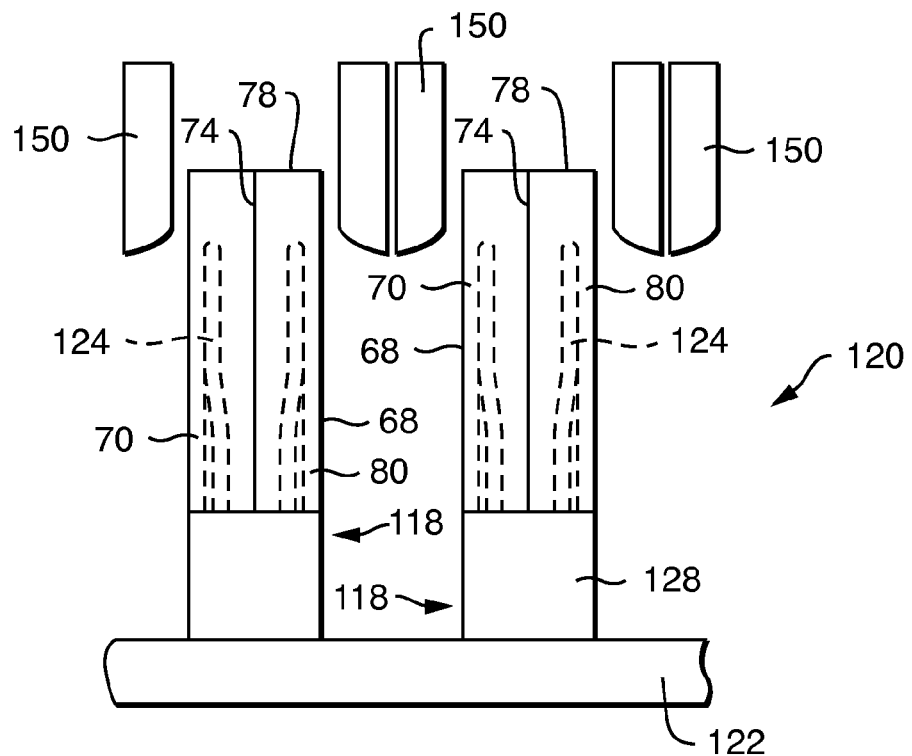
FIG. 29 is a front view of an exemplary embodiment of a portion of a first pallet with two cover blanks prior to pleating of the cover blanks.
Figure 30:
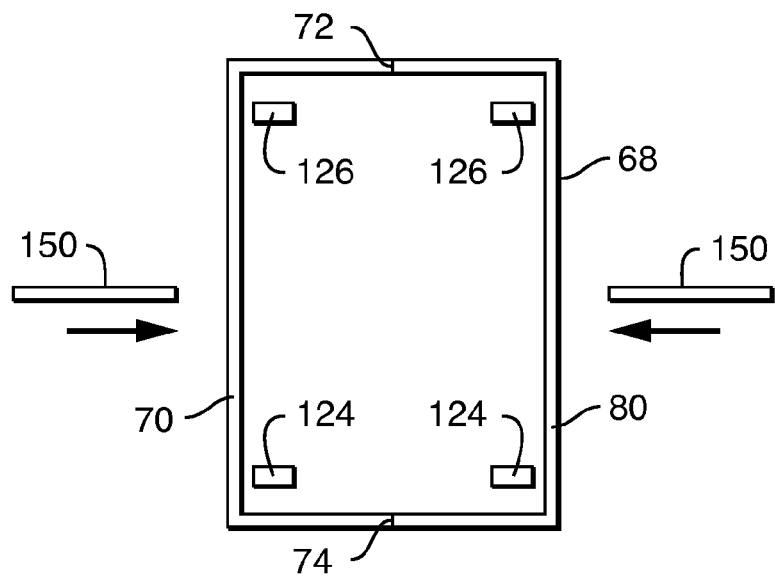
FIG. 30 is a top view of an exemplary schematic of a cover blank in an open configuration prior to pleating.

FIG. 29 provides an exemplary illustration of a portion of a first pallet 120 having a cover blank 68 loaded there-upon and held in an open configuration by pairs of opposing prongs, such as prongs 124. It is to be understood that prongs 126 cooperate with prongs 124 to hold the cover blank 68 in an open configuration, however, only prongs 124 are visible to the viewer in the illustration of FIG. 29. The pleater module can have tuck bars 150 which can operate in a paired fashion. For example, with reference to FIG. 29, two cover blanks 68 are visible in an open configuration and five tuck bars 150 are visible. The tuck bars 150 can extend past the bottom edges 78 of the open cover blanks 68 and close together to form the pleat of the layers 70 and 80 of the cover blanks 68. When the tuck bars 150 move into position in readiness to pleat a cover blank 68, a tuck bar 150 of the pair of tuck bars 150 can be positioned on one side of the cover blank 68, and the other tuck bar 150 of the pair of tuck bars 150 can be positioned on the opposite side of the cover blank 68. After the pair of tuck bars 150 have lowered into position, each tuck bar 150 moves into the side of a cover blank 68 to create a pleat. FIG. 30 provides a top view illustration of a cover blank 68 and two tuck bars 150, positioned in opposite relation to each other, in ready position to pleat the cover blank 68. The directional arrows can indicate the direction that each tuck bar 150 can move in order to provide a pleat in the cover blank 68. It should be noted that while FIG. 30 is a top view, the illustration of the first pallet 120 is not visible in FIG. 30 to provide clarity of illustration.

Figure 31:
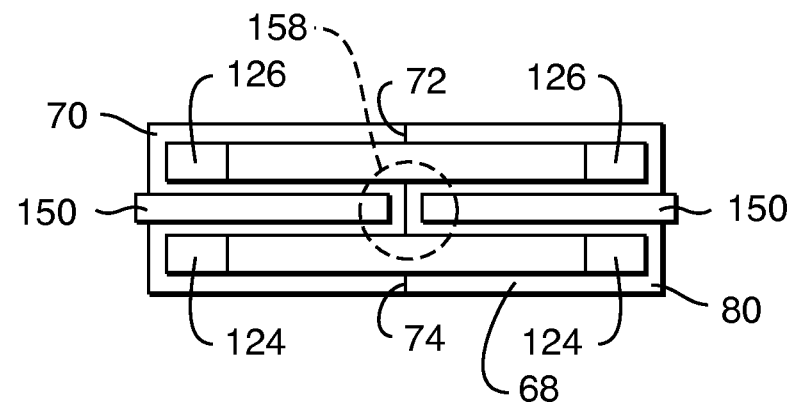
FIG. 31 is a top view of an exemplary schematic of a cover blank during pleating of the cover.
Figure 32:
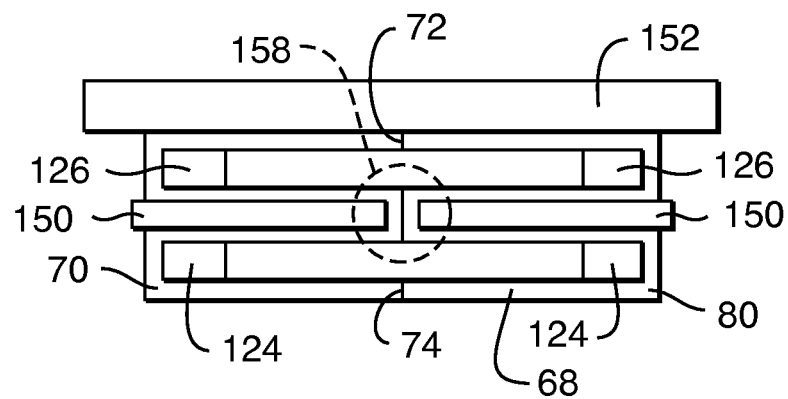
FIG. 32 is a top view of an exemplary schematic of a cover blank prior to withdrawal of the pleating bars.

As the tuck bars 150 move towards each other to create the pleats in the cover blank 68, the prongs, 124 and 126, can collapse together and clamp the cover blank 68 to keep the pleats from pulling out. The pleated cover blank 68, when viewed in a top view, can resemble an "H" configuration. FIG. 31 provides a top view of the "H" configuration of the cover blank 68 after the pair of tuck bars 150 have pleated layers 70 and 80 of the cover blank 68 and the prongs, 124 and 126, have transitioned from the open configuration to a closed configuration. Referring to FIG. 32, it can be seen that a holder bar 152 can be moved into position next to the pleated cover blank 68 to maintain the pleated cover blank 68 in the pleated "H" configuration and/or to ensure that the prongs, 124 and 126, have collapsed together before the tuck bars 150 are withdrawn. The tuck bars 150 can be withdrawn and the pleated cover blank 68 can be conveyed to a bonding assembly for bonding of the pleated layers 70 and 80. The holder bar 152 can also be withdrawn prior to, during, or after conveyance of the first pallet 120 to the bonding assembly. The bonding of the pleated layers, 70 and 80, of the cover blank 68 can bond at least two layers of material together. In various embodiments, as the pair of tuck bars 150 can fold layers 70 and 80 inwards and towards each other, the bonding can be effected through at least four layers of material. FIGS. 31 and 32 can each provide an illustration of the four layers of material of layers 70 and 80 of the cover blank 68 that can be bonded together to form the bond area 168. Also visible in FIGS. 31 and 32 is a pleat center 158 within the "H" configuration. The pleat center 158 can be the location of the pleated cover blank 68 wherein material of layers 70 and 80 can be brought into close proximity with each other as a result of the movement of the tuck bars 150. In various embodiments, there can be less than a 10 mm gap between the material of layers 70 and 80 in the pleat center 158. In various embodiments, there can be from about 0, 1, 2, 3, 4, or 5 mm to about 6, 7, 8, 9, or 10 mm gap between the material of layers 70 and 80 in the pleat center 158.

Figure 33:
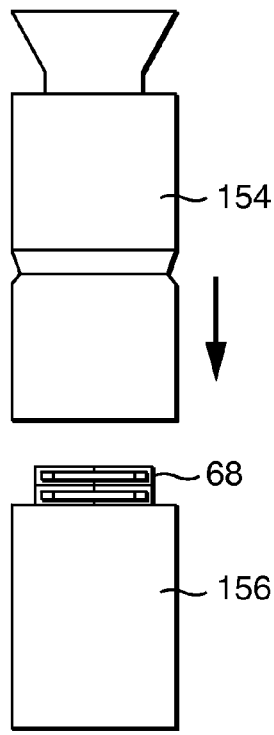
FIG. 33 is a top view of an exemplary schematic of a pleated cover blank in position for bonding.

FIG. 33 provides a top view of a pleated cover blank 68 within a bonding assembly. The bonding can occur by any means deemed suitable such as, but not limited to, adhesive, pressure bonding, thermal bonding, ultrasonic bonding, stitching, suturing, and/or welding. In the exemplary embodiment illustrated in FIG. 33, the pleated cover blank 68 can be subjected to ultrasonic bonding to create a bond area 168 (shown in FIG. 34). Ultrasonic bonders can have an internal solenoid valve that can move the horn into and out of position when the bonding cycle has been triggered. Any ultrasonic horn 154 and anvil 156 deemed suitable can be utilized to form the bond area 168.

Figure 34:
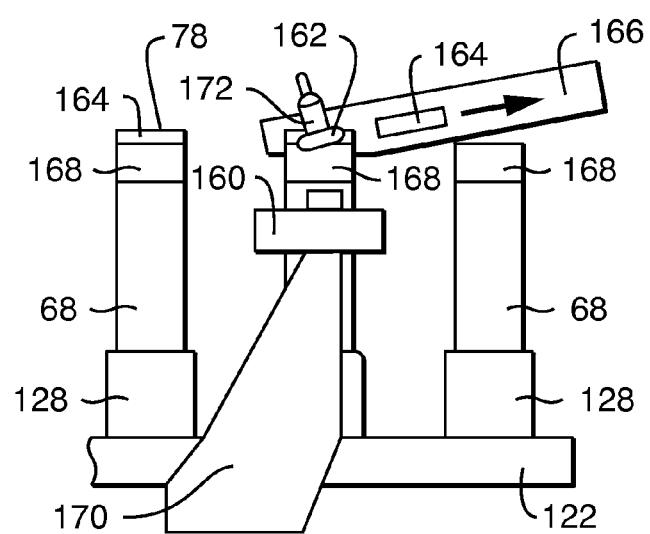
FIG. 34 is a side view of an exemplary schematic of an exemplary process to remove an area of trim from a cover blank.

Once the bonding of each of the cover blanks 68 on the first pallet 120 is completed, the first pallet 120 can be advanced to a trim removal station. FIG. 34 provides an illustration of an exemplary embodiment of a trim removal station. The bonding of layers 70 and 80 of the cover blank 68 can occur in the area of the layers 70 and 80 which extends beyond the height H2 of the prongs, 124 and 126. In various embodiments, all of the material of layers 70 and 80 of the cover blank 68 extending beyond the height H2 of the prongs, 124 and 126, can be bonded together to create a bond area 168. In various embodiments, less than all of the material of layers 70 and 80 of the cover blank 68 extending beyond the height H2 of the prongs, 124 and 126, can be bonded together to create a bond area 168. In such embodiments, an area of trim 164 can be located between the bond area 168 and the bottom edges 78 of the layers 70 and 80 of the cover blank 68. The area of trim 164 can be removed in a trim removal station. As the first pallet 120 can advance through the trim removal station, a trim wheel 162, such as trim wheel 162 suspended from a support bracket 172, can nip the area of trim 164 and pull the area of trim 164 upwards to separate the area of trim 164 from the bond area 168. In various embodiments, the trim wheel 162 can be a pair of friction wheels. The area of trim 164 can be further pulled away from the bonded area 168 by any means deemed suitable, such as, for example, a vacuum 166. The hold down rollers 160 can prevent the cover blank 68 from being pulled off of the prongs, 124 and 126. The hold down rollers 160 can be suspended from a mounting bracket 170.

Following the pleating and bonding of edges 78 of layers 70 and 80 of a cover blank 68, the cover blank 68 can have a single opening wherein a portion of at least one edge of layers 70 and 80 remains unbonded. A core insertion module 180 can insert a core 12 into the cover blank 68 through the opening of the cover blank 68. In various embodiments, inserting the core 12 into the cover blank 68 can be simply moving the core 12 through the opening and into the space between layers 70 and 80 of the cover blank 68. In such embodiments, the supporting element seam 174 can be on an external surface of the cover 14. In various embodiments, inserting the core 12 into the cover blank 68 can include the steps of inverting the cover blank 68 and then moving the core 12 through the opening and into the open space between layers 70 and 80 of the cover blank 68. In such embodiments, the supporting element seam 174 can be located on an internal vaginal insert 10 surface. In various embodiments, inserting the core 12 into the cover blank 68 can include the step of inverting the cover blank 68 over and onto the core 12 at the same time as the core 12 is being moved through the opening and into the space between layers 70 and 80 of the cover blank 68. During the process of inserting a core 12 into the cover blank 68, the core insertion module 180 can also transfer the core 12 and cover blank 68 combination to a second pallet 188.

Figure 35:
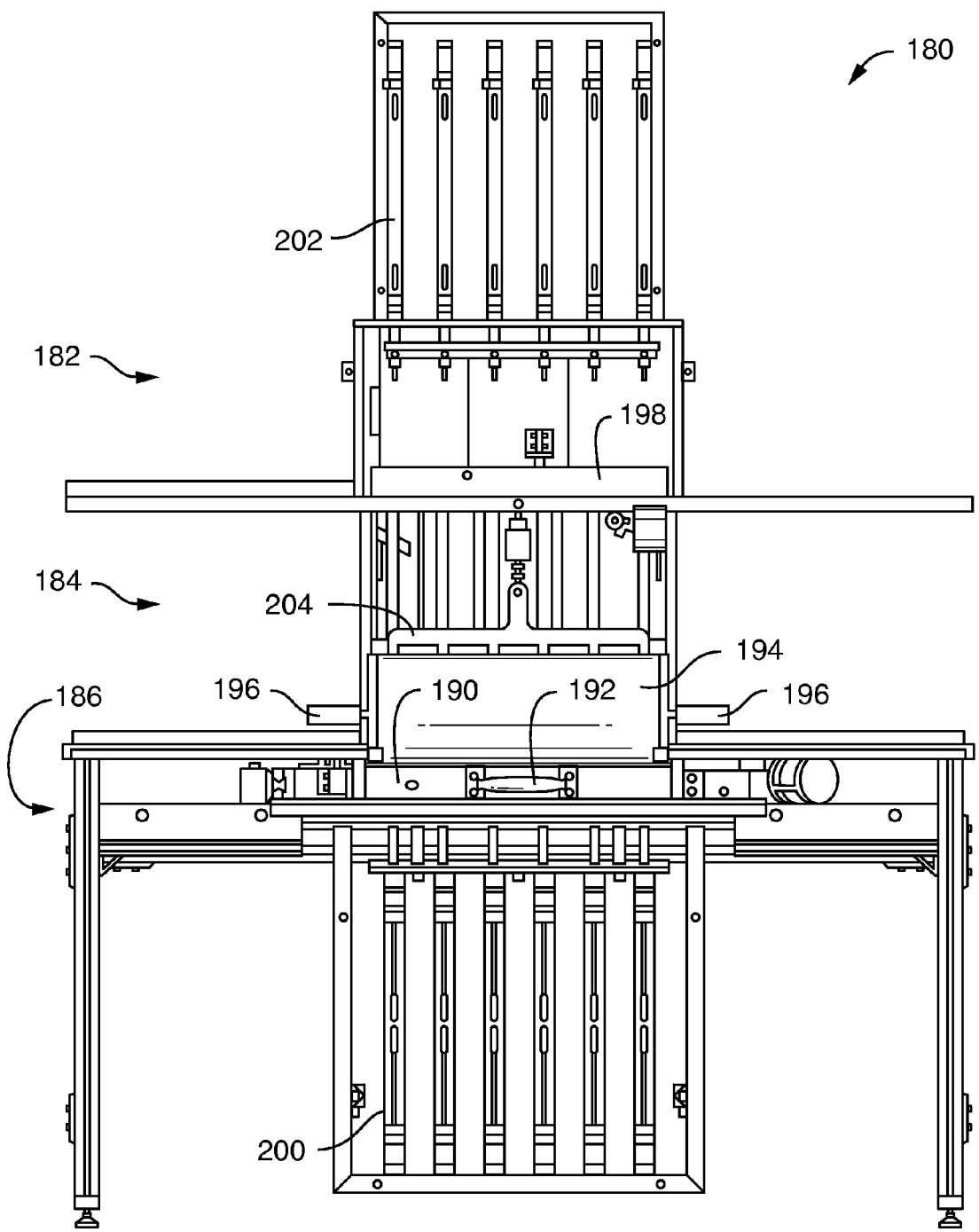
FIG. 35 is a front view of an exemplary embodiment of a core insertion module.

FIG. 35 provides a front view illustration of an exemplary embodiment of a core insertion module 180. The core insertion module 180 can receive a core 12 in a core compression tray 190, transfer the core 12 from the core compression tray 190 into the cover blank 68 (provided on a first pallet 120) and position the core 12 and cover blank 68 combination in a second pallet 188. The transfer of the core 12 from the core compression tray 190 into a cover blank 68 can include inserting the core 12 into the cover blank 68 via any of the insertion methods described above. Once such insertion method—inverting the cover blank 68 at the same time as moving the core 12 into the cover blank 68—can be further described herein. To accomplish the insertion of the core 12 within the cover blank 68 and the transfer of the core 12 and cover blank 68 combination to a second pallet 188, the core insertion module 180 can have three primary levels. A top level 182 can provide a location wherein a second pallet 188 can be loaded for receipt of the core 12 and cover blank 68 combination following insertion of the core 12 into the cover blank 68. The top level 182 can include a table 198 upon which the second pallet 188 can be positioned. In various embodiments, the table 198 can move in an up and down motion within the core insertion module 180. For example, the table 198, with a second pallet 188 positioned thereupon can lower to the middle level 184 of the core insertion module 180 to be in closer proximity to the first pallet 120, which can be positioned within the middle level 184 of the core insertion module. The top level 182 can also include pre-tuck rods 202 which can provide an initial tucking of a cover blank 68 onto the core 12. A middle level 184 can include a barrel drum 194 and a barrel drum handle 196. A first pallet 120 can be positioned within the barrel drum 194 and the barrel drum handle 196 can be used to rotate the barrel drum 194 to invert the first pallet 120. The first pallet 120 can have at least one cover blank 68 positioned thereupon. The cover blank 68 can have side seams, 72 and 74, and supporting element seam 174. The cover blank 68 can have an opening between the top edges 76 of layers 70 and 80 of the cover blank 68. The top edges 76 of the layers 70 and 80 can be positioned next to the mounting brackets, 128 and 130, of a location 118 of the first pallet 120. The middle level 184 can also include a core set tool 204 which can be used to set a core 12 into the core compression tray 190. The core 12 can be placed into an opening 220 in the core compression tray 190 and the core set tool 204 can be used to push the core 12 further into the opening 220 such that the core 12 can be positioned below the top surface 224 of the core compression tray 190. The core set tool 204 can help to maintain a uniform depth of core(s) 12 loaded into the core compression tray 190. The lower level 186 can include the core compression tray 190. A core 12 can be placed into an opening of the core compression tray 190 and thereby readied for insertion into a cover blank 68. The core compression tray 190 can have a handle 192 which can be used to move the core compression tray 190 between an open and closed configuration. The lower level 186 can also include push rods 200 which can push the core 12 upwards into the cover blank 68 and further into the second pallet 188.

Figure 36:
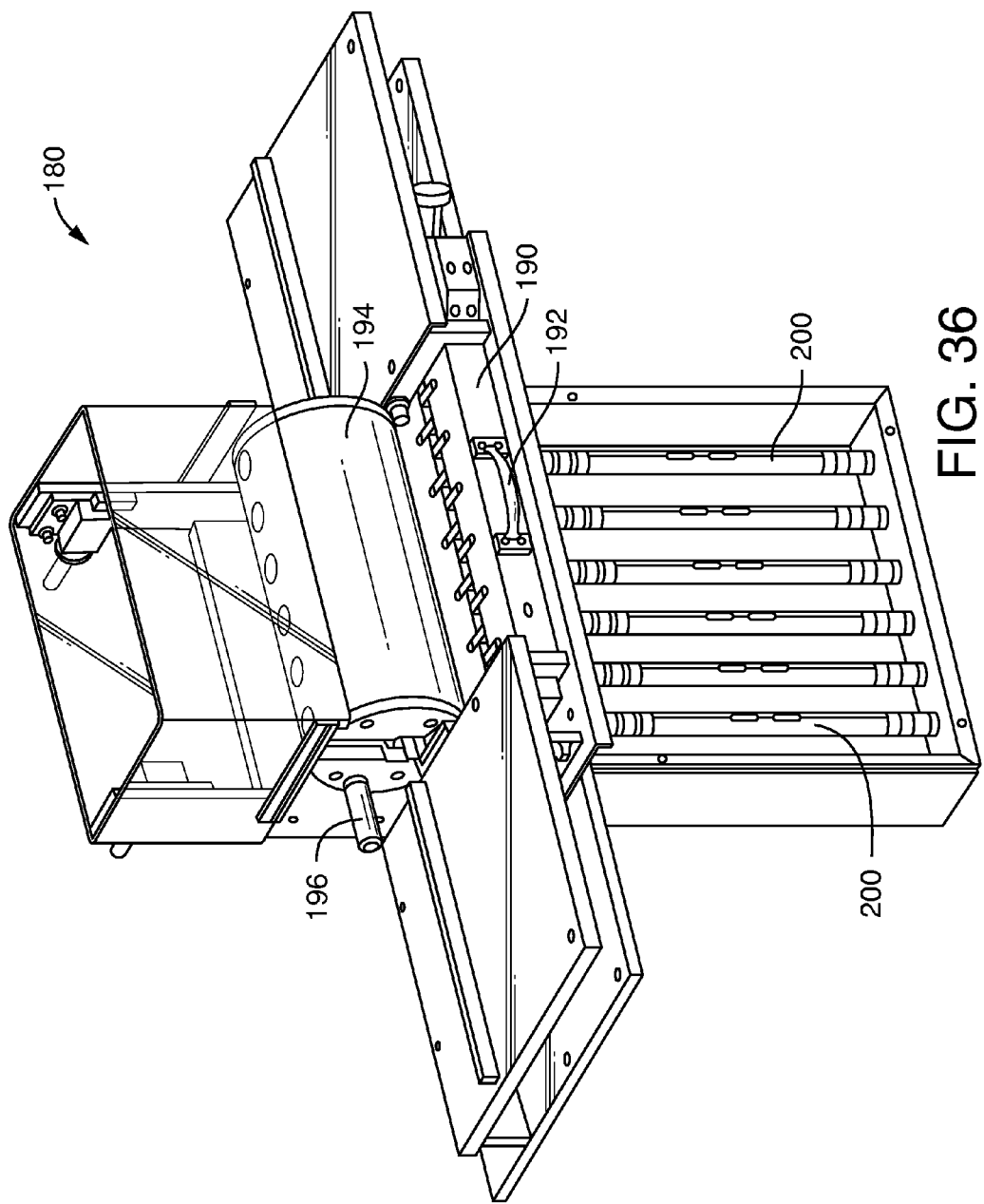
FIG. 36 is a perspective view of an exemplary embodiment of the middle and lower levels of a core insertion module wherein the barrel drum and the core compression tray can be in open positions.
Figure 37:
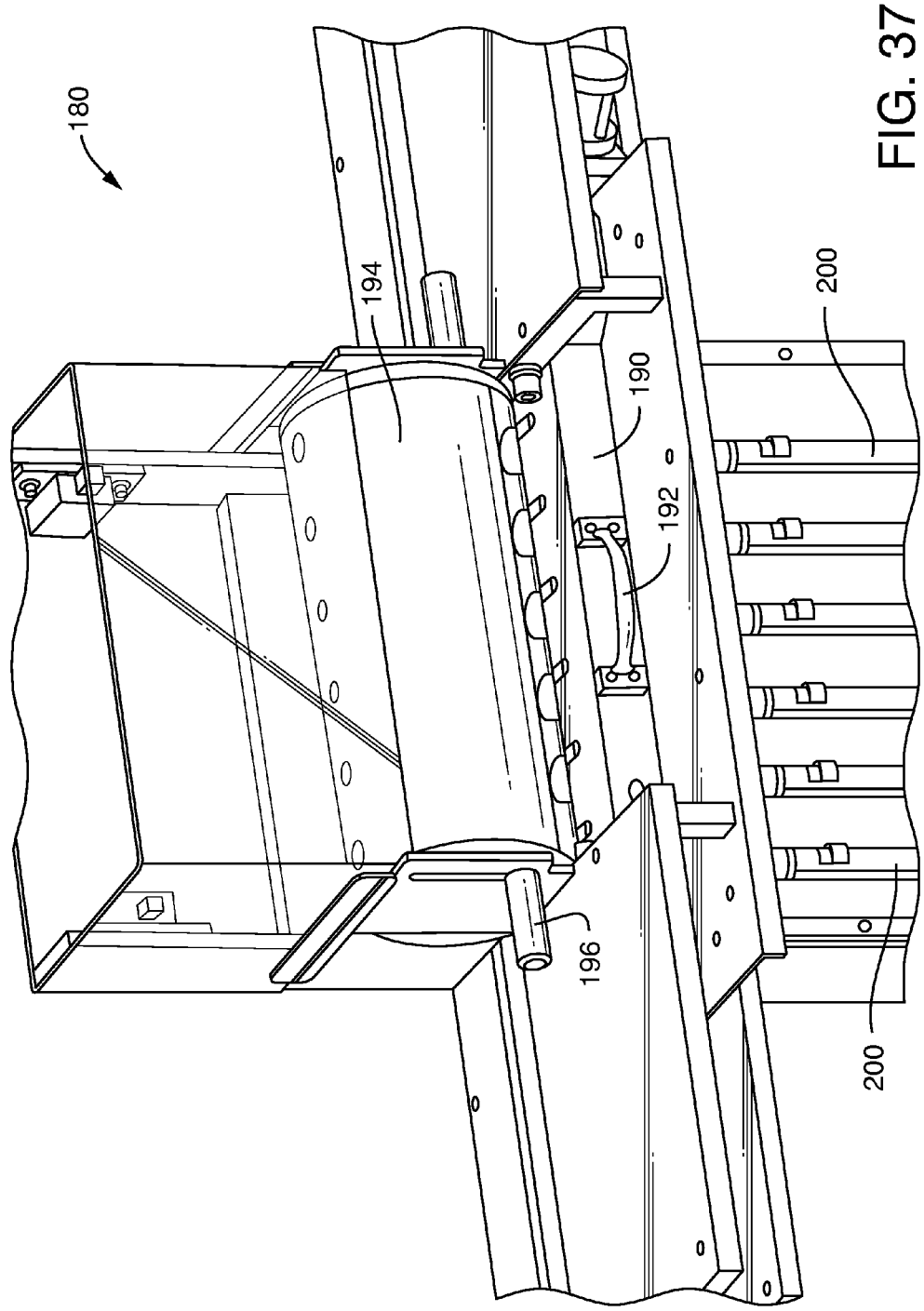
FIG. 37 is a perspective view of an exemplary embodiment of the middle and lower levels of a core insertion module wherein the barrel drum and the core compression tray can be in closed positions.
Figure 38A:
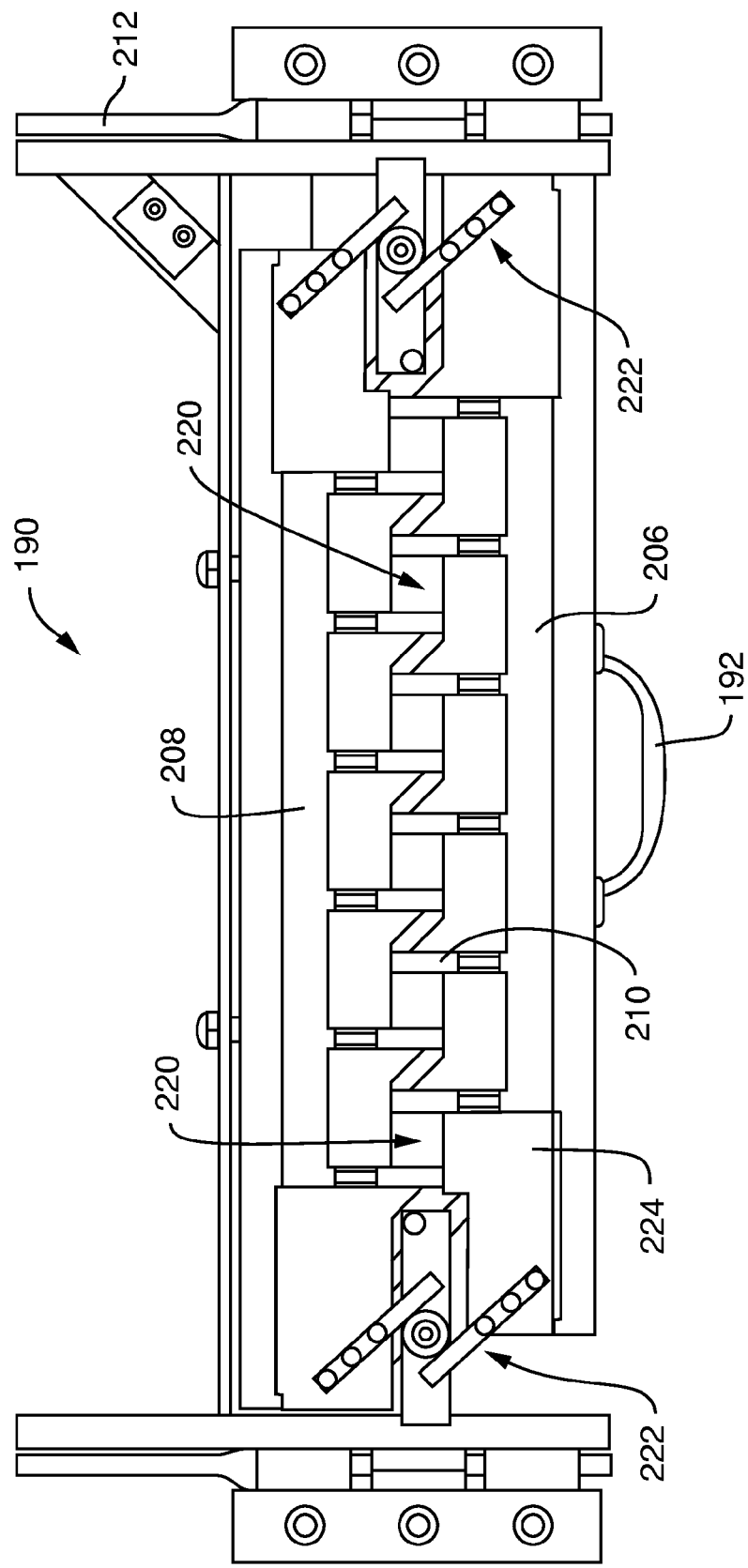
FIGS. 38A and 38B are perspective views of exemplary embodiments of a core compression tray.
Figure 38B:
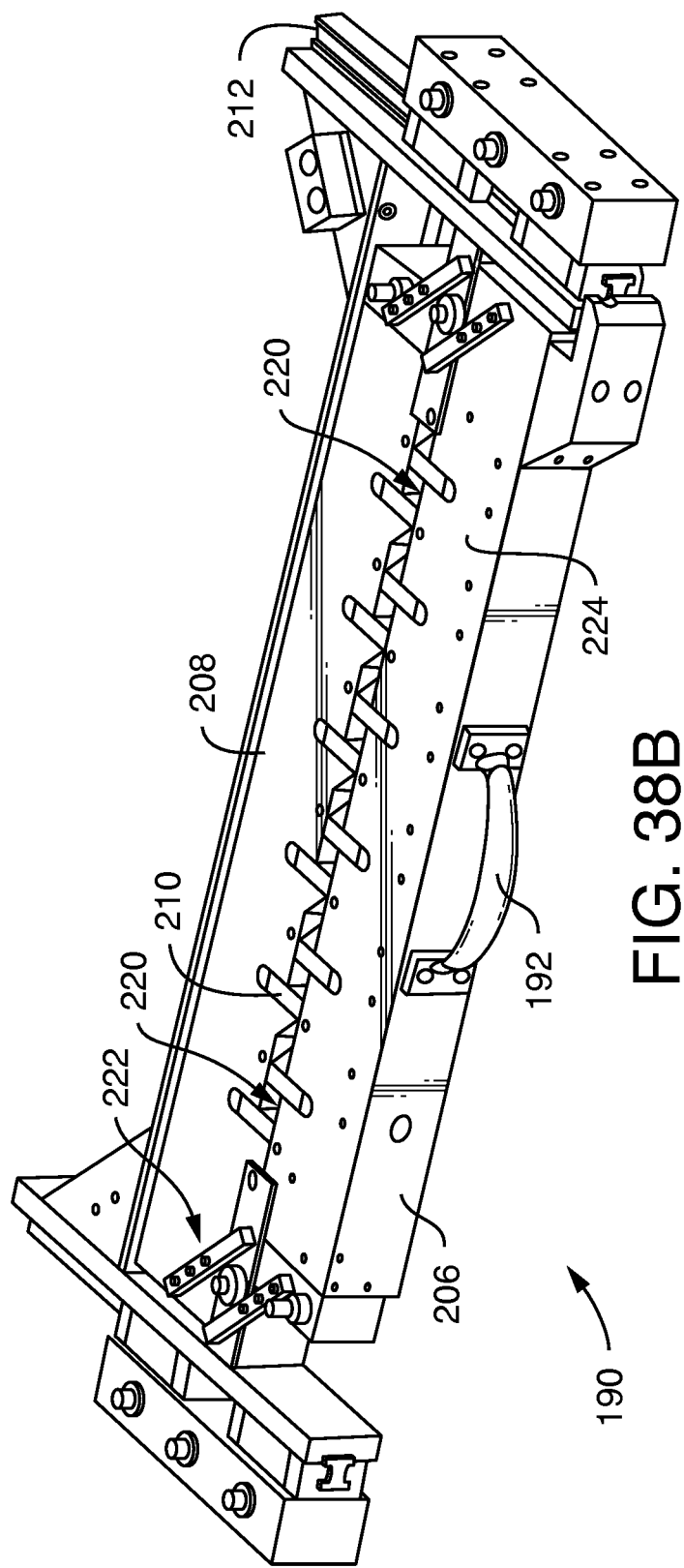

FIG. 36 provides a perspective view of an exemplary embodiment of the middle level 184 and the lower level 186 of a core insertion module 180. The core compression tray 190 and the barrel drum 194 are each in an open configuration and awaiting loading of cores 12 and a first pallet 120, respectively. FIG. 37 provides a perspective view of an exemplary embodiment of the middle level 184 and the lower level 186 of a core insertion module wherein the core compression tray 190 and the barrel drum 194 are each in a closed configuration. The core compression tray 190 has been pushed into the core insertion module 180 and the barrel drum 194 has been rotated 180°. The rotation of the barrel drum 194 180° can invert the first pallet 120 located within the barrel drum 194. FIG. 38A provides a perspective view of an exemplary embodiment of a core compression tray 190 in the open and uncompressed configuration and FIG. 38B provides a perspective view of an exemplary embodiment of a core compression tray 190 in a closed and compressed configuration. The core compression tray 190 can have a core compression tray handle 192, front and rear jaws, 206 and 208, respectively, guide blocks 210, an opening 220 for receiving the core(s) 12 to be loaded into the core compression tray 190, at least one jaw connection mechanism, such as a rack and pinion arrangement 222, and a guide rail 212. A jaw connection mechanism can connect jaws, 206 and 208, such that the jaws, 206 and 208, can move in tandom. Additional examples of jaw connection mechanism include, but are not limited to, slides, guide rails, and linear bearings. The core compression tray 190, when transitioning from an open configuration to a closed and compressed configuration, can maintain the shape of the openings 220 (i.e., the aspect ratio between the axes can be maintained) and the jaws, 206 and 208, can compress to the same degree.

A core 12 can be placed into an opening 220 between guide blocks 210 when loading cores 12 into the core compression tray 190. The guide rail 212 can help to guide the core compression tray 190 as the core compression tray 190 is pulled out from the core insertion module 180 and pushed into the core insertion module 190. In various embodiments, the core compression tray 190 can compress the core(s) 12 loaded within the core compression tray 190 after moving the core compression tray 190 into the core insertion module 180. In various embodiments, the core compression tray 190 can compress the core(s) 12 loaded within the core compression tray 190 as the core compression tray 190 is being pushed into the core insertion module 180. To compress the core(s) 12 loaded within the core compression tray 190, the front and rear jaws, 206 and 208, can shift 45° relative to the core insertion module 180 to compress the cores 12. The movement of the jaws, 206 and 208, towards each other to compress the core(s) 12 can be caused by air cylinder, pneumatic power, hydraulic power, or manual manipulation of the core compression tray 190. Pulling the core compression tray 190 out of the core insertion module 180 and into an open configuration can cause the jaws, 206 and 208, to release their compression. In various embodiments, the core compression tray 190 can have at least one opening 220 for receiving a core 12. In various embodiments, the core compression tray 190 can have from 1, 2, 3, 4, or 5 openings 220 to 6, 7, 8, 9, or 10 openings 220. In various embodiments, the core compression tray 190 can have the same number of openings 220 as locations 118 on the first pallet 120.

Figure 39:
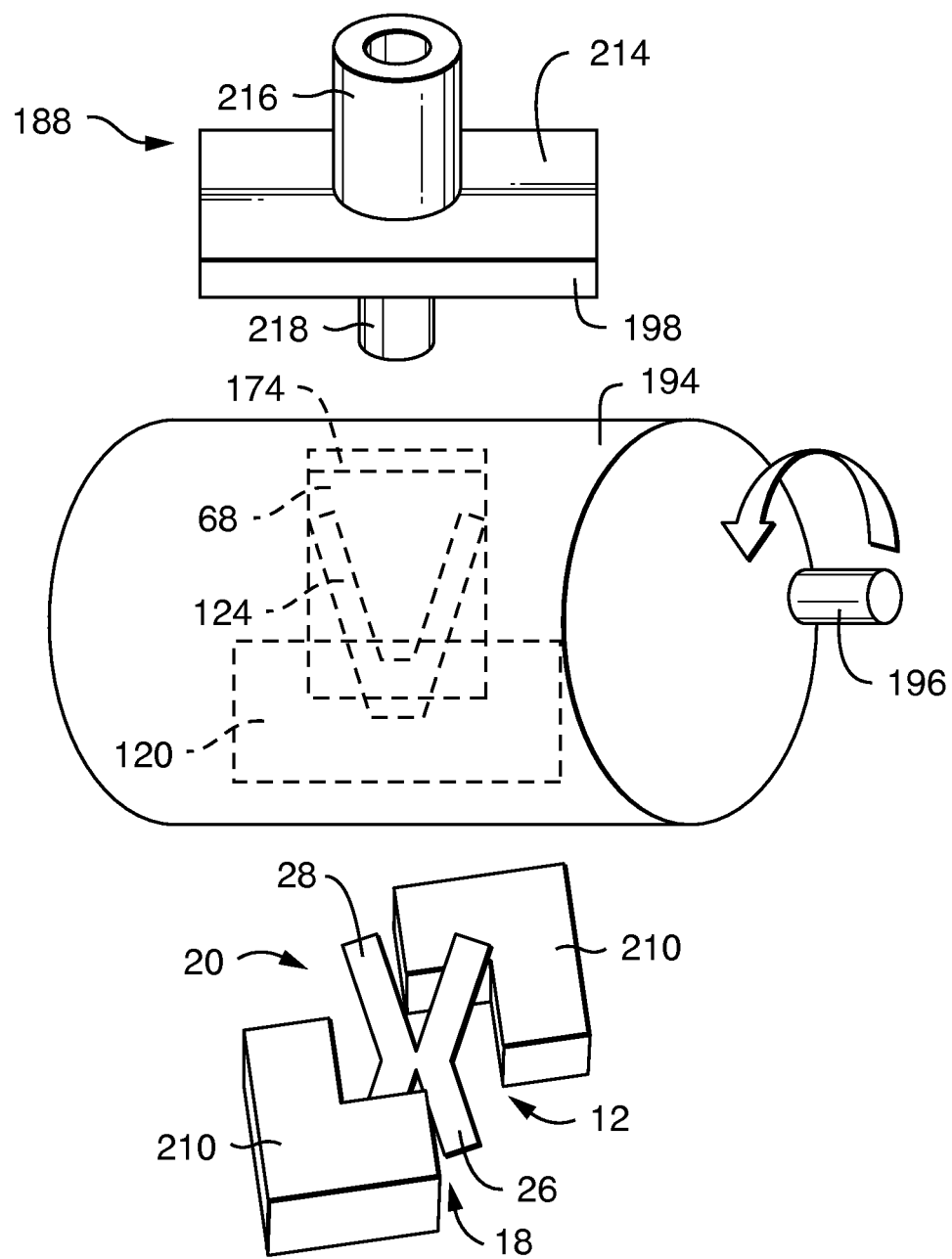
FIGS. 39-42 are schematic illustrations of exemplary process steps of inserting a core into a cover blank.

Referring to FIGS. 39-42, schematic illustrations for the process of operating a core insertion module 180 can be illustrated. As these are schematic illustrations and for clarity of illustration, many of the surrounding details of the core insertion module 180 have been removed from the illustrations. As can be seen in FIG. 39, an empty second pallet 188 can be loaded into the top level 182 of the core insertion module 180. The second pallet 188 can have a base 214 and at least one holder 216 for holding the core 12 and cover blank 68 combination. While the second pallet 188 is illustrated as having one holder 216, the second pallet 188 can have from 1, 2, 3, 4, or 5 holders 216 to 6, 7, 8, 9, or 10 holders 216. In various embodiments, the second pallet 188 can have the same number of holders 216 as the number of locations 118 on the first pallet 120. The empty second pallet 188 can be loaded onto a second pallet table 198 which can be capable of moving down from the top level 182 of the core insertion module 180 to the first pallet 120 located in the middle level 184 of the core insertion module 180. The second pallet table 198 can have a transfer tube 218 which can guide the core 12 and cover blank 68 combination during transition of the core 12 and cover blank 68 combination into the second pallet 188. The transfer tube 218 can also guide a pre-tuck rod 202 and a push rod 200 during their respective movement within the core insertion module 180. A first pallet 120 having at least one cover blank 68 loaded thereupon can be loaded into the middle level 184 of the core insertion module 180. The loading of the first pallet 120 into the middle level 184 of the core insertion module 180 can include placing the first pallet 120 inside the barrel drum 194 such that the supporting element seam 174 can be oriented upwards in the direction of the second pallet 188. As the first pallet 120 exited the pleater module, the prongs, 124 and 126, of the first pallet 120 were in a closed configuration. As the first pallet 120 can be moved and loaded into the middle level 184 of the core insertion module 180, the prongs, 124 and 126, can be transitioned from the closed configuration to an open configuration. It is to be noted that only prongs 124 are visible in FIG. 39, however, both pairs of prongs, 124 and 126, can transition into an open configuration. The opening of the prongs, 124 and 126, also results in moving the layers, 70 and 80, in a direction away from each other, and, therefore, an opening of the cover blank 68. This opening of the cover blank 68 can create a flat surface of the cover blank 68 over the supporting element 20 of the core 12.

Cores 12 can be loaded into the core compression tray 190 with the supporting arms 28 of the cores 12 oriented upwards in the direction of the second pallet 188. The core set tool 204 can be used to further push the core 12 into the opening 220 of the core compression tray 190 so that the core 12 is below the top surface 224 of the core compression tray 190. The core compression tray 190 can be pushed into the core insertion module 180. In various embodiments, pushing the core compression tray 190 into the core insertion module 180 can cause the core compression tray 190 to transition from an open and uncompressed configuration to a closed and compressed configuration. In various embodiments, the core compression tray 190 can transition from an open and uncompressed configuration to a closed and compressed configuration after the core compression tray 190 has been pushed into the core insertion module 180. In either case, the compression of the core compression tray 190 can be actuated via air cylinder, pneumatic power, hydraulic power, or manual manipulation of the core compression tray 190. It should be noted that the core compression tray 190, when in a closed and compressed configuration, compresses the entire core 12, top to bottom. To compress the core 12, the guide blocks 210 of the front and rear jaws, 206 and 208, can move towards each other at a 45° angle relative to the core insertion module 180. In various embodiments in which the core compression tray 190 has transitioned from an open and uncompressed configuration after being pushed into the core insertion module 180, the compression of the core(s) 12 can occur at any of the following times: prior to, during, or after the lowering of the second pallet 188 from the top level 182 to the middle level 184 of the core insertion module 180 or prior to, during, or after the lowering of the pre-tuck rods 202 from the top level 182 to the middle level 184 to pre-tuck the cover blank 68 into the core 12.

The barrel drum 194 can be inverted 180°, using the barrel drum handle 196 to invert the barrel drum 194. The inversion of the barrel drum 194 can cause the supporting element seam 174 of the cover blank 68 to change orientation such that the supporting element seam 174 can be oriented in the direction of the core 12 and can be closer in proximity to the core 12. The inverted orientation of the cover blank 68 can be seen in FIG. 40.

Figure 40:
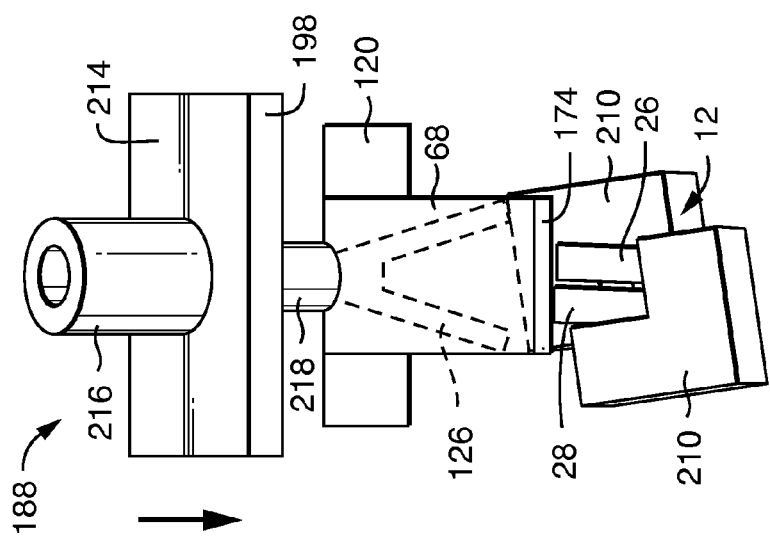

Referring to FIG. 40, the second pallet table 198 can be lowered from the top level 182 to the middle level 184 so that the second pallet 188 can be in closer proximity to the first pallet 120. While the transfer tube 218 can be illustrated (such as in FIG. 40) as having a length such that the transfer tube 218 is close in proximity to the base of the first pallet 120, in various embodiments, the transfer tube 218 can have a length such that when the second pallet table 198 is lowered from the top level 182 to the middle level 184, the transfer tube 218 can extend through the open area 132 in the first pallet 120 and can extend as far as the supporting element seam 174 of the cover blank 68. In various embodiments, the transfer tube 218 can extend into the cover blank 68 such that it can be closer in proximity to the supporting element seam 174 of the cover blank 68.

Figure 41:
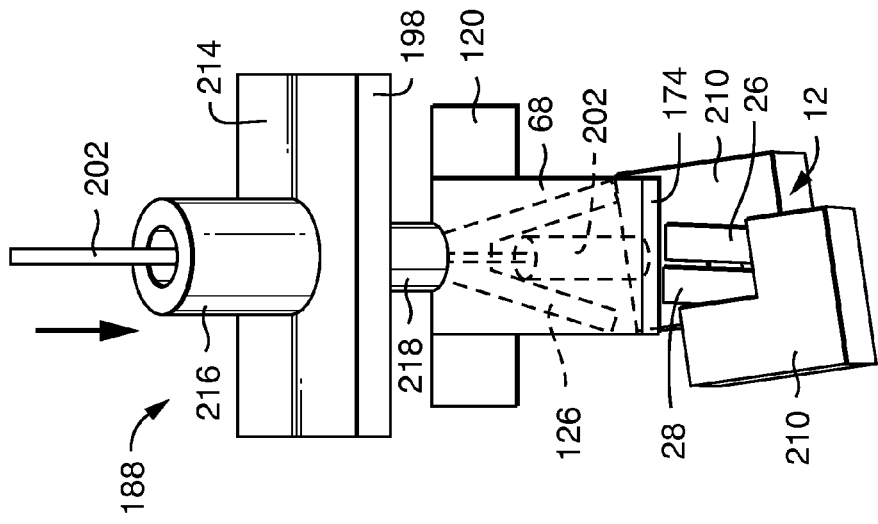

Referring to FIG. 41, once the second pallet 188 is lowered from the top level 182 to the middle level 184 to be closer in proximity to the first pallet 120, a pre-tuck rod 202 can lower from the top level 182 of the core insertion module 180 and can move through the open area in the second pallet holder 216, through an open area in the second pallet transfer tube 218, through the open area 132 in the first pallet 120, and between the prongs, 124 and 126, of the first pallet to push the supporting element seam 174 of the cover blank 68 against the supporting arms 28 of the core 12. In various embodiments, by pushing the supporting element seam 174 of the cover blank 68 against the supporting arms 28 of the core 12, the pre-tuck bar 202 can partially insert the cover blank 68 into the supporting element 20 of the core 12 such that when the process is completed the cover blank 68 can be loose on the core 12. Following, the partial insertion of the cover blank 68 into the supporting element 20 of the core 12, the pre-tuck bar 202 can be retracted.

Figure 42:
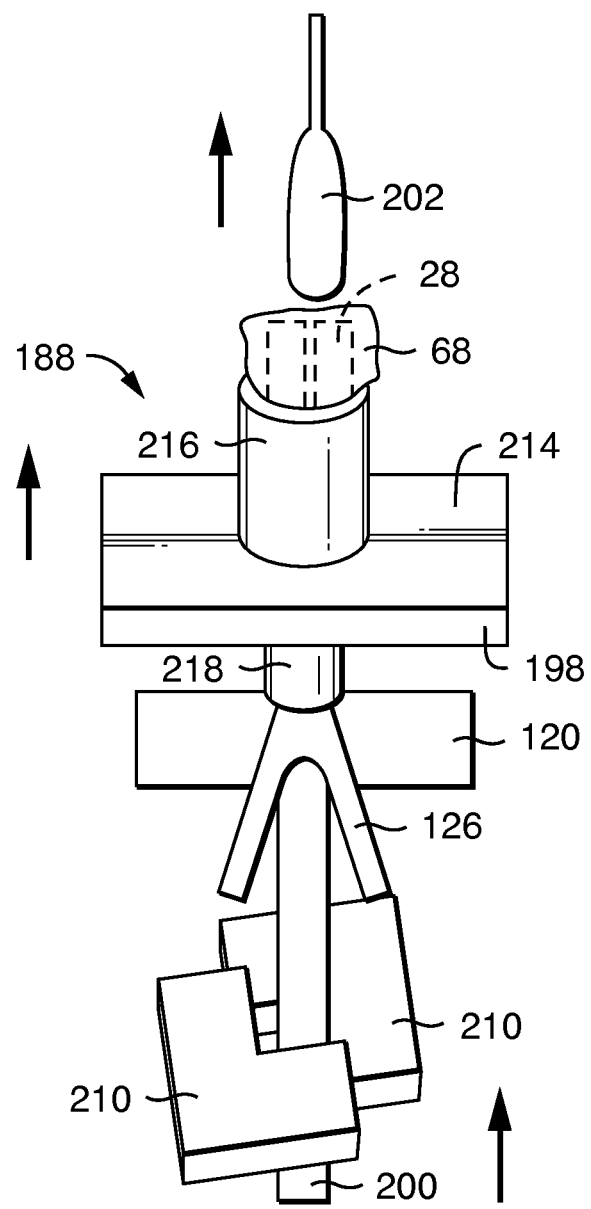

Referring to FIG. 42, after the pre-tuck bar 202 can be retracted, the push rod 200 can move upwards from the bottom level 186 of the core insertion module 180. The push rod 200 can move upwards through the opening 220 of the core compression tray 190, through the open area 132 of the first pallet 120, and through the guide tube 218 of the second pallet table 198. The push rod 200 can extend upwards to move the compressed core 12 towards the second pallet 188. This pushing of the compressed core 12 towards the second pallet 188 inserts the compressed core 12 into the cover blank 68 by moving the compressed core 12 through the opening in the cover blank 68 and inverting the cover blank 68 over the compressed core 12. The core 12 and cover blank 68 combination are also pushed upwards into the second pallet holder 216 of the second pallet 188 such as can be seen in FIG. 42. After the core 12 and cover blank 68 combination have reached the second pallet holder 216, the push rod 200 and second pallet table 198 can all be retracted to their respective starting positions. In other words, the push rod 200 can be lowered and the second pallet table 198 can be raised.

Following insertion of the core 12 into the cover blank 68 and following the loading of the core 12 and cover blank 68 combination in the second pallet 188, the supporting arms 28 of the core and the supporting element 20 region of the vaginal insert 10 can extend above the top surface of the second pallet holder 216. As described herein, a removal element 16 can be associated with the vaginal insert 10 at the supporting element 20 region of the vaginal insert 10. The second pallet 188 with the core 12 and cover blank 68 combination can be conveyed to a string and knot module. In various embodiments, the string and knot module can associate a removal element 16 with the supporting element 20 region of the vaginal insert 10 and can create two knots in the removal element 16. The double knotting of the removal element 16 can hold the removal element 16 in place on the vaginal insert 10 and can provide a wearer of the vaginal insert 10 a place to grasp the removal element 16 during withdrawal of the vaginal insert 10 from the vagina.

Figure 43:
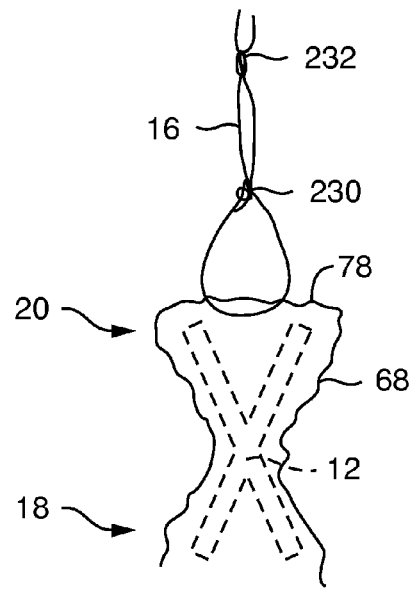
FIG. 43 is a front view of an exemplary embodiment of a partially manufactured vaginal insert with a removal element.

The core 12 and cover blank 68 combination in the second pallet 188 can enter a string and knot module with the supporting element seam 174 exposed above the second pallet holder 216. Following processing by the string and knot module, the top edges 72 of layers 70 and 80 of the cover blank 68 can still be unbonded and a removal element 16 can be attached to the cover blank 68 in the area of the supporting element seam 174 and knotted twice. FIG. 43 provides a schematic exemplary embodiment of the product following processing in the string and knot module.

The string and knot module can attach a removal element 16 to the cover blank 68 and can create lower and upper knots, 230 and 232, on the removal element 16. The string and knot module can use several mechanical assemblies and air/vacuum to control the removal element 16 as it is metered, cut and knotted. Assemblies associated with the stringing and knotting processes include: knotting block assemblies, a needle assembly, scissor assemblies, and cover blank 68 and removal element clamping assemblies.

Figure 44:
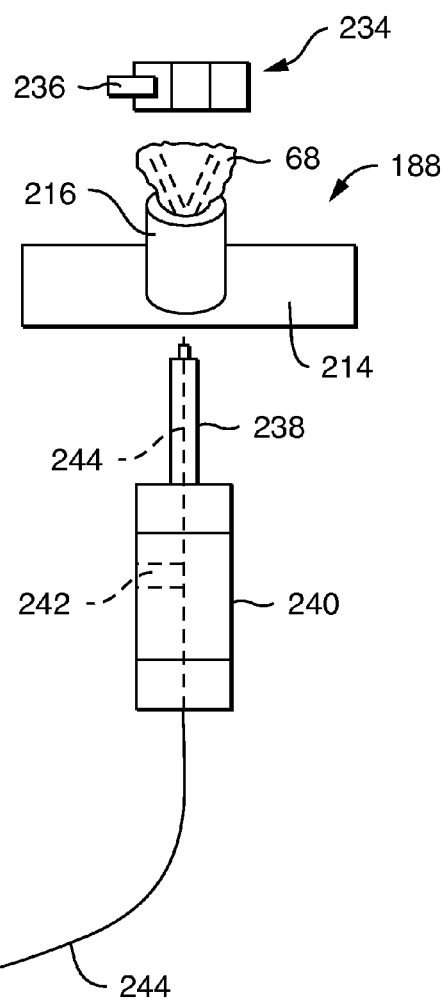
FIGS. 44-46 are schematic illustrations of exemplary process steps of attaching a removal element to a cover.
Figure 45:
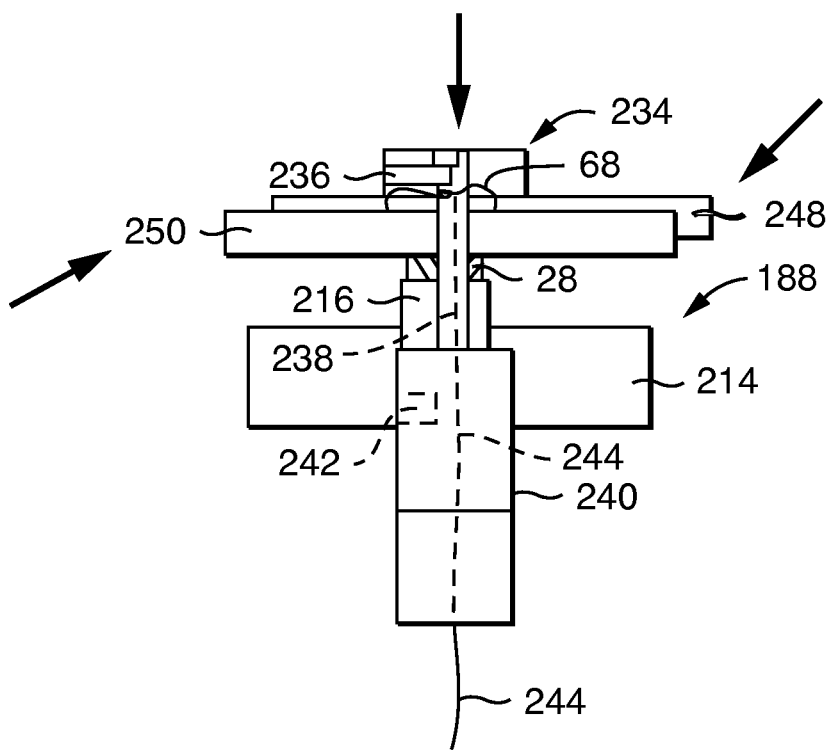
Figure 46:
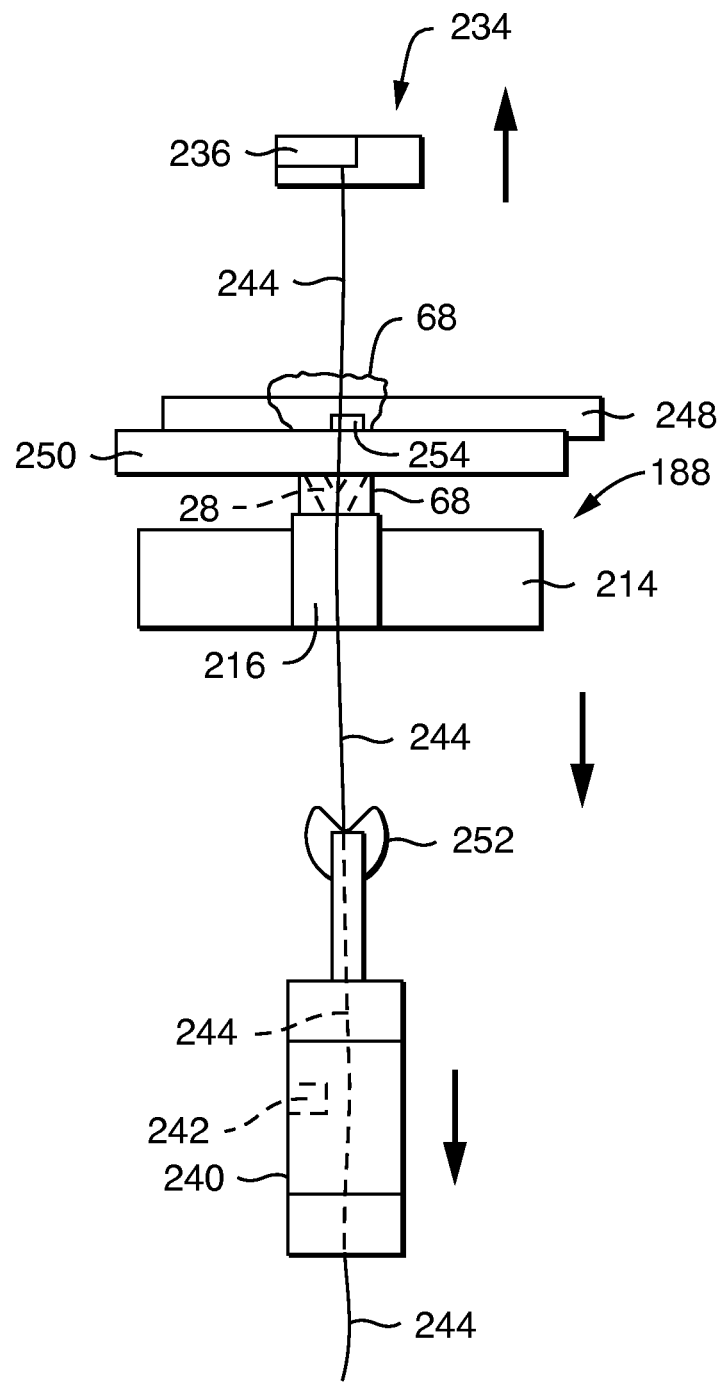

The overall process in the string and knot module has two main steps. The first step can be to insert a removal element 16 into the core 12 and cover blank 68 combination and the second step can be to create two knots in the removal element 16. FIGS. 44-46 provide schematic illustrations of embodiments of process steps for inserting a removal element 16, such as, for example, a string 244 into the core 12 and cover blank 68 combination and FIGS. 47-54 provide schematic illustrations of embodiments of process steps for double knotting a removal element 16.

Referring to FIG. 44, a schematic illustration of a stringing module can be illustrated. The stringing module can include a spool 246 of string 244. The spool 246 of string 244 can be located on an unwind stand and the string 244 can be allowed to flow freely from the spool 246 during the overall stringing process. In various embodiments, a mechanical weight can be attached to the string 244 to maintain tension in the string 244. The string 244 can move through a string block 240 that can move toward a needle 238 and back. In various embodiments, the movement of the string 244 through the string block 240 can be effected by an air pressure differential. In various embodiments, the air pressure differential can be such that the area of higher pressure is located in the area of the core 12 and cover blank 68 combination. In various embodiments, the movement of the string 244 through the string block 240 can be effected by pushing on the string 244 with air. In various embodiments, the movement of the string 244 through the string block 240 can occur via pulling on the string 244 with a vacuum. As the string block 240 can move towards the needle 238, the movement of the string block 240 can move the string 244 by the same amount as the movement of the string block 240. An internal string clamp 242, located within the string block 240, can be utilized to stop the string 244 from moving when it is desired that the string 244 not move. A hollow needle 238 can allow the string 244 to move through the needle 238. In various embodiments, any type of component providing a channel for the string 244 can be utilized in place of a hollow needle 238. Opposite to the needle 238, and on the other side of the core 12 and cover blank 68 combination, a string pulling clamp mechanism 234 can be located. The string pulling clamp mechanism 234 can move forwards/backwards with the needle 238 mechanisms. A string clamp 236 within the string pulling/clamp mechanism 234 can be used to hold the string 244 after the needle 238 has pierced the cover blank 68 and pushed the string 244 through the cover blank 68.

Referring to FIG. 45, a schematic view of the basic process of providing a string 244 can be illustrated. It is to be noted that, while not illustrated in FIG. 45, two funnels 256 associated with the lower knotting block 262 can be lowered into position and on either side of the cover blank 68 prior to the stringing of the cover blank 68. More details on the funnels 256 and the knotting process will be provided below. A second pallet 188 holding a core 12 and cover blank 68 combination can be indexed into position for the provision of the removal element 16, such as in the form of string 244. As the second pallet 188 can be indexed into position, the core 12 and cover blank 68 combination can be rotated. The rotation can provide that the needle 238 and the string 244 may not pierce the supporting element seam 174 as piercing of the supporting element seam 174 can weaken the overall supporting element seam 174.

Air can be pushed up towards the second pallet base 214 from underneath the second pallet 188. The air can further move through the second pallet holder 216 which can "puff up" and tent the cover blank 68 above the supporting arms 28 of the core 12. Following the "puffing up" and tenting of the cover blank 68, cover blank 68 clamps, 248 and 250, can close on the cover blank 68 and the core 12. The closure of the cover blank clamps, 248 and 250, can collapse the supporting arms 28 of the core 12 as well as the cover blank 68. As the cover blank 68 was "puffed up" and tented prior to the closure of the cover blank clamps, 248 and 250, a portion of the cover blank 68 can extend above the height of the cover blank clamps, 248 and 250. The air movement underneath the second pallet 188 and the closure of the cover blank clamps, 248 and 250, can, therefore, cause the cover blank 68 to tent up and provide a location wherein the needle 238 can thread the string 244 through.

The two funnels 256 associated with the lower knotting block can lower with one funnel 256 on each side of the tented cover blank 68. To move the string 244 through the cover blank 68, the needle 238 can be moved forward towards the cover blank 68. The needle 238 can move through an opening in the first funnel 256, four layers of the pleated and tented cover blank 68, and through an opening in the second funnel 256 located on the opposite side of the cover blank 68. The string block mechanism 240 can move towards the back of the needle 238 and can feed about ½ inch of string 244 through the needle 238. The string 244, which has been fed by the needle 238 through the first funnel 256, the four layers of the pleated and tented cover blank 68, and the second funnel 256, can be captured by the string clamp 236 in the string pulling clamp mechanism 234 which can also move forwards towards the cover blank 68. The string pulling clamp 236 can clamp the end of the string 244 and the string block mechanism 240 can be released.

Referring to FIG. 46, the needle 238 and the string pulling clamp mechanism 234 can each move back to their starting positions. As the string 244 can be clamped and held by the string clamp 236 in the string pulling clamp mechanism 234, the string 244 can be pulled by the string pulling clamp mechanism 234 and the distance of the move backwards by the string pulling clamp mechanism 234 can set the length of the string 244. The string 244 can be pinched in the middle, at the location of the tented cover blank 68, by a string pincher 254 to prevent it from sliding during the knotting process. The pinch in the string 244 can be held until the first knot is created. Once the desired length of string 244 is obtained and the string 244 has been pinched by a string pincher 254, the string can be cut by a string cutter 252 located in proximity to the needle 238 and the string push clamp 242 can be clamped to prepare the string 244 for the next cycle.

Figure 47:
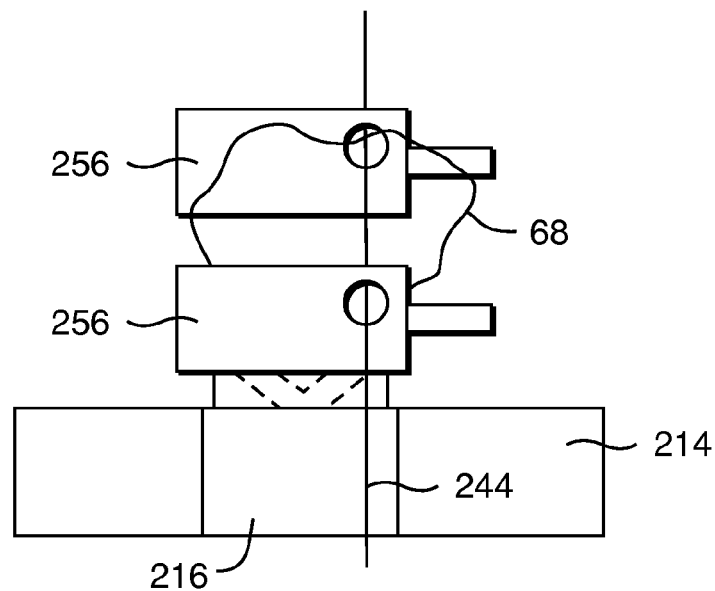
FIGS. 47-50 are schematic illustrations of exemplary process steps of knotting a removal element.

The knotting of the string 244 can start at the same time as the string 244 feed through the first funnel 256, through the four layers of pleated and tented cover blank 68, and through the second funnel 256 to the string pulling clamp mechanism 234. The knotting can include the steps of lowering the upper and lower knotting blocks, 260 and 262, respectively, and funnels 256 into position when the core 12 and cover blank 68 is first clamped. The funnels 256 can be in position before the needle 238 is moved through the core 12 and cover blank 68. Such as illustrated in FIG. 47, the string 244 can be fed through two funnels 256 which are located on each side of the pleated and tented cover blank 68. It is to be noted that the funnels 256 can be used to position the string 244 into the knotting blocks. The funnels 256 can be opened when they are in the stringing position by following a mechanical cam. When the knotting blocks, 260 and 262, move upwards from the stringer module, the funnels 256 exit the mechanical cam and close. In various embodiments, the funnels 256 can be held closed by the use of small magnets. Each of the knotting blocks, 260 and 262, can move independently of the other knotting block, 260 and 262. Each of the knotting blocks, 260 and 262, can have upper and lower portions which can also move independently. Upper knotting block 260 can have upper portion 228 and lower portion 226. Lower knotting block 262 can have upper portion 278 and lower portion 276.

Figure 48:
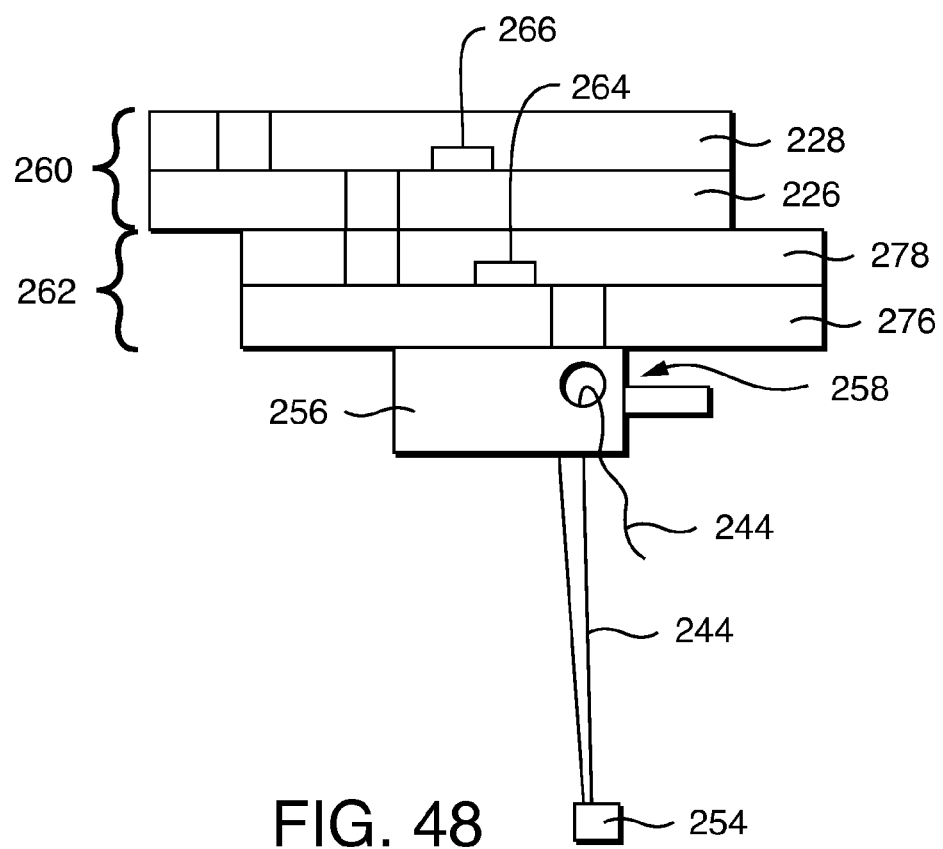

Once the string 244 is cut, such as illustrated in FIG. 47, the knotting blocks, 260 and 262, and the funnels 256 move up to straighten the string such as illustrated in FIG. 48. The string 244 remains pinched by the string pincher 254, however, the string 244 can be released from the string pulling clamp mechanism 234. The entry point 258 of the string into the lower knotting block 262 can be at the bottom of the lower knotting block 262. The string pincher 254 can continue to hold the string 244 while the funnels 256 and upper and lower knotting blocks, 260 and 262, are lifted.

Figure 49:
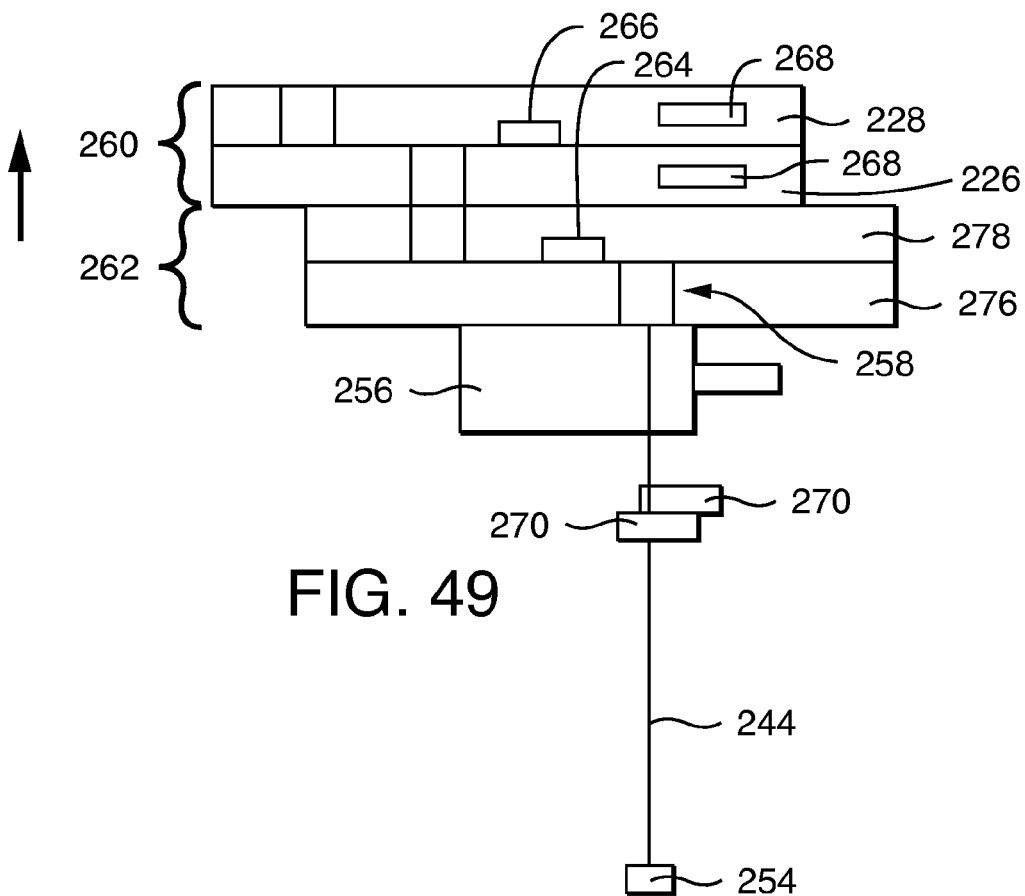

Referring to FIG. 49, once the string 244 has been lifted upwards by the upward movement of the funnels 256 and the upper and lower knotting blocks, 260 and 262, string holders 270 can be utilized to momentarily hold up the string 244 and prevent it from collapsing towards the products. The string holders 270 can support the weight of the string 244 until the string 244 can be brought into the knotting blocks, 260 and 262. From this point forward, the funnels 256 can remain closed for the remainder of the process.

Figure 50:
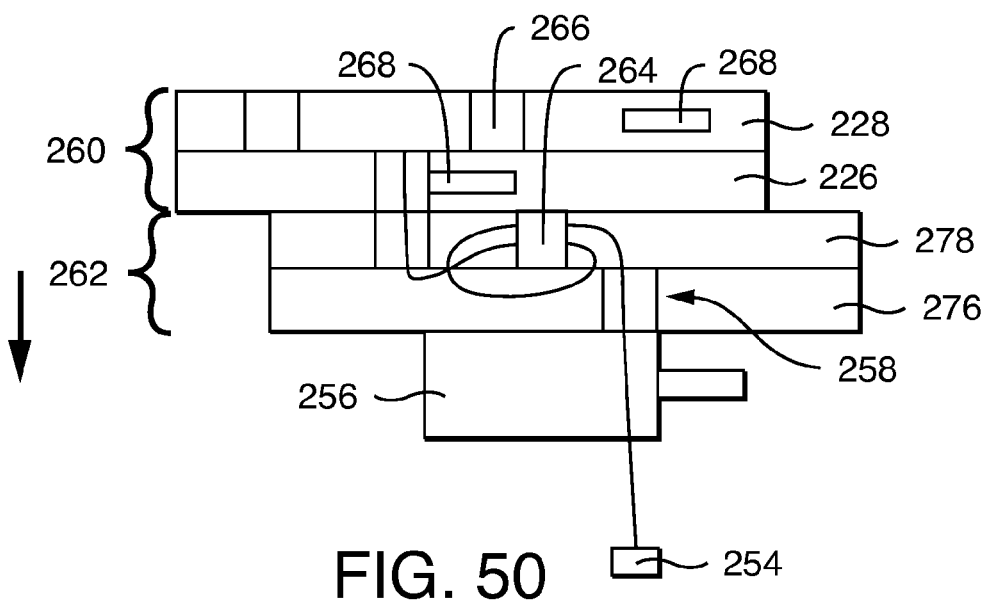
Figure 51:
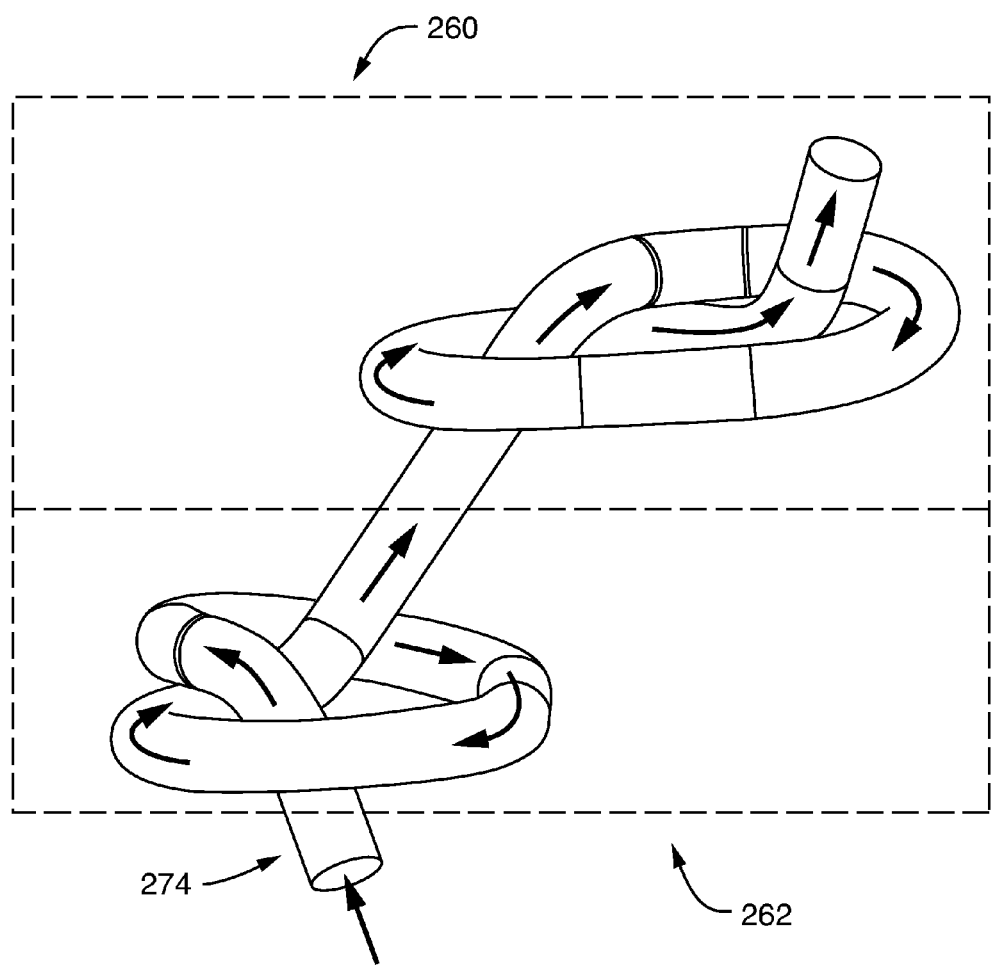
FIG. 51 is a schematic illustration of an exemplary string path.

Referring to FIG. 50, the knotting blocks, 260 and 262, can be lowered to the string holders 270 and a vacuum can be used to pull the string 244 through the knotting blocks, 260 and 262. The knotting blocks, 260 and 262, can have a string path 274 that can create a knot loop around center pins, such as center pins 264 and 266. The center pins, 264 and 266, can be used to force a knot to be created at a specific spot on the string 244. In various embodiments, the center pins, 264 and 266, can be located in the upper portions, 228 and 278, of the knotting blocks, 260 and 262, respectively. For example, center pin 264 can be located in upper portion 278 of the lower knotting block 262 and center pin 266 can be located in upper portion 228 of the upper knotting block 260. Once the string 244 can be fed through the string path 274 and around a center pin, 264 or 266, a clamp 268 can be used to hold the string 244 while the knot is created. The string path 274 can be illustrated in FIG. 51. For clarity, the knotting block details are not shown in the illustration of FIG. 51, however, the string path 274 illustrated can demonstrate the path that the string 244 can follow around center pin 264 in the lower knotting block 262 and center pin 266 in the upper knotting block 260. The string path 274 can be an "overhand knot" path in both the upper and lower knotting blocks, 260 and 262. In various embodiments, the upper knotting block 260 portion of the string path 274 can be at a 90° and to the lower knotting block 262 portion of the string path 274.

Referring to FIG. 50, the string 244 can follow the string path 274 which can take the string 244 around center pin 264 located in the upper portion 278 of lower knotting block 262. The string 244 can continue to follow the string path 274 to the lower portion 226 of the upper knotting block 260 where the string 244 can be clamped by the string clamp 268 located in the lower portion 226 of the upper knotting block 260.

Figure 52:
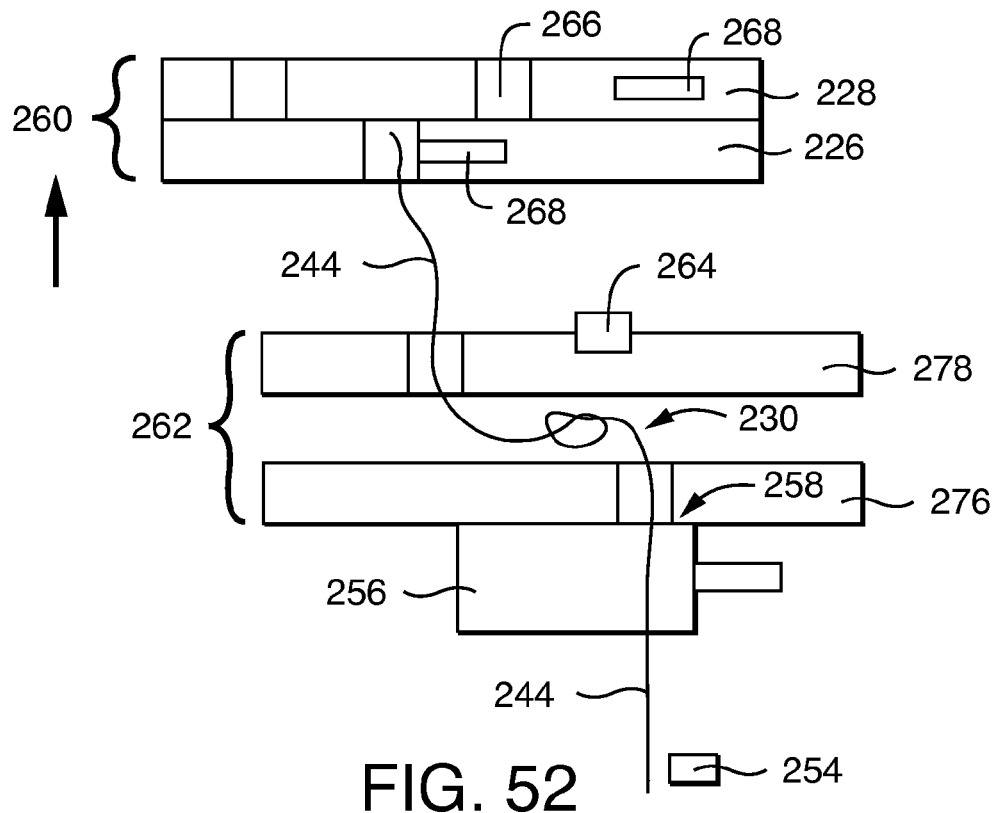
FIG. 52-55 are schematic illustrations of exemplary process steps of knotting a removal element.

As can be seen in the schematic illustration of FIG. 52, the upper knotting block 260 can move upwards which can cause the upper and lower portions, 278 and 276, of the lower knotting block 262 to open. The opening of the upper and lower portions, 278 and 276, of the lower knotting block 262 can allow the center pin 264 to retract. As the upper knotting block 260 can continue to move upwards, the string 244 can be tightened and the portion of the string 244 which had been wrapped around the center pin 264 can form the lower knot 230. The lower knot 230 can be tightened by the upward movement of the upper knotting block 260 and the string clamp 268 in the lower portion 226 of the upper knotting block 260. The lower knotting block 262 can remain open for the rest of the process. The string pincher 254 can also be released at this point.

Figure 53:
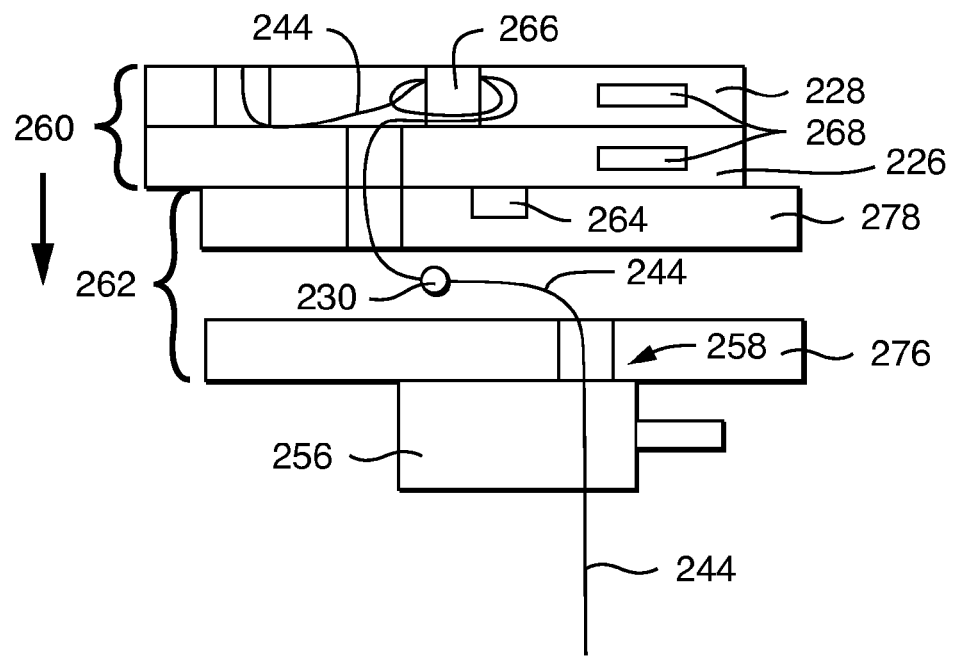
Figure 54:
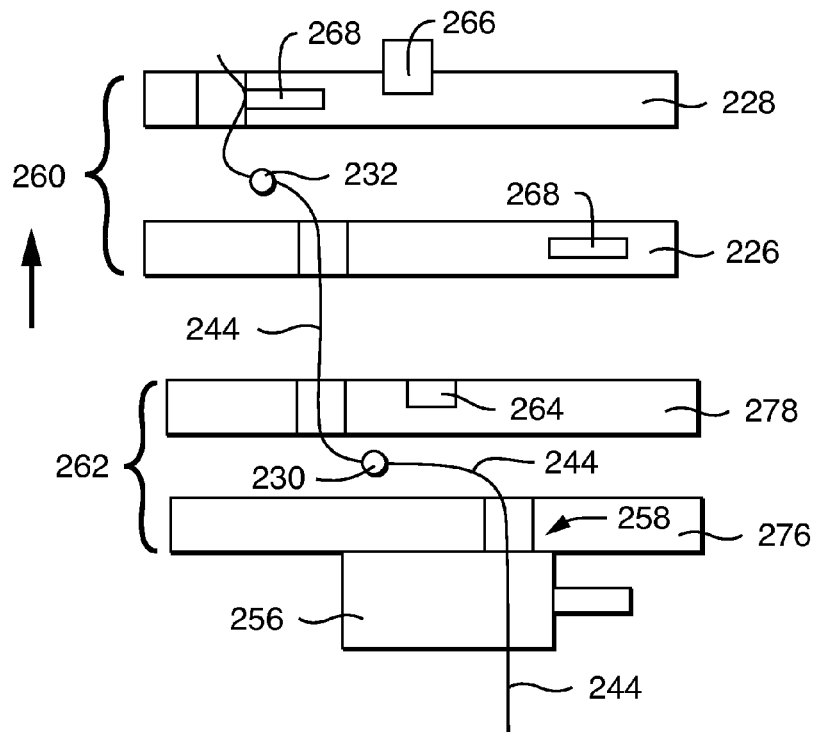

After the lower knot 230 is complete, the upper knotting block 260 can move downward to take the string 244 in again to form a second knot 232. As with the lower knot 230, the string 244 follows the string path 274 that can wrap the string 244 around the center pin 266 in the upper portion 228 of the upper knotting block 260. FIG. 53 provides a schematic representation of such a process step. Referring to FIG. 54, once the string 244 has wrapped around the center pin 266 in the upper portion 228 of the upper knotting block 260, a string clamp 268 in the upper portion 228 of the upper knotting block 260 can be used to hold the string 244 while the knot 232 is tightened. The upper portion 228 of the upper knotting block 260 can move upwards and open the upper portion 228 from the lower portion 226 of the upper knotting block 260 to allow the center pin 266 to retract. As the upper portion 228 of the upper knotting block 260 can continue to move upwards, the string 244 can be tightened and the portion of the string 244 which had been wrapped around the center pin 266 can form the upper knot 232. The upper knot 232 can be tightened by the upward movement of the upper portion 228 of the upper knotting block 260.

Figure 55:
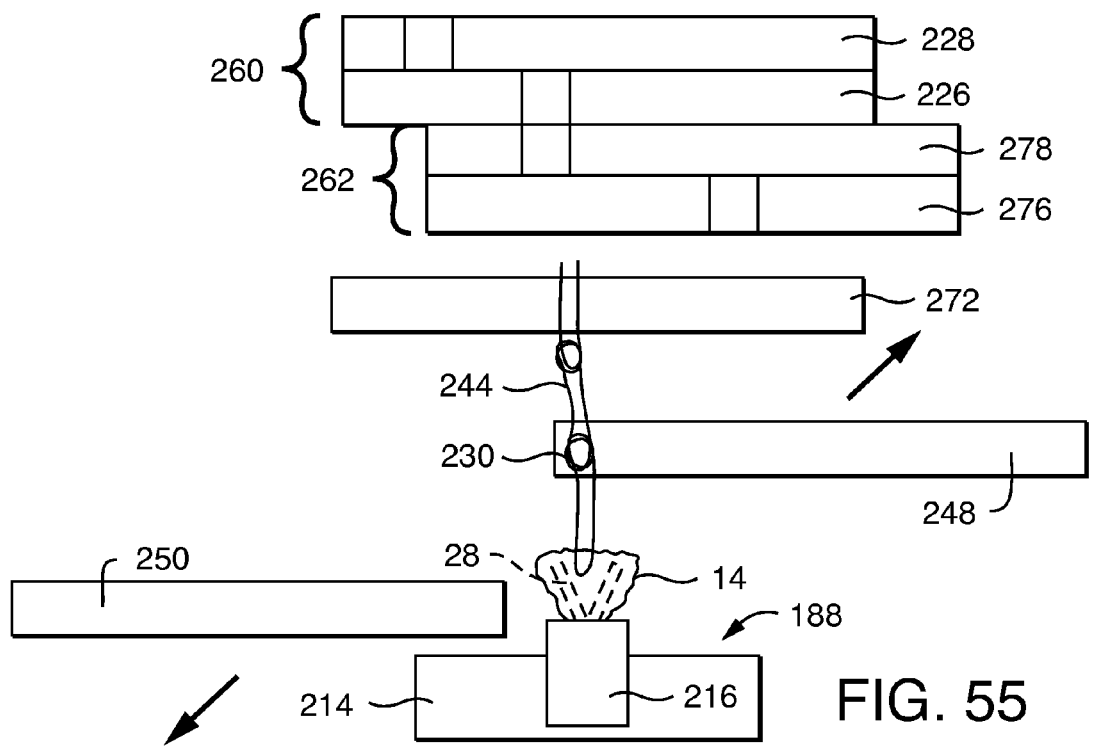

FIG. 55 is a schematic illustration that can demonstrate that once the knots, 230 and 232, can be formed, the knotting blocks, 260 and 262, can be moved upwards to their starting positions. A string control mechanism 272 can be moved forward to catch the strings and prevent them from being snapped towards the core 12 and cover blank 68 combination in the second pallet 188 while the second pallet 188 indexes towards the next portion of the manufacturing process and the cover clamps, 248 and 250, can be retracted. It is to be noted that while the knotting module can be described as having an upper knotting block 260 and a lower knotting block 262, in various embodiments, the knotting module can have only one knotting block. In such embodiments, the knotting module can produce a first knot in the string, reposition the string within the same knotting block, and create a second knot into the string.

Figure 56:
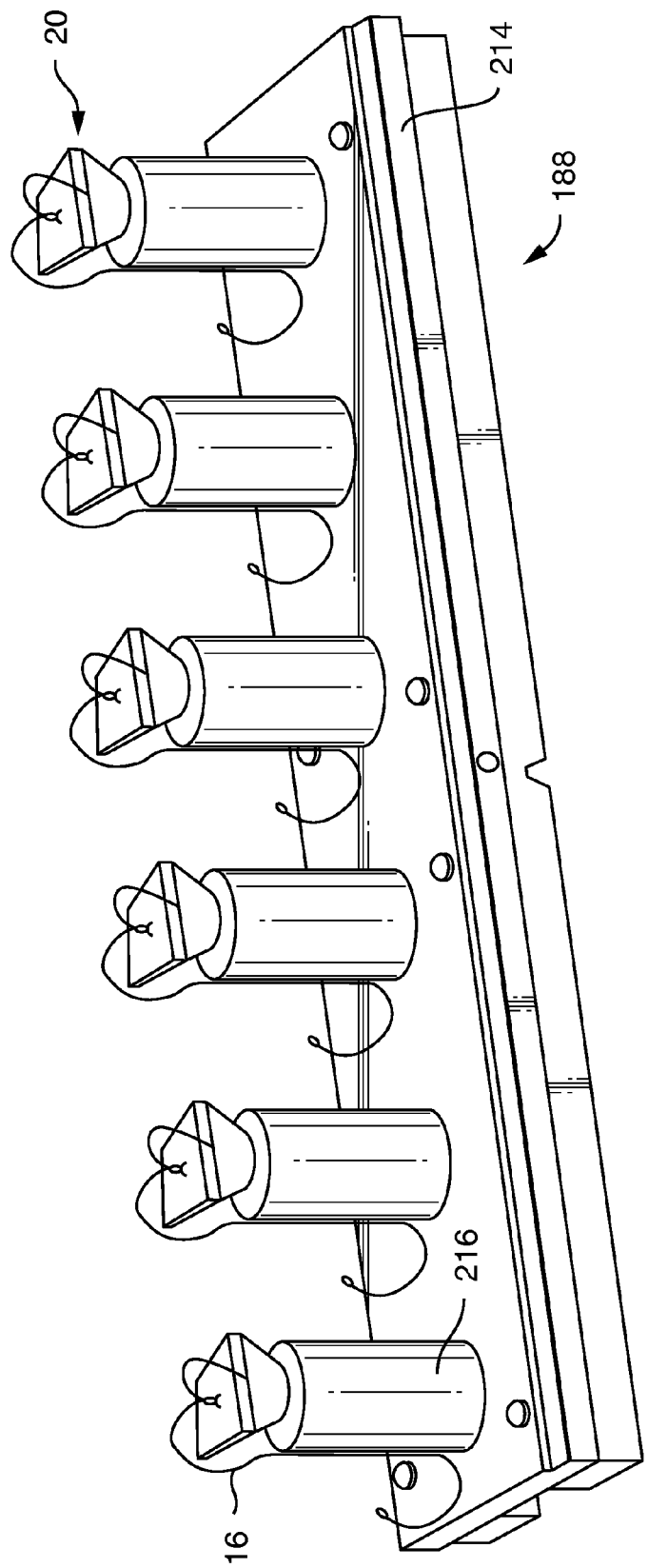
FIG. 56 is a perspective view of an exemplary embodiment of a core and cover blank in a second pallet.
Figure 57:
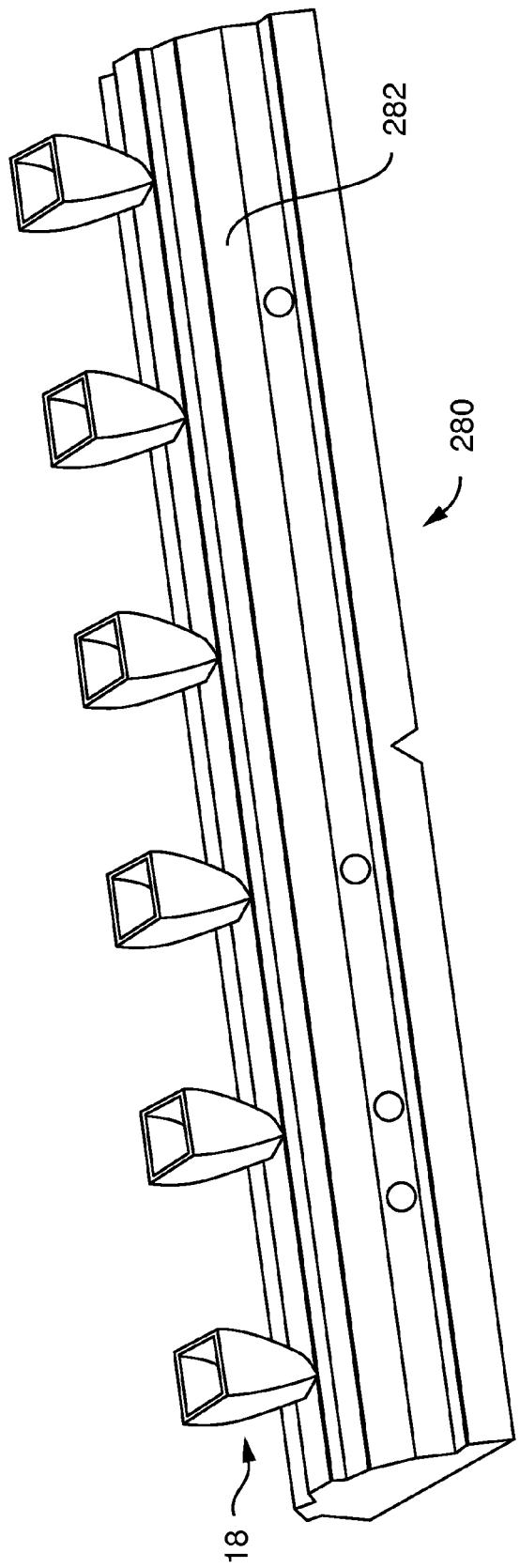
FIG. 57 is a perspective view of an exemplary embodiment of a core and cover blank in a third pallet.

Following the attachment of the string 244 which can form the removal element 16, it can be beneficial to transfer the core 12 and cover blank 68 combination to a third pallet 280. The transfer of the core 12 and cover blank 68 combination to the third pallet 280 can allow for the inversion of the core 12 and cover blank 68 combination and allow for the ability to bond the top edges 76 of the layers 70 and 80 of the cover blank 68 thereby fully enclosing the core 12 and converting the cover blank 68 to a cover 14. FIG. 56 provides a perspective view of an exemplary embodiment of the core 12 and cover blank 68 combination in which the core 12 is positioned within the cover blank 68 with a removal element 16 attached at the supporting element 20 region, however, one end of the cover blank 68 remains unbonded. FIG. 57 provides a perspective view of an exemplary embodiment of a third pallet 280 in which the core 12 and cover blank 68 combination can be reversed from the configuration illustrated in FIG. 56. In other words, the core 12 and cover blank 68 combination in the second pallet 188 provides for the removal element 16 to be attached to the cover blank 68 and visible external to the second pallet 188. The core 12 and cover blank 68 combination of FIG. 57 illustrates that, following transfer from the second pallet 188 to the third pallet 280, the removal element 16 and the supporting element 20 of the core 12 and cover blank 68 combination are within the interior of the third pallet 280 and the anchoring element 18 extends beyond the outside surface of the third pallet 280.

Figure 63:
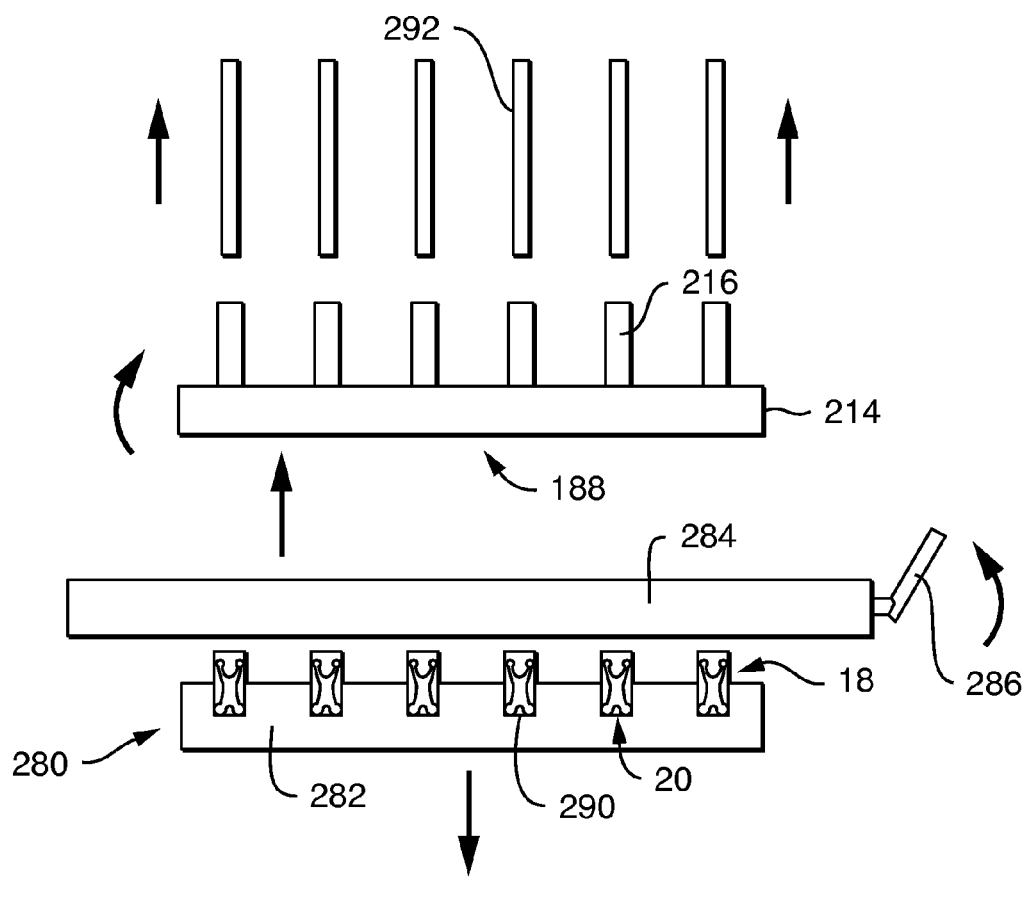
Figure 64:
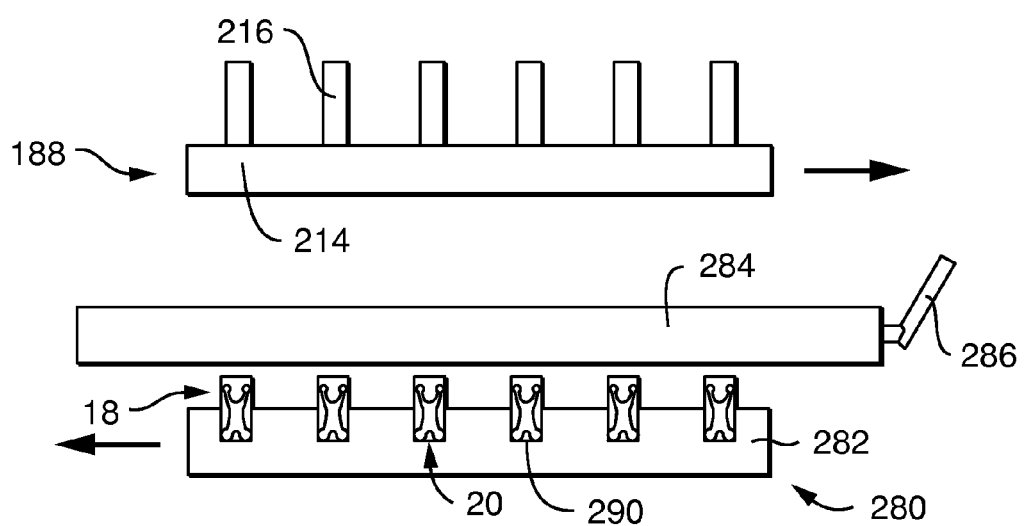
Figure 65:
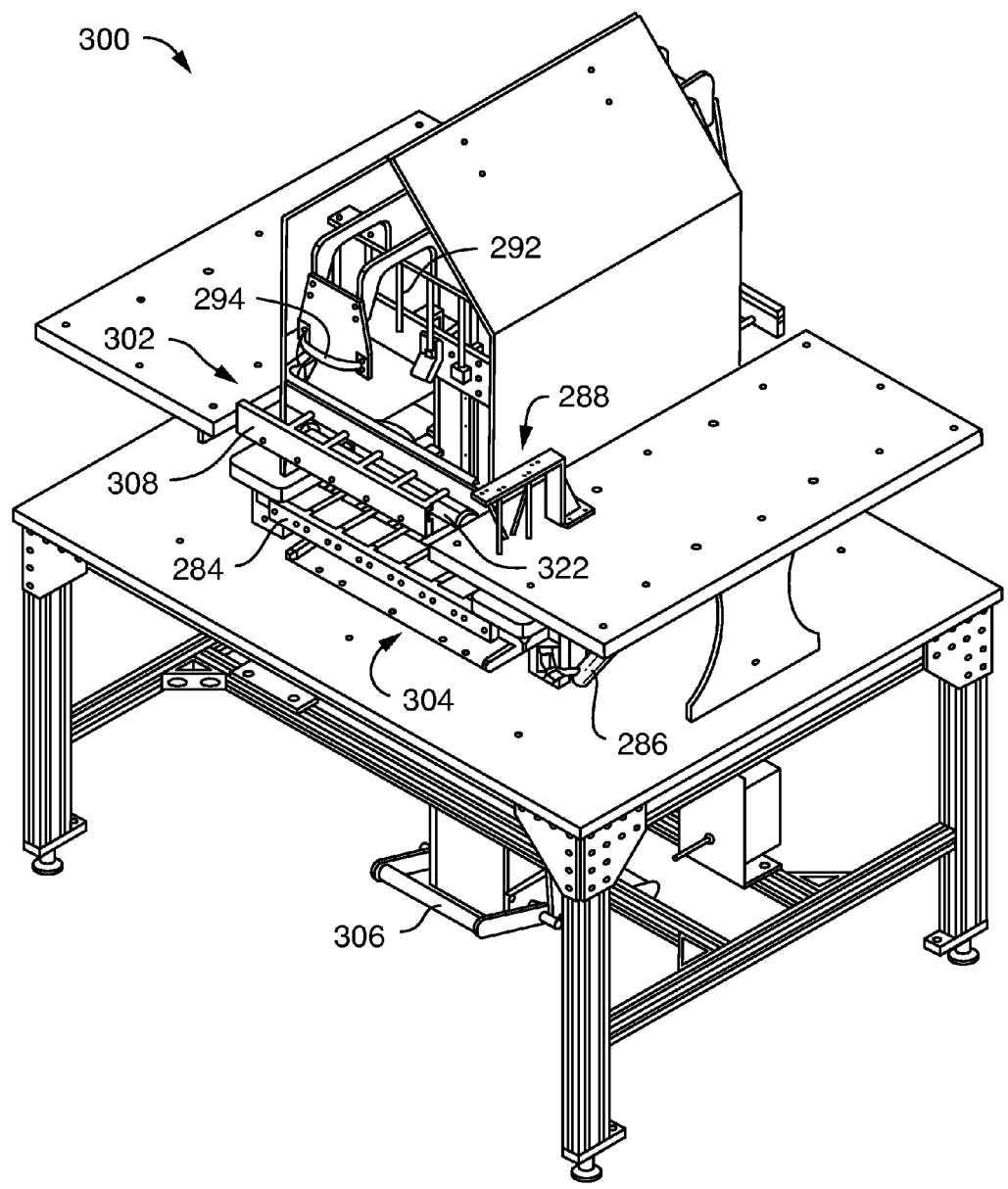
FIG. 65 is a perspective view of an exemplary embodiment of a pallet transfer module.
Figure 66:
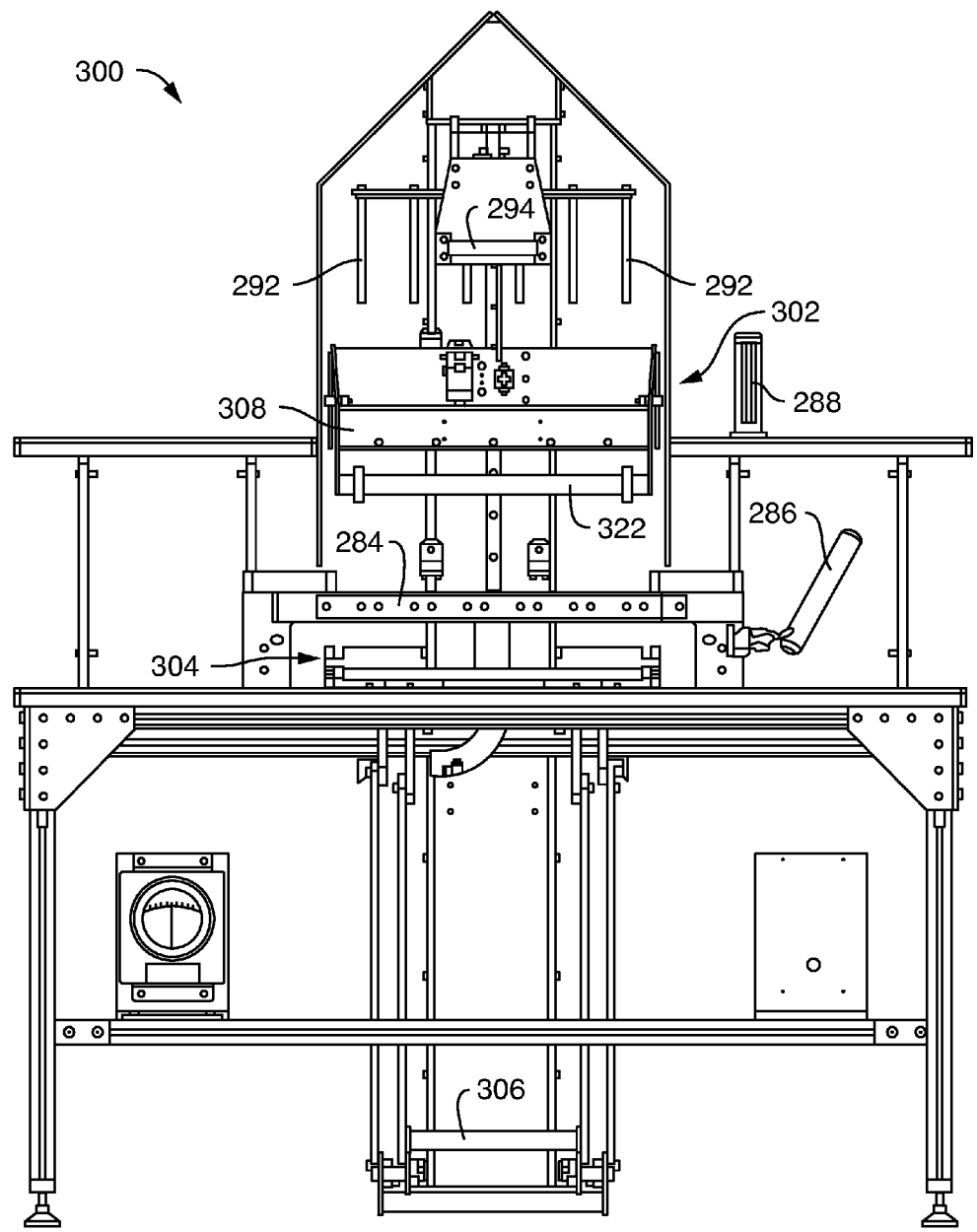
FIG. 66 is a front view of an exemplary embodiment of a pallet transfer module.
Figure 67:
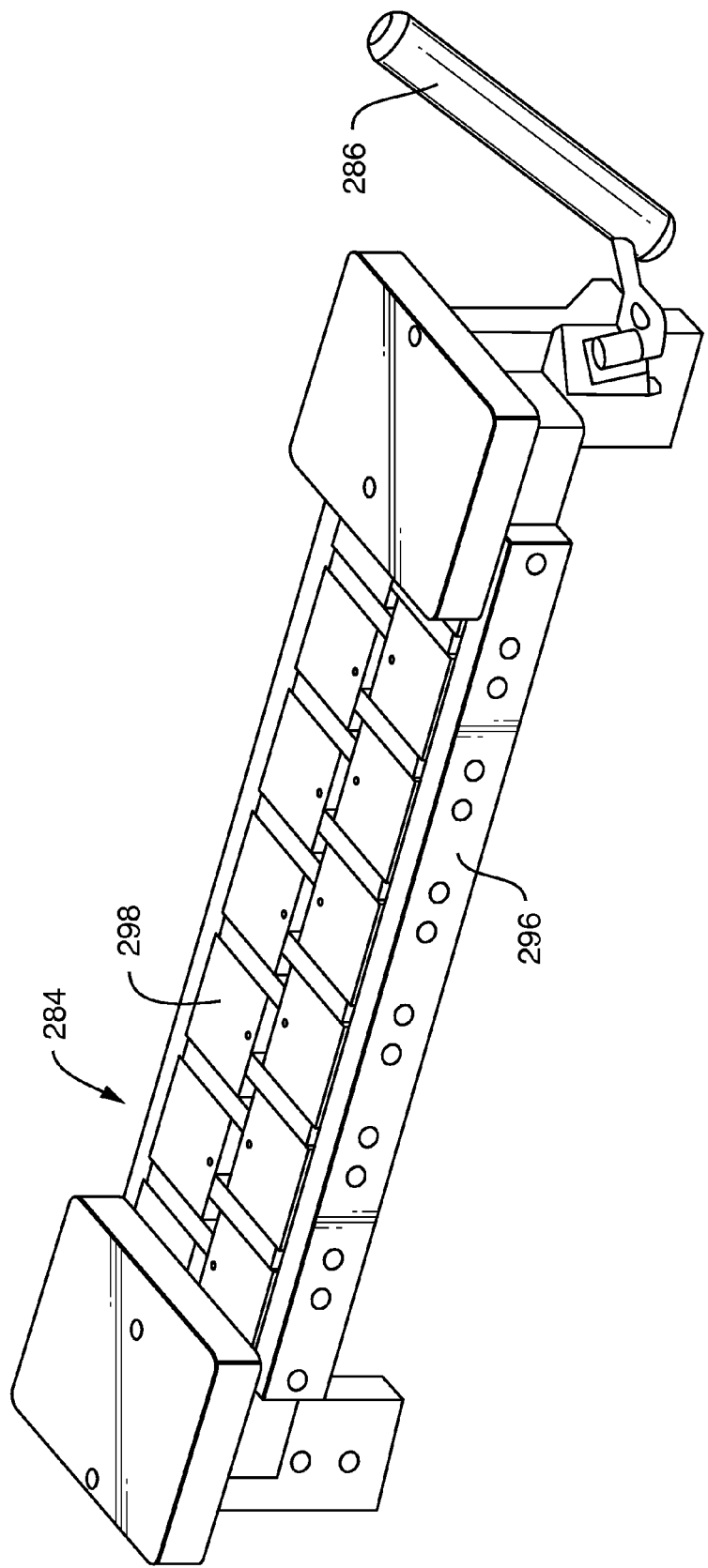
FIG. 67 is a perspective view of an exemplary embodiment of a compressor.

Schematic illustrations for the process of the transfer of the core 12 and cover blank 68 combinations from the second pallet 188 to a third pallet 280 can be illustrated in FIGS. 58-64 with further reference to FIGS. 65-67 regarding the transfer module 300. The transfer module 300 can have a second pallet 188 loading zone 302, removal element wipers 288, a third pallet 280 loading zone 304, an inverter 308 and an inverter handle 322, a compressor 284 and compressor handle 286, push rods 292 and a push rod handle 294, and foot peddle 306. The inverter 308 can rotate 180° and can also raise and lower the second pallet 188 in its inverted orientation (i.e., following rotation of the inverter 308). A second pallet 188 can be conveyed to the second pallet loading zone 302 of the transfer module 300 following attachment of the removal element 16 to the cover blank 68. When conveying the second pallet 188 into the second pallet loading zone 302, the second pallet 188 can be passed through a set of removal element wipers 288 to ensure that the removal elements 16 will not get caught in any components of the transfer module 300 such as guide rails. The second pallet 188 can be loaded onto an inverter 308 which can invert the second pallet 188 into position for the transfer of the core 12 and cover blank 68 combination. The second pallet loading zone 304 and the inverter 308 can be positioned above the compressor 284. An empty third pallet 280 can be loaded into the third pallet loading zone 304. The third pallet loading zone 304 can include a lift tray which can lift the third pallet 280 upwards towards the compressor 284. The third pallet loading zone 304 can, therefore, be positioned below the compressor 284. The third pallet 280 can have locations 290 for receiving the core 12 and cover blank 68 combinations. The third pallet 280 can have as many locations as are deemed suitable. In an embodiment, the third pallet 280 can have at least one location 290. In an embodiment, the third pallet can have from 1, 2, 3, 4, or 5 locations 290 to 6, 7, 8, 9 or 10 locations 290. In various embodiments, the third pallet 280 can have the same number of locations 290 as the number of locations 118 on the first pallet 120.

Figure 58:
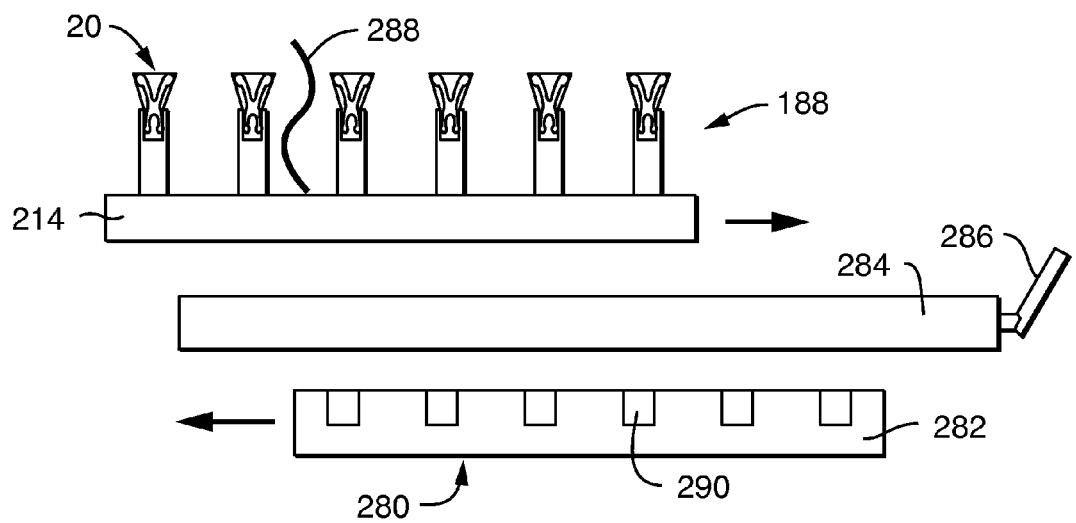
FIGS. 58-64 are schematic illustrations of exemplary process steps in the transfer of the core and cover blank combination from a second pallet to a third pallet.
Figure 59:
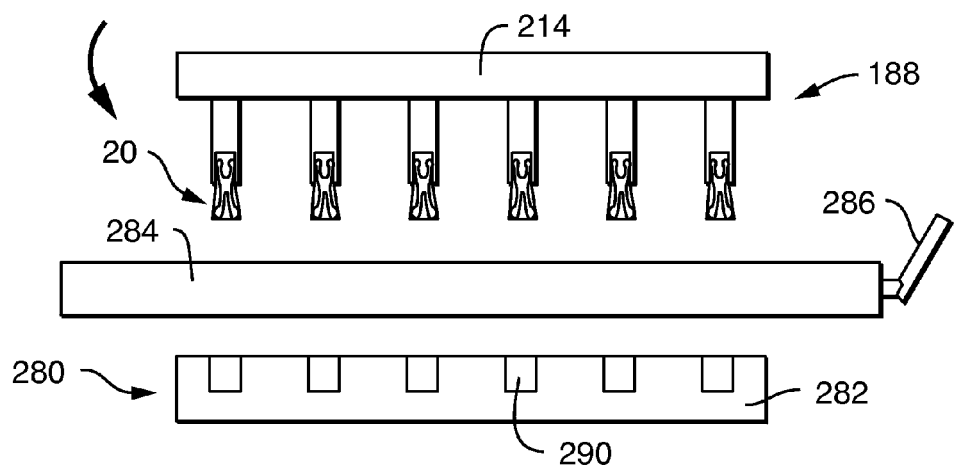
Figure 60:
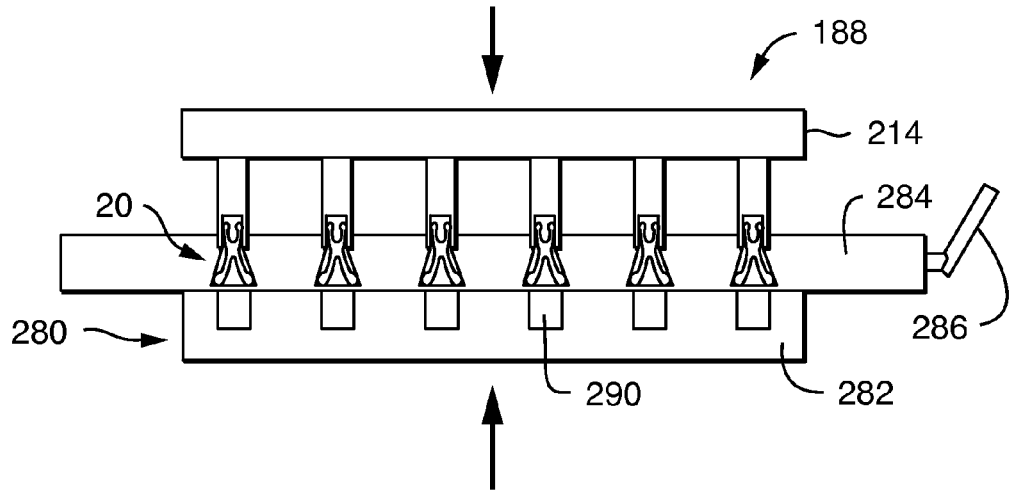
Figure 61:
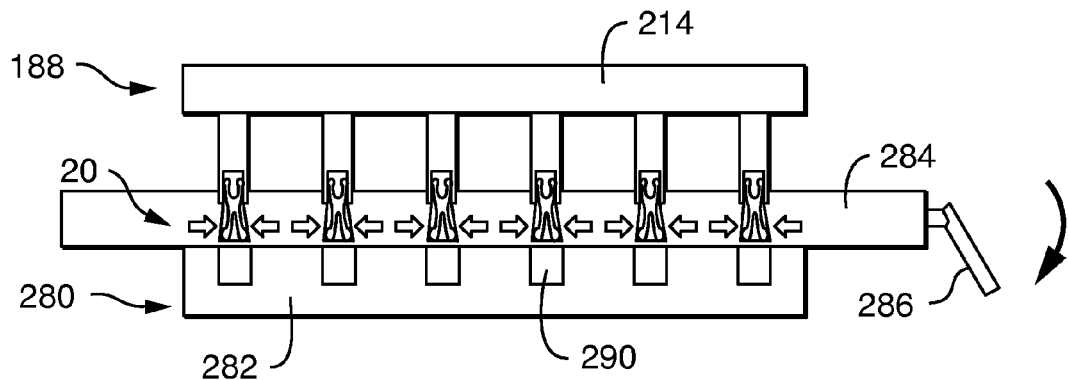
Figure 62:
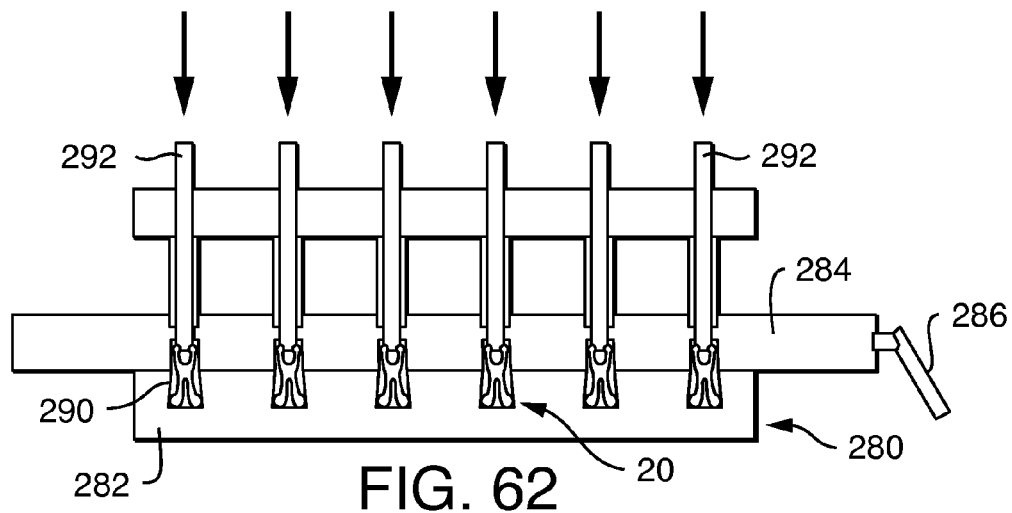

Referring to FIG. 58, the second pallet 188 can be loaded into a second pallet loading zone 302 located above a compressor 284 and placed on the inverter 308 and the third pallet can be loaded into a third pallet loading zone 304 located below a compressor 284. The second pallet can be loaded with the core 12 and cover blank 68 combination facing upward away from the compressor 284. Referring to FIG. 59, the second pallet 188 can be inverted by grasping the inverter handle 322 and rotating the inverter 180° until the core 12 and cover blank 68 combination are oriented downwards in the direction of the compressor 284. Referring to FIG. 60 the inverter 308 and the second pallet 188 can be lowered to its lowest position such that the supporting element 20 and the removal element 16 are positioned with the compressor 284. A vacuum can be utilized to assist in drawing the removal element 16 into the openings of the compressor 284. Using the foot peddle 306, the foot peddle 306 can be pressed down upon which can cause an associated lever to raise the third pallet 290 upwards towards the compressor 284. Referring to FIG. 61, the compressor handle 286 can be actuated to collapse the jaws of the compressor 284 and move the compression blocks 298 located within the compressor 284 base 296 towards each other. The compression blocks 298 can shift at a 45° angle relative to the transfer module 300. To enable the shifting, the compressor 284 can have jaw connection mechanisms such as, but not limited to, slides, guide rails, linear bearings, or rack and pinion arrangements. The compression can collapse the core 12 and the cover blank 68 combination to enable transfer of the core 12 and cover blank 68 combination from the second pallet 188 to the third pallet 290. In various embodiments, the compression of the compressor 284 can be actuated via air cylinder, pneumatic power, hydraulic power, or manual manipulation of the compressor 284. Referring to FIG. 62, push rods 292 can be activated to move through an open area in the base of the second pallet 188 and push the core 12 and cover blank 68 combination out of the second pallet 188 and into the third pallet 280. Referring to FIG. 63, following the transfer of the core 12 and cover blank 68 combination from the second pallet 188 to the third pallet 280, the push rods 292 can be retracted and the second pallet 188 can be inverted and returned to the second pallet's 188 original starting position. The compressor handle 286 can be actuated to release the compressor 284 and the third pallet 280 can be lowered by releasing the foot pedal 306. The third pallet 280 can continue on in the manufacturing process, such as illustrated in FIG. 64.

The third pallet 280 can convey the core 12 and cover blank 68 combination to a pleater module. As the cover blank 68 can already have side seams, 72 and 74, and a supporting element seam 174, the pleater module can provide an anchoring element seam for the cover blank 68. Similar to the formation of the pleats in the layers 70 and 80 of the cover blank 68 earlier in the manufacturing process, the top edges of the layers 70 and 80 of the cover blank 68 can be pleated in an "H" configuration, as viewed from the top of the cover blank 68. After the cover blank 68 can be pleated, the layers 70 and 80 of the cover blank 68 can be bonded to create an anchor element seam which can complete the cover 14 that can fully enclose the core 12 within the cover 14.

Figure 68:
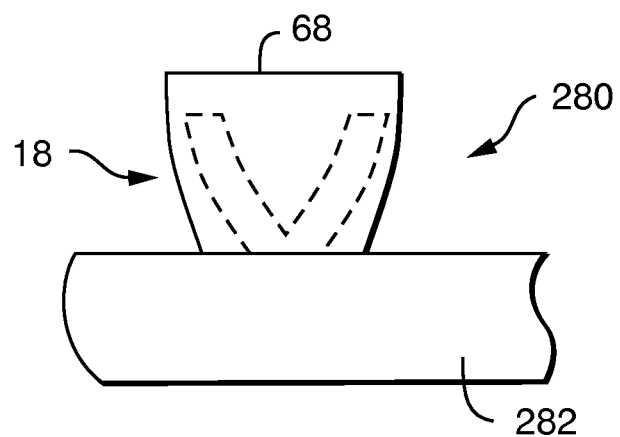
FIG. 68 is a front view of an exemplary embodiment of a portion of a third pallet with a core and cover blank combination.
Figure 69:
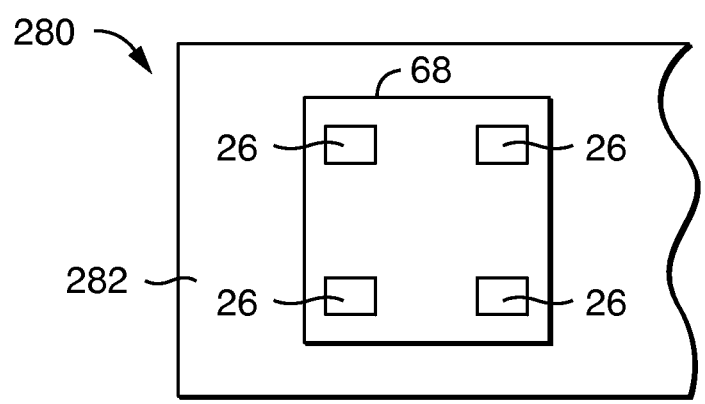
FIG. 69 is a top view of the third pallet of FIG. 68.
Figure 70:
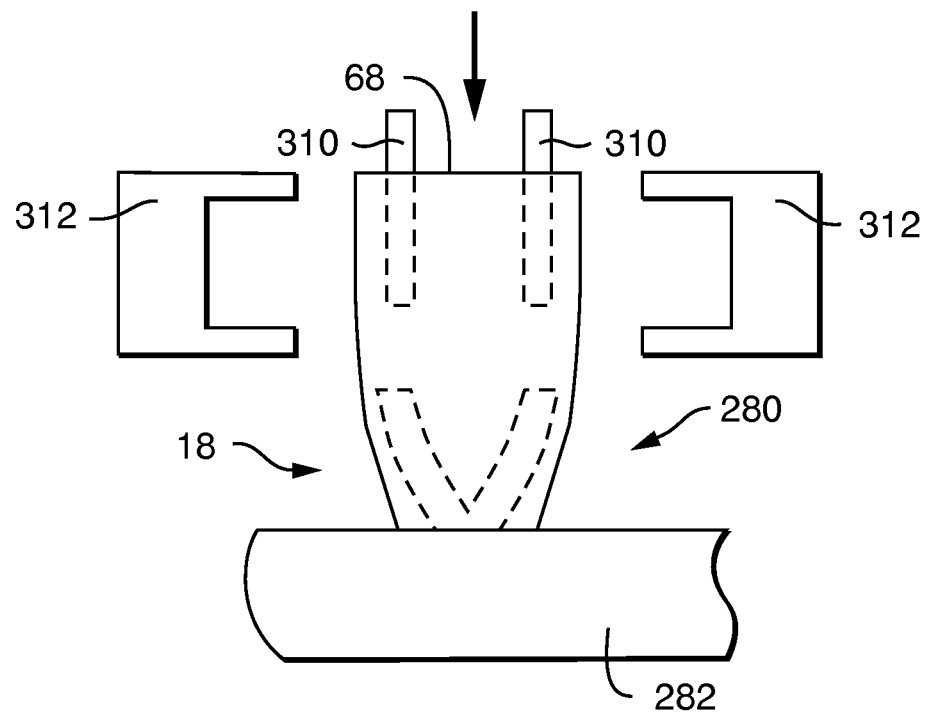
FIG. 70 is a schematic illustration of an exemplary process step in the pleating of a cover blank.
Figure 71:
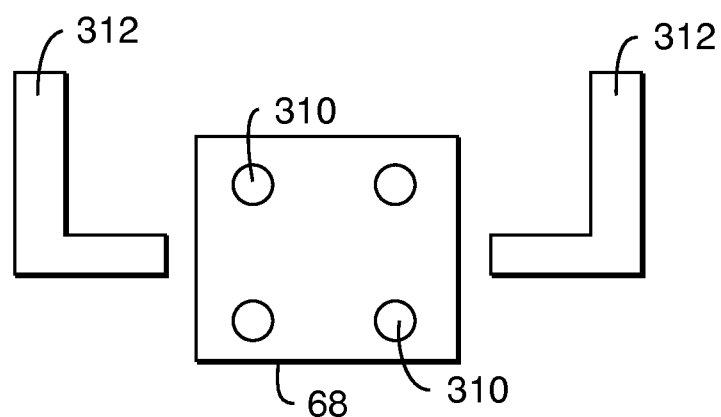
FIG. 71 is a schematic top view of the process step of FIG. 70.
Figure 72:
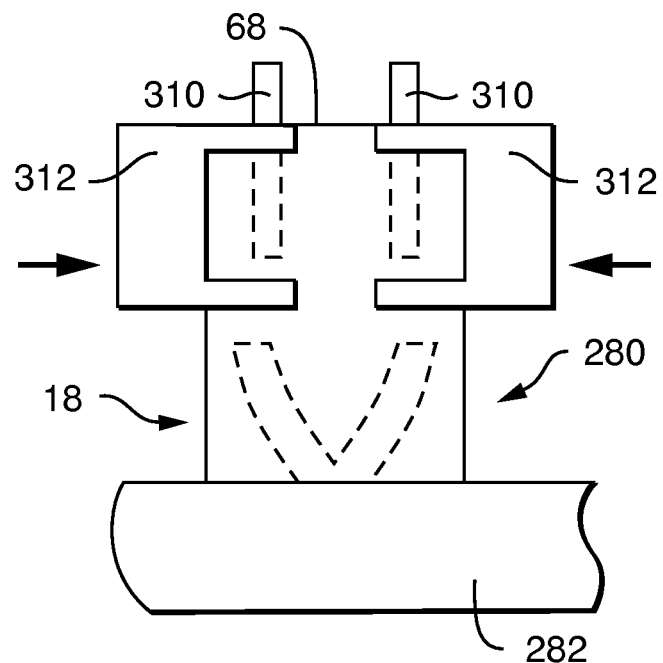
FIG. 72 is a schematic illustration of an exemplary process step in the pleating of a cover blank.
Figure 73:
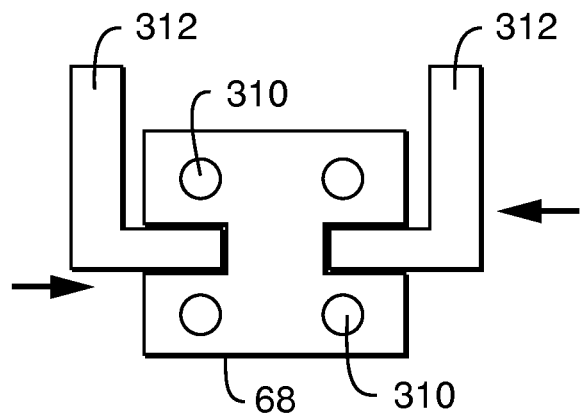
FIG. 73 is a schematic top view of the process step of FIG. 72.
Figure 74:
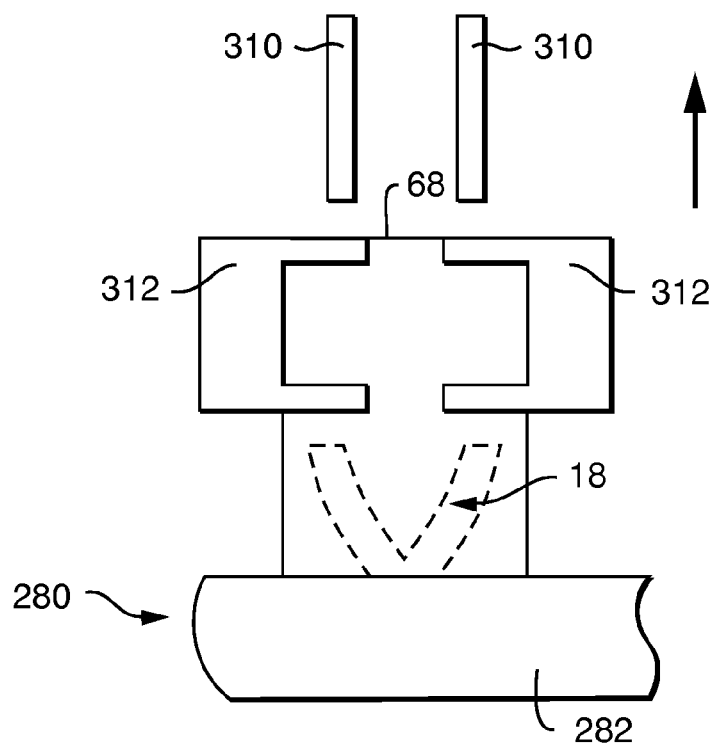
FIG. 74 is a schematic illustration of an exemplary process step in the pleating of a cover blank.
Figure 75:
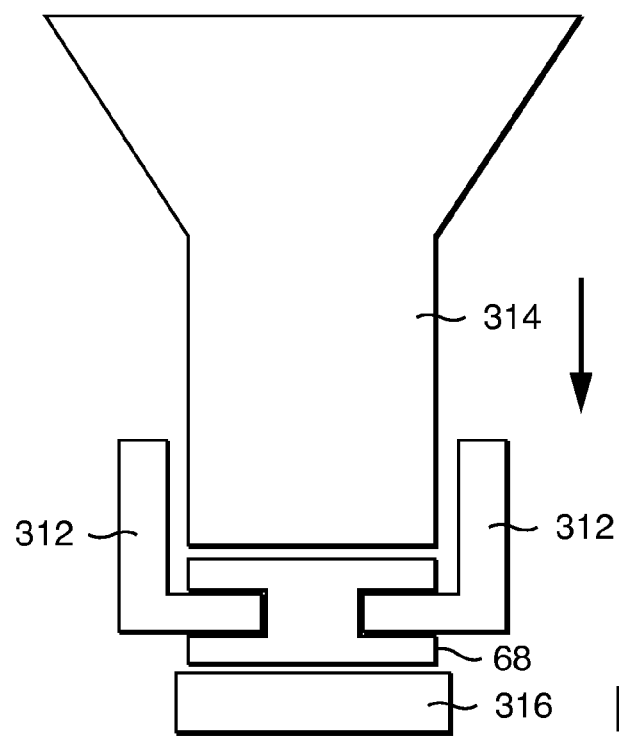
FIG. 75 is a schematic top view of an exemplary process step in the bonding of a cover blank.
Figure 76:
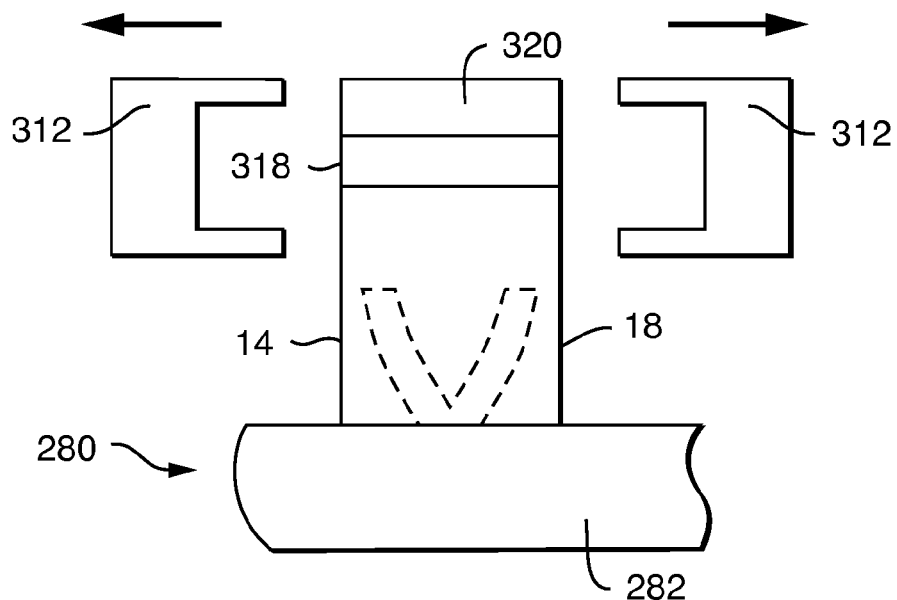
FIG. 76 is a schematic illustration of an exemplary process step in the bonding of a cover blank.

Referring to FIGS. 68-76, the pleater module can pleat and bond the layers 70 and 80 of the cover blank 68 to create an anchor end seam. FIG. 68 provides a front view and FIG. 69 provides a top view of a third pallet 280 as it can be conveyed to the pleater module. The anchoring element 18 of the core 12 can extend above the third pallet 280 and a portion of cover blank 68 material can extend beyond the anchoring element 18. FIG. 70 can provide a front view and FIG. 71 can provide a top view of the lowering of pins 310 inside the cover blank 68 and the movement of tuck bars 312 towards the sides and middle of the cover blank 68. In an embodiment, four pins 310 can assist in maintaining the open configuration of the cover blank 68. FIG. 72 can provide a front view and FIG. 73 can provide a top view of the movement of the tuck bars 312 into the cover blank 68 between the pins 310. This movement of the tuck bars 312 can create the "H" configuration of the pleat. FIG. 74 can provide an illustration that once the pleat has been created, the pins 310 can be removed from within the cover blank 68. After the pins 310 are removed from within the cover blank 68, the layers 70 and 80 of the cover blank 68 can be bonded, such as, for example, being ultrasonically welded such as illustrated in FIG. 75. Once the bonding of the layers 70 and 80 of the cover blank 68 is complete, the tuck bars 312 can retract to their starting positions and the cover blank 68 can have a bonded area 318 which can ultimately become the anchor element seam for the cover blank 68. Once the anchor element seam for the cover blank 68 can be formed, the core 12 can be fully enclosed within the cover 14. As can be seen in the exemplary embodiment illustrated in FIG. 76, an area of trim 320 can be created during the bonding process. This area of trim 320 can be removed in a fashion similar to the methods previously described for removing areas of trim.

While the cover 14 can have a core 12 enclosed within, it may be desirable to conform the cover 14 to the overall shape and configuration of the core 12. Reasons and methods for conforming a cover 14 to a core 12 have been previously discussed. One method, such as, forming a band and attaching the band can be further detailed herein. A band forming module can apply a band 344 on cover 14 of the vaginal insert 10. In various embodiments, the band 344 can be configured from a material such as a nonwoven material. In various embodiments, the band 344 can be configured from a material such as a film. In various embodiments, the band 344 can be configured from a woven material. In various embodiments, the band 344 can be configured from a material which can be the same material used to configure the cover 14.

Figure 77:
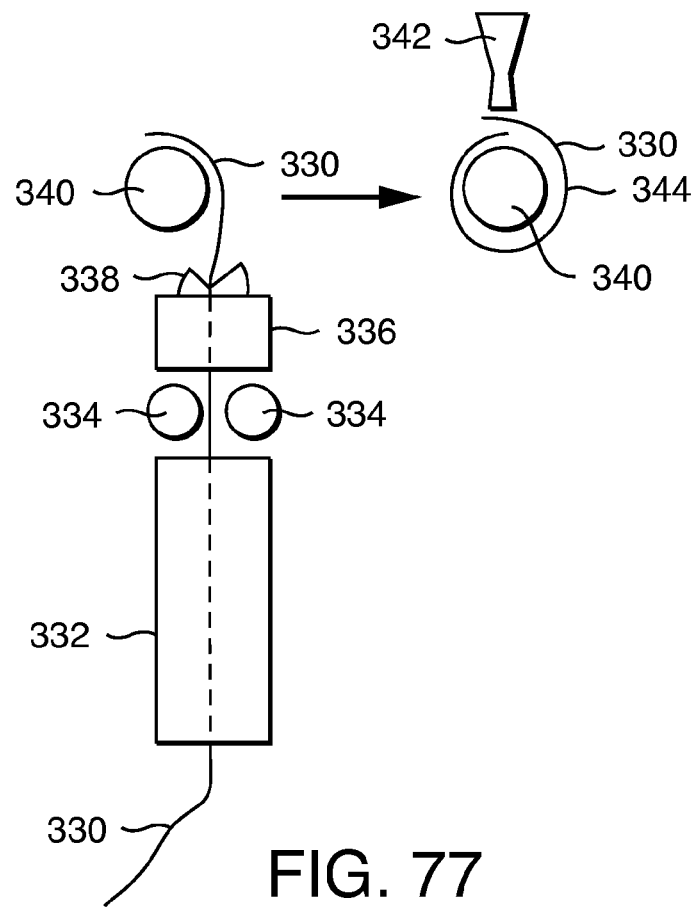
FIG. 77 is a schematic illustration of an exemplary process step in forming a band for a cover.

The band forming process can produce a small band 344 of material that can be placed on the cover 14 of the vaginal insert 10. The process of forming a band 344 can be illustrated in FIG. 77. The material 330 for the band 344 can be fed from a roll and can be routed via a mechanical web guide 332 to feed rollers 334. The material 330 can have a width from about 3, 4 or 5 mm to about 6, 7 or 8 mm. In an embodiment, the material 330 can have a width of about 6 mm. In an embodiment, one of the rollers 334 can be controlled via a servo motor and the other of the feed rollers 334 can be driven via friction. Each friction driven roller can have an adjustable spring tensioner to increase or decrease the force of the rollers 334. In various embodiments, the movement of the material 330 through the web guide 332 can be effected by an air pressure differential. In various embodiments, the air pressure differential can be such that the area of lower pressure is located in the area of the mandrel 340. In an embodiment, the material 330 can move through the mechanical web guide 332 by being pushed through with compressed air. In various embodiments, the movement of the material 330 through the web guide 332 can occur via pulling on the material 330 with a vacuum. The feed rollers 334 can feed the material 330 into a second web guide mechanism 336. The second web guide mechanism 336 can utilize compressed air to feed the material 330 onto the mandrel 340. The material 330 can be fed to a mandrel 340 and the mandrel can use a vacuum to control the material 330 once it is placed on the mandrel. Once the desired length of material 330 has been fed onto the mandrel 340, a cutter, such as scissors 338, on the second web guide mechanism 336 can cut the material 330. The mandrel 340 can rotate and the material 330 can wrap around the mandrel 340. FIG. 78 provides an illustration of a vacuum hole pattern 350 on the mandrel 340 to maintain the material 330 for the band 344 in place on the mandrel 340. The pattern 350 can have a series of horizontal holes to the left of a backwards facing "C." The material 330 can be placed onto the mandrel at the right hand side of the "C" (i.e., the three vertical holes in the pattern 350) and the mandrel 340 and the pattern 350 can continue to rotate until the end of the cut material 330 overlaps with the three vertical holes in the pattern 350. Once the material 330 has overlapped itself on the mandrel 340, the material 330 can be bonded to itself, such as, for example, through the use of an ultrasonic horn 342 or any other method of bonding mentioned herein— such as, for example, adhesive, thermal bonding and/or pressure bonding. The bonding of the material 330 to itself can occur in the open area of the backwards "C" in the pattern 350. The bonding of the material 330 to itself can create the band 344 which can be placed onto the cover 14 of the vaginal insert 10.

Once a band 344 has been manufactured it can be placed on a cover 14 of a vaginal insert 10. FIG. 79 can illustrate the process of placing a band 344 on a cover 14 of a vaginal insert 10. The mandrel 340 can have two sections: the top section can be connected to a vacuum source and can be the location where the material 330 can wrap around the mandrel 340 to form the band 344. The bottom section of the mandrel can be hollow to allow the vaginal insert 10 to be pushed inside the mandrel to enable the band 344 to be slipped onto the cover 14 of the vaginal insert 10. The anchoring element 18 of the vaginal insert 10 can be compressed. Following compression of the anchoring element 18 of the vaginal insert 10, the third pallet 280 in which the vaginal insert 10 is located can be raised up and the compressed anchoring element 18 of the vaginal insert 10 can be positioned inside the mandrel 340. A band stripper 356 located on the mandrel 340, and above the band 344, can move down the mandrel 340 and towards the vaginal insert 10. As the band stripper 356 can move down the mandrel, the band stripper 356 can move the band 344 which had been in position on the mandrel 340 down over the compressed anchor element 18 of the vaginal insert 10. The third pallet 280 can be lowered, the anchoring element 18 of the vaginal insert can be removed from inside the mandrel 340 and the band 344 can be in position on the vaginal insert 10.

Figure 80:
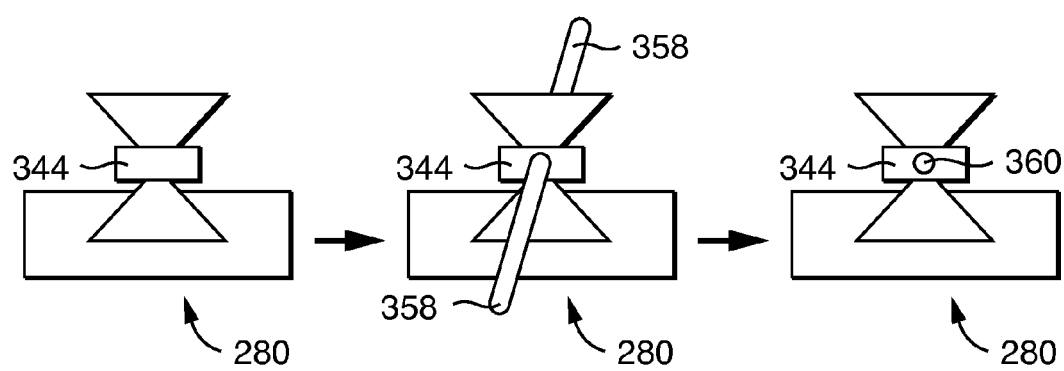
FIG. 80 is a schematic illustration of an exemplary process of welding a band to a cover.

A heat staking process can weld the band 344 to cover 14 of the vaginal insert 10 on both the front and back sides of the vaginal insert 10. FIG. 80 provides a schematic of an exemplary process of heat staking the band 344. Heated elements 358 can be briefly compressed to the band 344 on the cover 14 of the vaginal insert 10 to form the weld which can maintain the band 344 in position on the cover 14 of the vaginal insert 10.

Following the manufacture of the vaginal insert 10 and the conformation of the cover 14 to the core 12 of the vaginal insert 10, the vaginal insert 10 can be placed into an applicator 40 such as described herein to ease insertion of the vaginal insert 10 into the vagina.

It is to be noted that while the description herein provides an exemplary embodiment of the process of manufacturing a vaginal insert 10, additional embodiments are also contemplated. For example, the exemplary embodiment of the process of manufacture described herein can generally describe inserting a core 12 into a cover blank 68 through an opening between the top edges 76 of the two layers 70 and 80 of the cover blank 68. It is to be noted that, in various embodiments, insertion of the core 12 into the cover blank 68 can occur through an opening between bottom edges 78 of the two layers, 70 and 80, of the cover blank 68 or through an opening between side edges of layers 70 and 80 of the cover blank 68. It is also contemplated that, while the description herein generally describes bonding the bottom edges 78 of the layers 70 and 80 of a cover blank 68 prior to bonding of the top edges 76 of layers 70 and 80 of the cover blank 68, in various embodiments, the top edges 76 of layers 70 and 80 of the cover blank 68 can be bonded prior to the bonding of the bottom edges 78 of layers 70 and 80 of the cover blank 68.

It is also noted that while the description herein generally provides an exemplary embodiment of each of the core insertion module 180, the stringer and knot modules, the transfer module 300, the pleater module, and the band forming module, additional embodiments are also contemplated. For example, in some portions of the description herein, some components of the various module are described as being "above" or "below" other components of the same module, and in some portions of the description herein, some components are described as being in a particular "level" of the module, such as, a "top level," "middle level," or "bottom level." It is contemplated that the orientation of the modules can be reversed such that, for example, components that are currently described as being "above" another component can, in various contemplated embodiments, be "below" that component and that some components which are currently described as being in a "top level" can, in various contemplated embodiments, be in a "bottom level."

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of conforming a cover to a vaginal insert, the vaginal insert comprising a core and the cover, the method comprising the steps of:
  a. providing the core, the core comprising:
    i. an anchoring element;
    ii. a supporting element; and
    iii. a node connecting the anchoring element and the supporting element;
  b. providing a cover blank, the cover blank, when viewed in flat configuration prior to a step of inserting the core into the cover blank, comprising:
    i. a first layer of material and a second layer of material in a face-to-face relationship with the first layer of material;
    ii. a four-sided trapezoidal shape when viewed in a flat configuration prior to the step of inserting the core into the cover blank, wherein two sides of the four-sided trapezoidal shape are provided by a first side seam and a second side seam bonding the first layer of material to the second layer of material, a third side of the four-sided trapezoidal shape is provided by a third side seam bonding the first layer of material to the second layer of material wherein the third side seam extends between and connects the first side seam and the second side seam, and the fourth side of the four-sided trapezoidal shape is provided by an unbonded opening between a pair of overlapping end edges wherein a first end edge of the pair of overlapping end edges is a portion of the first layer of material and a second end edge of the pair of overlapping end edges is a portion of the second layer of material, wherein the fourth side of the four-sided trapezoidal shape is parallel to the third side and extends between and connects the first side seam and the second side seam; and
    iii. a first width dimension of the third side of the trapezoidal shape and a second width dimension of the fourth side of the trapezoidal shape which is greater than the first width dimension;
  c. inserting the core into the cover blank to form a core and cover blank combination;
  d. bonding together the portions of the first layer of material and the second layer of material forming the fourth side of the four-sided trapezoidal shape of the cover blank to form a fourth side seam to fully encase the core within the four side seams thereby converting the cover blank to a cover; and
  e. conforming the cover to the core in the area of the node of the core by reducing the dimension of the cover at the node of the core wherein the step of reducing the dimension of the cover at the node can further comprise a step of wrapping a band of material around the cover at the node of the core and maintaining the reduced dimension of the cover by attaching the band to the cover.

2. The method of claim 1 further comprising the step of compressing the anchoring element of the core and sliding the band of material over the compressed anchoring element of the core.

3. The method of claim 1 wherein the step of inserting the core into the cover blank further comprises the step of inverting the cover blank over the core.

* * * * *